US008329650B2

(12) United States Patent
Walsh et al.

(10) Patent No.: US 8,329,650 B2
(45) Date of Patent: Dec. 11, 2012

(54) METHOD OF TREATING ISCHEMIC INJURY WITH FOLLISTATIN-LIKE 1 POLYPEPTIDE

(75) Inventors: Kenneth Walsh, Carlisle, MA (US); Yuichi Oshima, Brookline, MA (US); Noriyuki Ouchi, Nagoya (JP)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 12/682,898

(22) PCT Filed: Oct. 20, 2008

(86) PCT No.: PCT/US2008/080464
§ 371 (c)(1),
(2), (4) Date: Apr. 14, 2010

(87) PCT Pub. No.: WO2009/052478
PCT Pub. Date: Apr. 23, 2009

(65) Prior Publication Data
US 2010/0227817 A1 Sep. 9, 2010

Related U.S. Application Data

(60) Provisional application No. 60/981,247, filed on Oct. 19, 2007.

(51) Int. Cl.
*A61P 9/10* (2006.01)
*A61P 39/06* (2006.01)
*C07K 14/545* (2006.01)

(52) U.S. Cl. ...... 514/15.1; 514/1.9; 514/16.4; 514/21.2; 514/824; 514/866; 530/350

(58) Field of Classification Search .................. None
See application file for complete search history.

(56) References Cited

U.S. PATENT DOCUMENTS

| 2006/0046259 | A1 | 3/2006 | Baird et al. |
| 2006/0275770 | A1 | 12/2006 | Bednarik |
| 2007/0224596 | A1 | 9/2007 | Nacht et al. |
| 2007/0253901 | A1 | 11/2007 | Deng et al. |
| 2007/0259377 | A1 | 11/2007 | Urdea et al. |
| 2010/0227817 | A1 * | 9/2010 | Walsh et al. ............ 514/12 |

FOREIGN PATENT DOCUMENTS

WO 2005/033134 4/2005
WO WO 2007109686 A2 * 9/2007

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Descamps et al, 2009. Curr Gene Therapy. 9(2):115-27).*
Phillips, J Pharm Pharmacology 53: 1169-1174, 2001.*
Lara-Pezzi et al., J Mol Cellular Cardiol, 42(supp 1): S147 (2007). "Follistatin gene expression is elevated in heart failure and decreases following recovery."
Amano, K. et al., Hypertension, 41(1):156-162 (2003). "Enhancement of ischemia-induced angiogenesis by eNOS overexpression."
Fujio, Y. et al., Journal of Biological Chemistry, 274(23):16349-16354 (1999). "Akt mediates cytoprotection of endothelial cells by vascular endothelial growth factor in an anchorage-dependent manner."
Fulton, D. et al., Nature, 399:597-601 (1999). "Regulation of endothelium-derived nitric oxide production by the protein kinase Akt."
Gelinas, D.S. et al., British Journal of Pharmacology, 137(7):1021-1030 (2002). "Immediate and delayed VEGF-mediated NO synthesis in enthodelial cells: Role of PI3K, PKC and PLC pathways."
Johnston, I.M.P. et al., Oncogene, 19(47):5348-5358 (2000). "Regulation of a multigenic invasion programme by the transcription factor, AP-1: Re-expression of a down-regulated gene, TSC-36, inhibits invasion."
Kuwabara, M. et al., Journal of Physiological Sciences, 56(1):95-101 (2006). "Nitric oxide stimulates vascular endothelial growth factor production in cardiomyocytes involved in angiogenesis."
Lara-Pezzi, E. et al., Endocrinology, 149(11):5822-5827 (2008). "Expression of Follistatin-related genes is altered in heart failure."
Le Luduec, J.B. et al., American Journal of Transplantation, 8(11):2297-2306 (2008). "An immunomodulatory role for follistatin-like 1 in heart allograft transplantation.".
Liu, S. et al., Experimental and Molecular Pathology, 80(2):132-140 (2006). "TSC-36/FRP inhibits vascular smooth muscle cell proliferation and migration.".
Matsui, T. et al., Circulation, 104(3):330-335 (2001). "Akt activation preserves cardiac function and prevents injury after transient cardiac ischemia in vivo."
Oshima, Y. et al., Circulation, 116(16), Suppl. S:221 (2007). "Cardioprotective action of follistatin like-1, a secreted anti-apoptotic factor regulated by Akt1."
Oshima, Y. et al., Circulation, 117(24):3099-3108 (2008). "Follistatin-like 1 is an Akt-regulated cardioprotective factor that is secreted by the heart."
Ouchi, N. et al., Journal of Biological Chemistry, 283(47):32802-32811 (2008). "Follistatin-like 1, a secreted muscle protein, promotes endothelial cell function and revascularization in ischemic tissue through a nitric-oxide synthase-dependent mechanism."
Roy et al., Physiological Genomics, 25(3):364-374 (2006). "Transcriptome analysis of the ischemia-reperfused remodeling myocardium: temporal changes in inflammation and extracellular matrix."

(Continued)

*Primary Examiner* — Zachary Howard
(74) *Attorney, Agent, or Firm* — Nixon Peabody LLP

(57) ABSTRACT

Described herein are methods and compositions related to the discovery that the Follistatin-like 1 protein (Fstl-1) has metabolic and cardioprotective effects in vivo. Fstl-1 and portions and derivatives or variants thereof can be used to treat or prevent metabolic diseases or disorders and to treat or prevent cardiac damage caused by interrupted cardiac muscle blood supply.

10 Claims, 22 Drawing Sheets

OTHER PUBLICATIONS

Schiekofer, S. et al., Physiological Genomics, 27(2):156-170 (2006). "Microarray analysis of Akt1 activation in transgenic mouse hearts reveals transcript expression profiles associated with compensatory hypertrophy and failure.".

Shibanuma, M. et al., European Journal of Biochemistry, 217(1):13-19 (1993). "Cloning from a mouse osteoblastic cell line of a set of transforming-grwoth-factor-beta1-regulated genes, one of which seems to encode a follistatin-related polypeptide."

Sumitomo, K. et al., Cancer Letters, 155(1):37-46 (2000). "Expression of a TGF-[beta[1 inducible gene, TSC-36, causes growth inhibition in human lung cancer cell lines."

* cited by examiner

US 8,329,650 B2

METHOD OF TREATING ISCHEMIC INJURY WITH FOLLISTATIN-LIKE 1 POLYPEPTIDE

CROSS REFERENCE TO RELATED APPLICATIONS

This application is a 35 U.S.C. §371 National Phase Entry Application of International Application No. PCT/US2008/080464 filed Oct. 20, 2008, which designates the U.S., and which claims benefit of priority under 35 U.S.C. §119(e) of U.S. Provisional Patent Application No. 60/981,247 filed Oct. 19, 2007, which is hereby incorporated by reference in its entirety.

FIELD OF THE INVENTION

The invention relates to the treatment and prevention of metabolic disorders and cardiac muscle damage.

BACKGROUND OF THE INVENTION

The metabolic disease diabetes is widely recognized as one of the leading causes of death and disability in the United States. In 2002, it was the sixth leading cause of death. However, diabetes is likely to be underreported as the underlying cause of death on death certificates. About 65 percent of deaths among those with diabetes are attributed to heart disease and stroke.

Diabetes is associated with long-term complications that affect almost every part of the body. The disease often leads to blindness, heart and blood vessel disease, stroke, kidney failure, amputations, and nerve damage. Uncontrolled diabetes can complicate pregnancy, and birth defects are more common in babies born to women with diabetes.

In 2002, diabetes cost the United States $132 billion. Indirect costs, including disability payments, time lost from work, and premature death, totaled $40 billion; direct medical costs for diabetes care, including hospitalizations, medical care, and treatment supplies, totaled $92 billion.

Heart disease, including coronary artery disease and myocardial infarction is also a leading killer Regardless of the initial cause, the ultimate manifestation of heart disease generally results from ischemic damage to the heart muscle.

SUMMARY OF THE INVENTION

The inventors have discovered that the Follistatin-like 1 protein (Fstl-1) has metabolic and cardioprotective effects in vivo. In particular, it is demonstrated herein that Fstl-1 expression modulates the expression of metabolic regulatory factors in skeletal muscle, regulates metabolic properties in liver and glucose metabolism, and protects cultured cardiomyocytes from hypoxia/reoxygenation-induced apoptosis and protects the myocardium from ischemia/reperfusion injury in vivo. Fstl-1 and portions and derivatives or variants thereof can be used to treat or prevent metabolic diseases or disorders and to treat or prevent cardiac damage caused by interrupted cardiac muscle blood supply.

Disclosed herein are methods of treating or preventing ischemic injury in a mammal, the methods comprising administering a follistatin-like protein 1 polypeptide or a protective portion thereof to a mammal in need thereof, wherein administering the Fstl-1 protein and effective portions or derivatives thereof treats or prevents ischemic injury.

Also disclosed are methods of preventing apoptosis in cardiac tissue, the method comprising administering to a mammal in need thereof a follistatin-like protein 1 or a protective portion thereof, wherein such administering prevents apoptosis in cardiac tissue of the mammal.

Also disclosed are methods of modifying glucose metabolism in an individual in need thereof, the method comprising administering a follistatin-like protein 1 polypeptide or a portion thereof effective to modify glucose metabolism to a mammal in need thereof, wherein such administering modifies glucose metabolism in the individual.

Also disclosed are methods of treating diabetes in an individual in need thereof, the method comprising administering a follistatin-like protein 1 polypeptide, or a portion thereof effective to modify glucose metabolism, to a mammal in need thereof, wherein said administering improves glucose tolerance in said individual.

In specific embodiments of such methods, the ischemic injury or apoptosis is induced by ischemia or ischemia/reperfusion. In particular embodiments, the ischemic injury is ischemic injury of cardiac muscle.

In other specific embodiments of such methods, the administering comprises administering a soluble follistatin-like protein 1 polypeptide or a protective portion thereof.

In other specific embodiments of such methods, the administering comprises administering a vector encoding the follistatin-like protein 1 polypeptide or protective portion thereof. The vector can be any vector that directs the expression of recombinant Fstl-1 when introduced to a cell. In one embodiment, the vector is a viral vector, e.g., an adenoviral vector, a poxvirus vector, a lentiviral vector. Additionally, plasmid vectors have been shown to be effective to drive expression of exogenous gene constructs when directly injected to skeletal muscle. Thus, plasmid vectors are specifically contemplated for use in delivery of Fstl-1 polypeptides as described herein. Expression from such plasmids, like the viral constructs, can be under the regulation of muscle-specific regulatory elements.

In specific embodiments of methods of regulating glucose metabolism, the individual is diabetic.

In other specific embodiments, the modification of the glucose metabolism comprises improved glucose tolerance.

Further disclosed are plasmids and viral vectors comprising nucleic acid sequence encoding a follistatin-like protein 1 polypeptide or a portion thereof effective for the treatment or prevention of ischemia/reperfusion injury. Also encompassed are cells comprising such a plasmid or viral vector. In specific embodiments, the viral vector can be a vector selected from the group consisting of an adenoviral vector, a poxvirus vector, a lentiviral vector. In other specific embodiments of such vectors, the nucleic acid sequence encoding a follistatin-like protein 1 polypeptide or a portion thereof is operatively linked to a tissue- or cell-type-specific promoter. As one example, example, the viral vector can include a skeletal or cardiac muscle-specific promoter.

Further disclosed are pharmaceutical compositions comprising a Fstl-1 polypeptide or protective portion thereof, or a vector encoding such a vector, plus a pharmaceutically acceptable carrier. Administration of such pharmaceutical compositions can provide therapeutic benefit for the modification of glucose metabolism and for the protection of muscle, particularly cardiac muscle from ischemic injury.

Also described herein is a method of promoting revascularization of ischemic tissue, the method comprising administering to a mammal in need thereof a follistatin-like protein 1 polypeptide or a portion thereof sufficient to activate Akt-1 signaling activity, wherein the administering promotes increased blood flow in the tissue.

In one embodiment of this aspect and all other aspects described herein, the tissue is muscle. In another embodiment of this aspect and all other aspects described herein, the muscle is cardiac or skeletal muscle.

In another embodiment of this aspect and all other aspects described herein, the administering promotes endothelial cell growth, survival and/or differentiation.

In another embodiment of this aspect and all other aspects described herein, the mammal suffers from an ischemic limb disease. In another embodiment of this aspect and all other aspects described herein, the mammal suffers from diabetes, or atherosclerosis.

Also described herein is a method of increasing angiogenesis in an ischemic tissue, the method comprising administering to a mammal in need thereof a follistatin-like protein 1 polypeptide or a portion thereof sufficient to activate Akt-1 signaling activity, wherein the administering promotes angiogenesis in an ischemic tissue of the mammal.

Further described herein is a method of preventing or reducing apoptosis of endothelial cells in an ischemic tissue, the method comprising administering to a mammal in need thereof a follistatin-like protein 1 polypeptide or a portion thereof sufficient to activate Akt-1 signaling activity, wherein the administering prevents or reduces apoptosis of endothelial cells of an ischemic tissue of the mammal.

Further described herein is a use of a follistatin-like protein 1 polypeptide or a protective portion thereof, in the preparation of a medicament for the treatment of ischemic injury.

In one embodiment of this aspect and all other aspects described herein, the ischemic injury comprises an ischemic limb disease.

In another embodiment of this aspect and all other aspects described herein, the ischemic injury occurs in a mammal suffering from diabetes, or atherosclerosis.

In another embodiment of this aspect and all other aspects described herein, the ischemic injury comprises myocardial ischemia or myocardial ischemia/reperfusion injury.

In another embodiment of this aspect and all other aspects described herein, the use promotes endothelial cell growth, survival and/or differentiation.

Another aspect described herein relates to use of a follistatin-like protein 1 polypeptide or a protective portion thereof, for the treatment of ischemic injury.

Further described herein is the use of a follistatin-like protein 1 polypeptide or a protective portion thereof for preventing cardiac apoptosis.

In one embodiment of this aspect and all other aspects described herein, the apoptosis is induced by ischemia or ischemia/reperfusion.

In another embodiment of this aspect and all other aspects described herein, the follistatin-like protein 1 comprises a soluble follistatin-like protein 1 polypeptide or a protective portion thereof.

In another embodiment of this aspect and all other aspects described herein, the follistatin-like protein 1 polypeptide is comprised by a vector encoding said follistatin-like protein 1 polypeptide.

In another embodiment of this aspect and all other aspects described herein, the vector is selected from the group consisting of an adenovirus vector, a poxvirus vector, and a lentiviral vector.

Also described herein is the use of a follistatin-like protein 1 polypeptide or a portion thereof to modify glucose metabolism in an individual.

In one embodiment of this aspect and all other aspects described herein, the individual is diabetic.

In another embodiment of this aspect and all other aspects described herein modifying glucose metabolism comprises improved glucose tolerance.

Another aspect described herein is the use of a follistatin-like protein 1 polypeptide or a protective portion thereof for the treatment of diabetes.

Further described herein is the use of a follistatin-like protein 1 polypeptide or a protective portion thereof for promoting revascularization of ischemic tissue.

In one embodiment of this aspect and all other aspects described herein the ischemic tissue is muscle.

In another embodiment of this aspect and all other aspects described herein, the ischemic tissue is cardiac or skeletal muscle.

In another embodiment of this aspect and all other aspects described herein the use promotes endothelial cell growth, survival and/or differentiation.

Another aspect described herein is the use of a follistatin-like protein 1 polypeptide or a protective portion thereof for increasing angiogenesis in an ischemic tissue.

Another aspect described herein is the use of a follistatin-like protein 1 polypeptide or a protective portion thereof for preventing or reducing endothelial cell apoptosis in an ischemic tissue.

Definitions

As used herein, the terms "follistatin-like protein 1," "follistatin-like protein 1 polypeptide" and "Fstl-1" refer to the human follistatin-like protein 1 polypeptide having an amino acid sequence as in GenBank Accession No. AAH00055, which is incorporated herein by reference. A nucleotide sequence encoding Fstl-1 is at GenBank Accession No. NM007085, which is incorporated herein by reference (see also Table 2, which includes amino acid and nucleotide sequences for Fstl-1, as SEQ ID NOs 1 and 2). The terms also refer to fragments or portions thereof that have one or more signalling, therapeutic or preventive activities of full length Fstl-1, also referred to herein as "protective portions," as well as to mutants or derivatives of the Fstl-1 polypeptide that retain one or more such activities. By "retain . . . such activity" is meant that a variant or derivative has at least 50% of the subject activity relative to full length, wild-type Fstl-1 polypeptide, preferably at least 60%, 70%, 80%, 90%, 95%, 96%, 97%, 98%, 99% or 100%, or even greater than 100% of an activity relative to the full length wild-type polypeptide. The terms "mutant," "derivative" or "variant" do not encompass other naturally-occurring follistatin-like proteins, e.g., follistatin, follistatin-like protein 3, etc. Signalling activity encompasses any natural signalling activity, non-limiting examples of which include kinase or phosphatase activity, intracellular calcium regulation, and the ability to associate with and influence the activity of another signalling protein or factor. Signalling activity, however, specifically excludes the ability to provoke an immune response that raises antibodies specific for an Fstl-1 polypeptide.

Follistatin-like protein 1 is also known as FRP and TSC-36. The protein is an extracellular glycoprotein belonging to the BM-40/SPARC/osteonectin family of proteins containing both extracellular calcium-binding and follistatin-like domains. FSTL-1 was originally cloned from an osteoblastic cell line as a TGF-β-inducible gene. The protein occurs in two isoforms resulting from differential sialylation. The domain structure of Fstl-1 has been determined by sequence comparisons. The protein has a Follistatin N-terminal domain-like structure at amino acids 29-52 (note: amino acid residue numbers are for the bovine polypeptide (GenBank Accession No. NP_001017950)—alignment with the human polypeptide (GenBank Accession No. AAH00055) permits delineation of corresponding domains in the human polypeptide), a Kazal serine protease inhibitor domain at amino acids 52-97, a low complexity region between amino acids 102-111, a region with insignificant similarity to other domains at amino acids 112-146, two EF Hand calcium-binding like domains at residues 147-174 and 196-224, and a coiled coil domain at residues 269-302. Useful portions of the polypeptide can include, for example, one or more of these structural domains, e.g., a Follistatin-like N terminal domain, a Kazal serine protease inhibitor-like domain, or an EF Hand domain. In one embodiment, portions of the Fstl-1 polypeptide that are not necessary for activity as described herein, can be removed or optionally replaced by a peptide linker(s) in order to maintain an active conformation. Thus, in one embodiment, a function portion of Fstl-1 includes the Follistatin-line 1 N-terminal domain. In another embodiment, a functional portion includes the Fstl-1 N-terminal domain and one or more of the Kazal serine protease inhibitor domain and the calcium binding domain. Other examples include two or more of these domain structures, e.g., a Follistatin-like N terminal domain and a Kazal serine protease inhibitor-like domain, a Kazal serine protease inhibitor-like domain and an EF Hand domain, two EF Hand domains, a Kazal serine protease inhibitor-like domain and two EF Hand domains, an EF Hand domain and a coiled coil, etc. In one embodiment, the Fstl-1 protective polypeptide comprises at least 20 amino acids. In other embodiments, the protective polypeptide comprises at least 30 amino acids, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, 308 amino acids (i.e., the full length Fstl-1 polypeptide) or more. The amino acid sequence can also be supplemented by other amino acids or polypeptides if so desired.

Protease inhibiting or calcium binding activity can be assayed for a given construct according to methods known in the art. The function of a given portion, fragment or variant can be assayed by introducing the portion or fragment to skeletal muscle cells in culture (see, e.g., Example 4) and assaying for one or more effects of the wild-type Fstl-1 polypeptide, e.g., changes in phosphorylation of AMP-activated protein kinase and/or ACC, or changes in levels of PGC-1-a or Glut4 in C2C12 cells. Alternatively, effects of a given fragment or portion can be monitored by administering the polypeptide to, or expressing the polypeptide in ob/ob mice (see Example 5) and measuring impact on glucose tolerance. As another alternative, any of the other assays described in the Examples herein can be used to monitor the activity of a given fragment, variant, mutein or derivative of the Fstl-1 polypeptide.

As used herein, the terms "treat," "treating," and "treatment" refer to the alleviation or measurable lessening of one or more symptoms or measurable markers of a disease or disorder; while not intending to be limited to such, disease or disorders of particular interest include ischemic or ischemia/reperfusion injury and diabetes. Measurable lessening includes any statistically significant decline in a measurable marker or symptom.

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the term "ischemic injury" refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/or necrosis and can contribute to the pathogenesis of heart failure. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis ensues. "Ischemia/reperfusion injury" refers to a subset of ischemic injury in which injury involves a period of reduced blood flow, followed by at least partial restoration of the blood flow. Ischemia/reperfusion injury involves an inflammatory response and oxidative damage accompanied by apoptosis that occur when blood flow has been restored to a tissue subjected to an interruption in blood flow. As used herein, the term "ischemic limb disease" refers to any disease resulting from lack of blood flow to a superficial limb or extremity (e.g., an arm, leg, hand, foot, toe, finger etc.). Ischemic limb disease results from complications due to diabetes or atherosclerosis, among others.

As used herein, the term "promoting revascularization" refers to an increase in capillary density as a measure of new blood vessel formation in a mammal treated with a follistatin like 1 polypeptide or portion thereof, compared to the increase in capillary density observed in the absence of an Fstl-1 polypeptide. An "increase in capillary density" means an increase of at least 5% in the presence of Fstl-1 compared to untreated subjects; preferably an increase in capillary density is at least 10%, at least 20%, at least 30%, at least 40%, at least 50%, at least 60%, at least 70%, at least 80%, at least 90%, at least 95%, at least 99%, at least 1-fold, at least 5-fold, at least 10-fold, at least 100-fold, at least 1000-fold or more in the presence of Fstl-1 compared to a that measured in the absence of Fstl-1 administration. Alternatively, an increase in revascularization can be measured non-invasively by an increase in blood flow of at least 5% as measured by laser Doppler blood flow; preferably an increase in blood flow is at least 10%, at least 20%, at least 30%, at least 40%, at least 50%, at least 60%, at least 70%, at least 80%, at least 90%, at least 95%, at least 99%, at least 1-fold, at least 5-fold, at least 10-fold, at least 100-fold, at least 1000-fold or more in the presence of Fstl-1 compared to a that measured in the absence of Fstl-1 administration.

As used herein, the term "sufficient to activate Akt-1 signaling activity", refers to a measurable increase in Akt activity of at least 10% in the presence of a Fstl-1 polypeptide compared to the level of Akt activity in the absence of a Fstl-1 polypeptide; preferably the increase in Akt activity is at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 100-fold, at least 1000-fold or more in the presence of a Fstl-1 polypeptide. A "measurable increase in Akt activity" can be determined by any method known to one of skill in the art, however for the avoidance of doubt Akt activity can be assessed by using an Akt activity assay kit from a commercial source such as e.g., EMD BIOSCIENCES™, BIOVISON™, and RND BIOSYSTEMS™.

As used herein, the phrase "prevent apoptosis" refers to the at least partial prevention or lessening of apoptosis as compared to that apoptosis that would normally occur in a given situation without the administration of an Fstl-1 polypeptide as described herein. Various measures of apoptosis are very well known in the art, and/or described in the Examples herein below. "At least partial" prevention means at least a 10% or greater reduction, including, e.g., at least 10%, 20%, 30%, 40%, 50%, 60%, 70%, 80%, 90%, 95%, 96%, 97%, 98%, 99% or even 100%, or total prevention of apoptosis.

As used herein, the phrase "modify glucose metabolism" means that the regulation of blood glucose levels in an individual is altered in a measurable way. Diabetes is characterized by the inability to properly regulate blood glucose levels, resulting in inappropriately high blood sugar (hyperglycemia). Mechanisms resulting in diabetes include either abnormally low levels of the hormone insulin, or abnormal resistance to insulin's effects coupled with inadequate levels of insulin secretion to compensate. A treatment that "modifies glucose metabolism" in a diabetic subject, as the term is used herein, will result in a lower blood glucose level in response to challenge with glucose (the so-called "glucose tolerance test") than would occur in the absence of such treatment. The term refers to at least a 10% difference in a measurable indicator of glucose metabolism. Similarly, an "improved" glucose tolerance refers to at least a 10% decrease in blood glucose levels in a glucose tolerance test at two hours post glucose administration, relative to the 2 hour blood glucose level in a glucose tolerance test performed on an individual before commencing treatment as described herein.

As used herein, the term "increase in angiogenesis" means an increase in a measurable marker of angiogenesis of at least 5% in the presence of an Fstl-1 polypeptide compared to the level of angiogenesis in the absence of an Fstl-1 polypeptide; preferably an increase in a measurable marker of angiogenesis is at least 10%, at least 20%, at least 30%, at least 40%, at least 50%, at least 60%, at least 70%, at least 80%, at least 90%, at least 95%, at least 99%, at least 1-fold, at least 5-fold, at least 10-fold, at least 100-fold, at least 1000-fold or more in the presence of Fstl-1 compared to a that measured in the absence of Fstl-1 administration. As used herein the term "measurable marker of angiogenesis" refers to markers of angiogenic activity such as increased endothelial cell proliferation, increased capillary density, increased laser Doppler blood flow measurements, increase in endothelial cell growth, an increase in endothelial cell differentiation and/or blood vessel tube formation. Angiogenesis can also be measured using a Matrigel plug assay as known to those of skill in the art.

By "pharmaceutically acceptable" it is meant the carrier, diluent, excipients, and/or salt must be compatible with the other ingredients of the formulation, and not deleterious to the recipient thereof. Pharmaceutically acceptable carriers do not include tissue culture medium, and particularly not medium containing serum.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Figure 1:
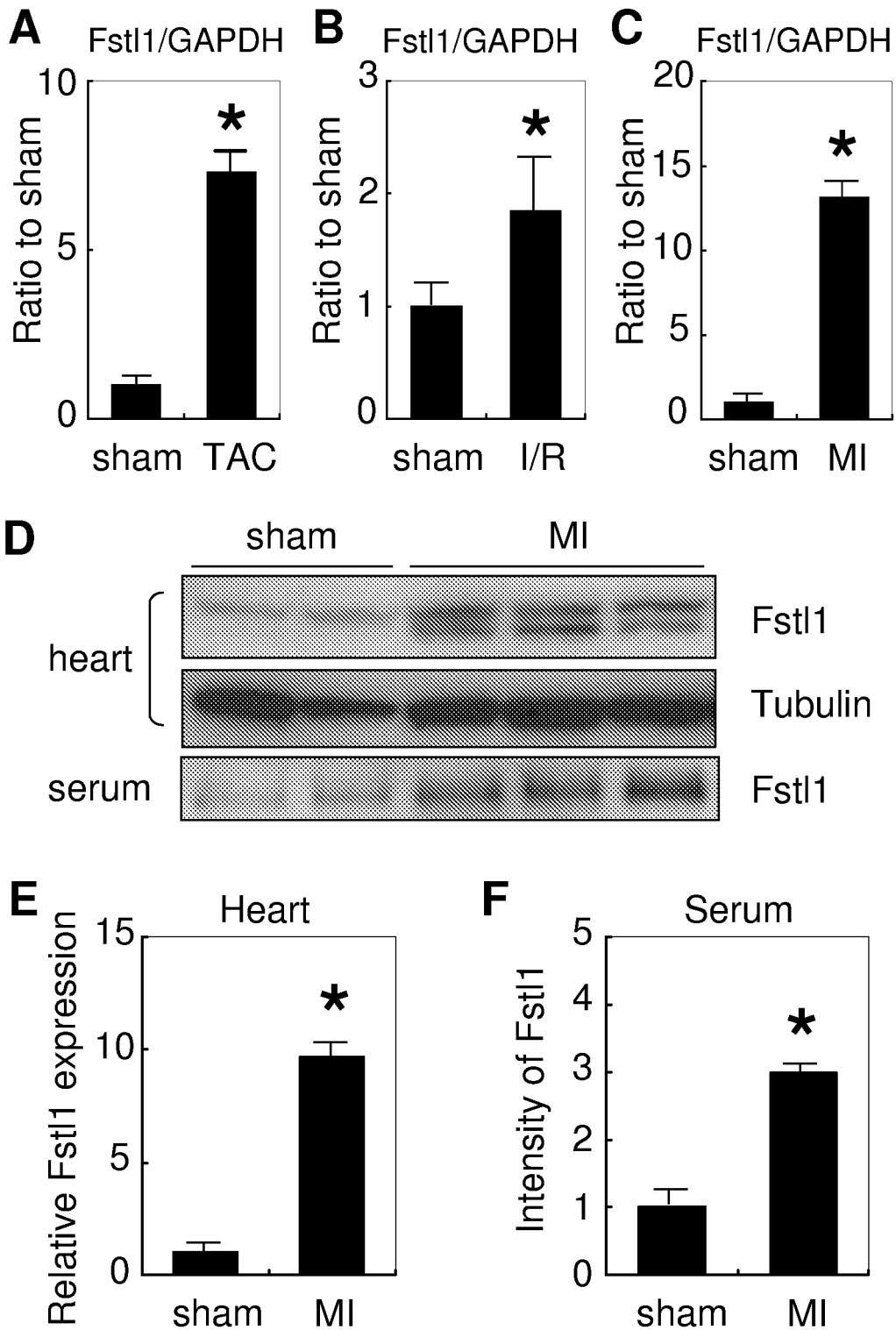
FIG. 1. Upregulation of Fstl1 by pathological stimuli in the heart. A-C, QRT-PCR analysis of Fstl1 transcript expression of Fstl1 mRNA after (A) transverse aortic constriction (TAC) (B) ischemia/reperfusion (YR) injury and (C) myocardial infarction (MI) resulting from permanent LAD ligation. The data are normalized to the intensity of the GAPDH signal, and are compared to Fstl1 transcript expression level in sham-operated heart. n=3-6. *P<0.05 vs. sham. D, Western immunoblot analysis of Fstll expression in mouse heart lysate and serum after sham operation (left 2 lanes) and myocardial infarction (right 4 lanes). E, Quantitation of Fstll protein expression in hearts of mice subjected to sham surgery or myocardial infarction. F, Quantitation of Fstll protein levels in serum of mice subjected to sham surgery or myocardial infarction.

Table 1 includes PCR primer sequences for GAPDH (SEQ ID NO: 3 and 4), Fstl-1 (SEQ ID NO: 5 and 6), Follistatin (SEQ ID NO: 7 and 8), Fstl-3 (SEQ ID NO: 9 and 10) and SPARC (SEQ ID NO: 11 and 12).

Table 2 includes data from quantitative RT-PCR for GAPDH, Fstl-1, Follistatin, Fstl-3 and SPARC expression.

Table 3 includes the amino acid (SEQ ID NO: 1) and polynucleotide (SEQ ID NO: 2) sequences of human Fstl-1 protein and a cDNA encoding it.

DETAILED DESCRIPTION

Described herein are the results of experiments designed to investigate the effect of Akt expression in a transgenic mouse model. It was discovered that Akt transgene activation upregulates expression of the secreted protein Fstl-1 in skeletal muscle and the heart. Fstl-1 is a member of the follistatin family of factors that bind to TGFβ family proteins. Transfection of Fstl-1 is reported to inhibit the proliferation and invasive behavior of cancer cell lines (Sumitomo K, et al. (2000) *Cancer Lett.* 155:37-46; Johnston I M, et al. (2000) *Oncogene.* 19:5348-5358., but prior to the studies described herein, the inventors were not aware of any functional studies on this factor in the heart, nor is there anything known about the regulation of metabolic processes by this factor. In studies following up on the discovery that Fstl-1 is regulated by Akt expression, it is demonstrated that Fstl-1 is a novel Akt-regulated molecule with metabolic and cardioprotective properties that suit it well for therapeutic use in cardiac and metabolic diseases or disorders.

The following describes Materials and Methods useful not only for the studies that elucidated the cardioprotective and metabolic effects of Fstl-1, but also for the practice of the invention as described herein.

Reagents

SYBR GREEN was purchased from Applied Biosystems. The plasmid vector, pcDNA3.1/V5-His was obtained from Invitrogen and adenoviral backbone plasmid pAdEasy-1 was from Qbiogene. Anti-HA antibody was purchased from Roche. Antibodies against Akt, ERK, phospho-Akt, phospho-mTOR, phospho-ERK and phospho-EGFR were purchased from Cell Signaling Technology. Anti-mouse Fstl-1 antibody was obtained from R&D Systems. Anti-phospho-FoxO1/3 antibody was from Upstate, antibody against alpha-tubulin was from Oncogene and anti-sarcomeric actin antibody was from Sigma. Dulbecco's modified Eagle's medium (DMEM) was purchased from Invitrogen. U0126 compound was from cell Signaling Technology, and LY294002 and AG1478 were from Calbiochem.

Cardiac-Specific Akt Transgenic Mice

The generation of cardiac-specific inducible myrAkt1 TG mice was described previously (Shiojima I, et al. (2005) *J Clin Invest.* 115:2108-2118). Briefly, two TG mice lines (Tet-myrAkt1 and alpha MHC-tTA) were mated to generate double transgenic mice (DTG). Treatment of DTG with 0.5 mg/ml doxycycline (DOX) inhibits tTA binding to tetO elements and results in repression of myrAkt1 gene expression. Without DOX treatment, tTA binds to tetO elements and induces myrAkt gene expression in the cardiac myocytes. For these studies, the Akt1 transgene was induced for 2 weeks by withdrawing DOX from the drinking water at the age of 12 wk.

Microarray Analysis

Microarray analysis were performed by Affymetrix Gene-Chip Mouse Expression Set 430 microarrays and normalized as described in a previous report (Schiekofer S, et al. (2006) *Physiol Genomics.* 27:156-170). Gene expression levels were compared before myr-Akt induction and those 2 wks after myr-Akt induction. Among transcripts that are upregulated by Akt activation, we selected transcripts which have full-length open reading frame cDNAs available in the NCBI web site. Amino acid sequences were then examined for signal sequences using Signal IP software. Transcripts with signal sequence were analyzed with SOSUI signal beta version software to predict transcripts with transmembrane domain.

RNA Isolation, Reverse Transcriptional PCR, and Quantitative Real-Time PCR

Total RNA from mouse heart samples were prepared by using RNA isolation kit (Qiagen) according to manufacture's protocols with treatment with DNase 1. Using 450 ng of total RNA, cDNA were synthesized with random hexamer primer by using ThermoScript RT-PCR Systems (Invitrogen) according to the manufacture's protocols. Quantitative Real-Time PCR (QRT-PCR) was performed on ABI-Prism 7900 using SYBR GREEN 1 as a double-stranded DNA-specific dye according to the manufacture's instruction (Applied Biosystems) (Schiekofer S, et al. (2006), supra). All primers used in this study were designed to be suitable for a single QRT-PCR thermal profile (95° C. for 10 min, and 50 cycles of 95° C. for 30 s and 60° C. for 1 min). The sequences are shown in Table 1. The expression levels of examined transcripts were compared to that of glyceraldehyde-3-phosphate dehydrogenase (GAPDH) and normalized to the mean value of controls.

Cloning and In Vitro Transfection Assay of Mouse Fstl-1

Full-length Fstl-1 cDNA was obtained by PCR and subcloned into pcDNA3.1/V5-His that express mouse Fstl-1 as a fusion to the V5 epitope at the C-terminus. To test the secretion of the gene product the plasmid vector pcDNA3.1/V5-His expressing Fstl-1 was transfected into HEK293 cells using Lipofectamin2000 (Invitrogen). After cells were incubated with serum free media for 24 hours, the cell lysate and media were collected. Cells were mock-transfected (no plasmid) as a negative control. The collected media was concentrated approximately ten fold by using Microcon (Millipore). Cell lysates and media were separated by SDS-PAGE and Fstl-1 fused with V5 was detected by Western blot analysis using anti-V5 antibody (Invitrogen).

Construction of Adenoviral Vector Expressing Mouse Fstl-1

Full-length mouse Fstl-1 cDNA was subcloned into an adenovirus shuttle vector. After linearization, shuttle vector was cotransformed into *E. coli* with the adenoviral backbone plasmid pAdEasy-1. The resultant recombinant adenoviral DNA with Fstl-1 cDNA was transfected into HEK 293 cells to produce the recombinant adenoviral vector. For some experiments, an adenoviral vector expressing β-galactosidase (Ad-β-gal) was used as a control. Adenoviral vectors were purified by CsCl ultracentrifugation.

Myocyte Cultures

Primary culture of neonatal rat ventricular myocytes (NRVCs) were prepared as described previously (Pimentel D R, et al. (2001) *Circ Res.* 89:453-460). After preparation, cells are incubated in Dulbecco's modified Eagle's medium (DMEM) supplemented with 7% Fetal Calf Serum (FCS). Eighteen to 24 hours after preparation, cells were transfected with adenoviral vector at a multiplicity of infection (MOI) of 50 in DMEM (supplemented with 1% of FCS) for 16 hours and incubated in DMEM without serum for more than 12 hours. Hypoxic conditions were generated using a GasPak system (Becton Dickinson) as described previously (Shibata R, et al. (2005) *Nat. Med.* 11:1096-1103). For hypoxia/reoxygenation studies, cells were exposed 12 hr hypoxia followed by 24 hr reoxygenation.

Western Blot Analysis

Heart tissue was homogenized in lysis buffer (Cell Signaling) containing 1 mM PMSF. The protein concentration was calculated using a BCA protein assay kit (Pierce). Cultured cells were lysed directly in lysis buffer. The cell and tissue lysates or culture media were added to equal volumes of 2× sample buffer (BioRad), and separated by SDS-PAGE. Proteins were transferred onto PVDF membrane (Amersham) and probed with the primary antibody followed by incubation with the HRP-conjugated secondary antibody. ECL plus system (Amersham) was used for detection of the protein signal. To quantify the expression level, the band intensities of Fstl-1 were corrected by those of alpha-tubulin by using Image J software.

TUNEL Staining

TUNEL staining for cultured cardiac myocytes was performed using the In Situ Cell Death detection kit (Roche) as described previously (Fujio Y, et al (2001) *Circulation.* 101: 660-667) with some modifications. In brief, cells are fixed by 4% paraformaldehyde in PBS, permeabilized with 0.1% Triton X-100 and incubated with anti-sarcomeric actinin antibody for 60 min followed by incubation with Cy3-conjugated anti-mouse IgG antibody. Cells were then incubated with TUNEL staining solution for 1 hr according to the manufacture's protocol. DAPI was used for nuclear staining. TUNEL staining for the frozen heart sections was performed as described previously (Fujio Y, et al (2001), supra) with some modifications. Cryo-sections (6 µm thickness) were fixed with 4% paraformaldehyde in PBS, permeabilized with 0.1% Triton X-100 and blocked with 6% skim milk. Anti-sarcomeric actin antibody was used for determination of myocytes followed by TUNEL and nuclear staining as described above. TUNEL positive myocytes were counted in randomly selected three fields of the slide and the experiments were repeated three times in duplicates.

Detection of Nucleosome Fragmentation by ELISA

Nucleosome fragmentation was assessed by ELISA using Cell Death Detection kit (Roche) according to the manufacture's protocol. Cardiac myocytes were seeded in 96-well plates, transfected with adenoviral vector and exposed to H/R. In one assay, 8 wells are used for one group and assays are repeated three times. The extent of nucleosome fragmentation of each group was expressed as relative value in comparison with the value of control group (Ad-beta-gal transfected cells without H/R).

Mouse Ischemia/Reperfusion Injury and Infarction Models and Evaluation of Infarction Size Eight week old male C57BL/6 mice (obtained from Charles River Laboratories) were intravenously injected through the jugular vein with adenovirus (Ad-Fstl-1 or Ad-β-gal, $1.0 \times 10^9$ p.f.u./mouse). Serum Fstl-1 was assayed by Western blot analysis five days after adenovirus delivery. At this time mouse ischemia/reperfusion injury was produced as described previously (Shibata R, et al. (2005), supra). Following anesthetization (pentobarbital 50 mg/kg i.p.) and intubation, the chest was exteriorized and 8-0 monofilament suture was ligated around the proximal left coronary artery (LCA) using a snare occluder. Ischemia followed by reperfusion was accomplished by tightening the snare occluder for 30 min and then loosing it. Myocardial reperfusion was confirmed by changes in ECG as well as by changes in appearance of the heart from pale to bright red. The suture was left in place and chest was closed. For mouse myocardial infarction model, the LCA was occluded by tight ligation without reperfusion. During the surgical procedure, the body temperature was monitored and maintained at 37+/−1° C. Twenty four hours after reperfusion, the chest was re-opened and the suture was re-tied. Evans Blue was injected at the aortic root to determine the area at risk (AAR). The heart was then excised and incubated with 2,3,5-triphenyltetrazolium chloride (TTC) for 5 min at 37° C. to determine the infarction area (IA). Left ventricular area (LVA), AAR and IA were determined by computerized planimetry using Image J (Bethesda, Md., USA).

Mouse Transverse Aortic Constriction Model

Mouse transverse aortic constriction model was performed as described previously (Shibata R, et al (2004) *Nat. Med.* 10:1384-1389). Following anesthetization (pentobarbital 50 mg/kg i.p.), the thoracic aorta was reached by dissecting intercostal muscle. The identified aorta was then tied with a 7-0 silk suture along with a 26-gauge blunt needle which was subsequently removed to produce a pressure gradient at the site.

Statistical Analysis

Data are presented as mean±SEM. Group differences were analyzed by two-tailed Student's t test or ANOVA. To compare multiple groups, Mann-Whitney U-test with Bonferroni correction was used. A value of $P<0.05$ was considered as statistically significant.

Methods of Treatment:

Metabolic Disease or Disorder:

Fstl-1 polypeptide or a portion thereof functional to restore normal metabolic regulation or at least modulate a metabolic disease or disorder at the term is used herein, can be administered to an individual in need thereof. In one approach, soluble Fstl-1 polypeptide, produced, for example, in cultured cells bearing a recombinant Fstl-1 expression vector can be administered to the individual. The Fstl-1 polypeptide or portion thereof will generally be administered intravenously. This approach rapidly delivers the protein throughout the system and maximizes the chance that the protein is intact when delivered. Alternatively, other routes of therapeutic protein administration are contemplated, such as by inhalation. Technologies for the administration of agents, including protein agents, as aerosols are well known and continue to advance. Alternatively, the polypeptide agent can be formulated in liposomes for topical delivery. Further contemplated are, for example, transdermal administration, and rectal or vaginal administration. Further options for the delivery of Fstl-1 polypeptides as described herein are discussed in the section "Pharmaceutical Compositions" herein below. Dosage ranges will vary, depending upon the individual, the degree of disease severity, and the specific polypeptide administered, but can be readily selected and adjusted by the administering clinician. An exemplary dose range is approximately 0.01 µg/kg to 1 mg/kg per dose, with doses administered, for example, once a week, once every three days, once every other day, or even daily. Initial doses can be greater, to establish an effect, and then reduced to a maintenance level thereafter.

For the treatment of metabolic diseases or disorders, an alternative to administration of polypeptide directly is to use cells that express and secrete the polypeptide. This approach provides potentially long-term delivery of the agent that also provides a steadier level than, for example, repeated bolus administration by injection. While it is not absolutely necessary, in a preferred embodiment, the cells can be autologous cells, taken from the patient to be treated, transfected or otherwise transduced with a transgene encoding the therapeutic polypeptide, and then re-introduced to the patient. Vectors for transduction of an Fstl-1-encoding sequence are well known in the art. While overexpression using a strong non-specific promoter, such as a CMV promoter, can be used, it can be helpful to include a tissue- or cell-type-specific promoter on the expression construct—for example, the use of a skeletal muscle-specific promoter or other cell-type-specific promoter can be advantageous, depending upon what cell type is used as a host.

Further, as described in the Examples herein, treatment can include the administration of viral vectors that drive the expression of Fstl-1 polypeptides in infected host cells. Viral vectors are well known to those skilled in the art and discussed further herein below. Other avenues for the administration of Fstl-1 polypeptides for therapy are discussed herein below—these can be applied to the treatment of metabolic disorders responsive to Fstl-1 polypeptides and to the cardioprotective aspect of the disclosed invention, among others.

Measures of Metabolic Function—Glucose Metabolism

Oral Glucose Tolerance Test

An oral glucose tolerance test can be performed in a doctor's office or a lab. it is performed on a fasting subject, i.e., having no food or drink except water for at least 10 hours but not greater than 16 hours. An initial blood sugar is drawn and then the subject is given a drink with a high amount of sugar in it (75 grams of glucose, or 100 grams for pregnant women). The subject then has their blood tested again 30 minutes, 1 hour, 2 hours and 3 hours after drinking the high glucose drink.

In a person without diabetes, the glucose levels in the blood rise following drinking the glucose drink, but then fall quickly back to normal—insulin is produced/released in response to the glucose, and the insulin has its normal effect of lowering blood glucose. In a diabetic, glucose levels rise higher than normal after drinking the glucose drink and come down to normal levels much slower—insulin is either not produced (type 1 diabetes), or it is produced but cells fail to respond to it (type 2 diabetes). As with fasting or random blood glucose tests, a markedly abnormal oral glucose tolerance test is diagnostic of diabetes. However, blood glucose measurements during the oral glucose tolerance test can vary somewhat. For this reason, if the test shows mildly elevated blood glucose levels, the clinical practitioner may repeat the test for further certainty in the diagnosis. Results in glucose tolerance tests and their interpretation are as follows:

Normal Response

A subject is said to have a normal response when the 2-hour glucose level is less than or equal to 110 mg/dl.

Impaired Fasting Glucose

When a subject has a fasting glucose equal to or greater than 110 and less than 126 mg/dl, they are said to have "impaired fasting glucose." This is considered a risk factor for future diabetes, but by itself, does not make the diagnosis of diabetes.

Impaired Glucose Tolerance

A subject is said to have "impaired glucose tolerance" when the 2-hour glucose results from the oral glucose tolerance test are greater than or equal to 140 but less than 200 mg/dl. This is also considered a risk factor for future diabetes. There has recently been discussion about lowering the upper value to 180 mg/dl to diagnose more mild diabetes to allow earlier intervention and hopefully prevention of diabetic complications.

Diabetes

A subject is diagnosed with diabetes when oral glucose tolerance tests show that the blood glucose level at 2 hours is equal to or more than 200 mg/dl. As noted above, there has recently been discussion about lowering the upper value to 180 mg/dl to diagnose more people with mild diabetes to permit earlier intervention and hopefully the prevention of diabetic complications.

An "improvement" in glucose tolerance and/or "treatment" of diabetes, as the terms are used herein, refer to a statistically significant reduction in either fasting glucose level (in a subject having "impaired fasting glucose"), or impaired glucose tolerance, or diabetes, at 2 hours post glucose administration. Alternatively, an at least 10% reduction in 2 hour blood glucose and/or a blood glucose in the normal range of less than or equal to 110 mg/dl are considered improvements and/or effective treatment as the terms are used herein.

Cardiac Injury and Other Ischemic Injury:

For the treatment or prevention of ischemic injury, such as cardiac ischemic or ischemia/reperfusion injury, soluble Fstl-1 polypeptide or a protective portion thereof as described herein can be administered to a subject in need thereof. Administration should commence as soon as possible following or during an ischemic event in order to have the best chance of benefit, but can also be beneficial at times thereafter. The administration can be by the same pathways as described above for metabolic therapies. However, intravenous administration or even localized cardiac administration can be advantageous. Due to the acute nature of the ischemic event, effective treatment of cardiac or other tissue for ischemic injury is not likely to require prolonged administration, although this is not ruled out for potential preventive benefit. Also, the dosages likely to be effective can be similar to those discussed above for metabolic regulation, but it is also contemplated that much higher dosages can be initially administered to fully establish a cardioprotective effect before the damage becomes too extensive.

It is noted that Fstl-1 has been suggested to be involved in the pathologies of some disorders, including, for example, autoimmune arthritic disorders. It is contemplated that anti-inflammatories or immunosuppressive agents can be concurrently administered if necessary to counteract such systemic effects in cardiac patients receiving Fstl-1 therapy.

Administration of a viral vector is demonstrated in a mouse model herein. Viral vectors can also be employed in humans for cardioprotective therapy if so desired—an advantage is the fairly rapid production and secretion of large amounts of the recombinant protein in vivo.

Measurement of Cardiac Muscle Injury

Generally, although cardiac muscle biopsy would likely indicate the status of cardiac muscle after a treatment, such an invasive and potentially further-destructive approach in an individual with ischemic injury to the heart is clearly not warranted to monitor the effects of cardiac protective treatments as described herein. Instead, the efficacy of cardiac protection or therapy according to the methods described herein can be evaluated by following surrogate or indirect markers of cardiac health and function. For example, cardiac cell death, whether by necrosis or apoptosis, is generally accompanied by the release of cardiac enzymes, including cardiac creatine kinase (CK). Assays for cardiac enzymes are routinely used in the diagnosis of myocardial infarction and can be used to monitor the efficacy of cardiac protection according to the methods described herein. A decrease in cardiac enzymes (e.g., a 10% or greater decrease), or a lower level than is normally seen with an infarct of a given size, is indicative of effective treatment. Other markers include, for example, cardiac Troponin T (TnT), which is a marker of cardiac injury that is used as an alternative for CK. In addition, one can perform "echocardiographic analysis of ejection fraction" as a measure of cardiac injury, stabilization after injury or recovery after injury.

Of course, another marker of the efficacy of cardioprotective intervention as described herein is survival. Statistical survival rates for myocardial ischemic events are well established—when an individual or group of individuals treated according to the methods described herein survives beyond the expected time or at a greater than expected rate for an infarct of a given size and location, the treatment can be considered effective.

Vectors and Expression:

Expression vectors compatible with eukaryotic cells, preferably those compatible with vertebrate cells, can be used to produce recombinant constructs for the expression of Fstl-1 or portions or derivatives thereof as described herein. Eukaryotic cell expression vectors are well known in the art and are available from several commercial sources. Typically, such vectors are provided containing convenient restriction sites for insertion of the desired DNA segment. These vectors can be viral vectors such as adenovirus, adeno-associated virus, pox virus such as an *orthopox* (vaccinia and attenuated vaccinia), avipox, lentivirus, murine moloney leukemia virus, etc. Alternatively, plasmid expression vectors can be used.

Viral vector systems which can be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an *orthopox*, e.g., vaccinia virus vectors or avipox, e.g. canary pox or fowl pox; and (j) a helper-dependent or gutless adenovirus. In a preferred embodiment, the vector is an adenovirus. Replication-defective viruses can also be advantageous.

The vector may or may not be incorporated into the cells genome. The constructs may include viral sequences for transfection, if desired. Alternatively, the construct may be incorporated into vectors capable of episomal replication, e.g EPV and EBV vectors.

Constructs for the recombinant expression of Fstl-1 will generally require regulatory elements, e.g., promoters, enhancers, etc., to ensure the expression of the construct in target cells. Other specifics for vectors and constructs are described in further detail below.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. In some embodiments, it can be advantageous to direct expression of a Fstl-1 polypeptide in a tissue-or cell-specific manner. Cardiac-specific expression can be achieved, for example, using the cardiac NCX1 promoter (Nicholas et al., 1998, Am. J. Physiol. Heart Circ. Physiol. 274: H217-H232), the cardiac myosin light chain 2 promoter (Griscelli et al., 1998, Hum. Gene Ther. 9: 1919-1928) or other cardiac-specific promoter known in the art.

In a specific embodiment, viral vectors that contain nucleic acid sequences encoding the human Fstl-1 polypeptide or portions or variants thereof are used. For example, a retroviral vector can be used (see Miller et al., Meth. Enzymol. 217: 581-599 (1993)). These retroviral vectors contain the components necessary for the correct packaging of the viral genome and integration into the host cell DNA. The nucleic acid sequences encoding a human Fstl-1 polypeptide are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

The production of a recombinant retroviral vector carrying a gene of interest is typically achieved in two stages. First, sequence encoding an Fstl-1 polypeptide can be inserted into a retroviral vector which contains the sequences necessary for the efficient expression of the metabolic regulators (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3[prime] regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant retroviral vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Another preferred viral vector is a pox virus such as a vaccinia virus, for example an attenuated vaccinia such as Modified Virus Ankara (MVA) or NYVAC, an avipox such as fowl pox or canary pox. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In another embodiment, lentiviral vectors are used, such as the HIV based vectors described in U.S. Pat. Nos. 6,143,520; 5,665,557; and 5,981,276, which are herein incorporated by reference.

Use of Adeno-associated virus (AAV) vectors is also contemplated (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

U.S. Pat. No. 5,676,954 (which is herein incorporated by reference) reports on the injection of genetic material, complexed with cationic liposome carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals. Such cationic lipid complexes or nanoparticles can also be used to deliver protein.

A gene or nucleic acid sequence can be introduced into a target cell by any suitable method. For example, an Fstl-1 construct can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding an Fstl-1 polypeptide can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a gene or nucleic acid sequence encoding an Fstl-1 polypeptide can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999)).

Methods known in the art for the therapeutic delivery of agents such as proteins and/or nucleic acids can be used for the delivery of a polypeptide or nucleic acid encoding an Fstl-1 polypeptide for modulating a metabolic function or for cardioprotection in a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to directly administer therapeutic polypeptides, e.g., encapsulation in liposomes, microparticles, microcapsules, recombinant cells capable of expressing the compound, and receptor-mediated endocytosis (see, e.g., Wu and Wu, 1987, J. Biol. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked Fstl-1 encoding nucleic acid segment into the selected expression/delivery vector, many equivalent vectors for the practice of the methods described herein can be generated.

It will be appreciated by those of skill that cloned genes readily can be manipulated to alter the amino acid sequence of a protein. The cloned gene for Fstl-1 can be manipulated by a variety of well known techniques for in vitro mutagenesis, among others, to produce variants of the naturally occurring human protein, herein referred to as muteins or variants or mutants of Fstl-1, which may be used in accordance with the methods and compositions described herein.

The variation in primary structure of muteins of Fstl-1 useful in the invention, for instance, may include deletions, additions and substitutions. The substitutions may be conservative or non-conservative. The differences between the natural protein and the mutein generally conserve desired properties, mitigate or eliminate undesired properties and add desired or new properties.

The Fstl-1 polypeptide can also be a fusion polypeptide, fused, for example, to a polypeptide that targets the product to a desired location, or, for example, a tag that facilitates its purification, if so desired. Fusion to a polypeptide sequence that increases the stability of the Fstl-1 polypeptide is also contemplated. For example, fusion to a serum protein, e.g., serum albumin, can increase the circulating half-life of a Fstl-1 polypeptide. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

In another aspect, biodegradable or absorbable polymers can provide extended, often localized, release of polypeptide agents. The potential benefits of an increased half-life or extended release for a therapeutic agent are clear. A potential benefit of localized release is the ability to achieve much higher localized dosages or concentrations, for greater lengths of time, relative to broader systemic administration, with the potential to also avoid possible undesirable side effects that may occur with systemic administration.

Bioabsorbable polymeric matrix suitable for delivery of Fstl-1 polypeptides can be selected from a variety of synthetic bioabsorbable polymers, which are described extensively in the literature. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563, among others, and in "Biomedical Polymers" edited by S. W. Shalaby, Carl Hanser Verlag, Munich, Vienna, N.Y., 1994 and in many references cited in the above publications. The particular bioabsorbable polymer that should be selected will depend upon the particular patient that is being treated.

Pharmaceutical Compositions

The present invention provides therapeutic compositions useful for practicing the therapeutic methods described herein. Therapeutic compositions of the present invention contain a physiologically tolerable carrier together with an Fstl-1 polypeptide or a vector capable of expressing an Fstl-1 polypeptide as described herein, dissolved or dispersed therein as an active ingredient. In a preferred embodiment, the therapeutic composition is not immunogenic when administered to a mammal or human patient for therapeutic purposes.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution or suspension in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. In addition, if desired, the composition can contain minor amounts of auxiliary substances such as wetting or emulsifying agents, pH buffering agents and the like which enhance the effectiveness of the active ingredient.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

For topical application, the carrier may be in the form of, for example, and not by way of limitation, an ointment, cream, gel, paste, foam, aerosol, suppository, pad or gelled stick.

The amount of the active Fstl-1 polypeptide that will be effective in the treatment of a particular disorder or condition will depend on the nature of the disorder or condition, and can be determined by standard clinical techniques. In addition, assays such as those discussed herein may optionally be employed to help identify optimal dosage ranges.

The precise dose to be employed in the formulation will also depend on the route of administration, and the seriousness of the disease or disorder, and should be decided according to the judgment of the practitioner and each subject's circumstances. Suitable dosage ranges for administration of agents are generally about 0.01 µg/kg body weight to 1.0 mg/kg body weight. In some embodiments, the suitable range for administration is 5 µg/kg body weight to 30 µg/kg body weight. Effective doses may be extrapolated from dose-response curves derived from in vitro or animal model test bioassays or systems.

The route of administration can be any route known to persons skilled in the art, for example but not limited to parenteral, including intravenous and intraarterial administration, intrathecal administration, intraventricular administration, intraparenchymal, intracranial, intracisternal, intrastriatal, and intranigral administration.

The invention also contemplates an article of manufacture which is a labeled container for providing an Fstl-1 polypeptide. An article of manufacture comprises packaging material and a pharmaceutical agent contained within the packaging material.

The pharmaceutical agent in an article of manufacture is any of the compositions of the present invention suitable for providing an Fstl-1 polypeptide and formulated into a pharmaceutically acceptable form as described herein according to the disclosed indications. Thus, the composition can comprise an Fstl-1 polypeptide or a DNA molecule which is capable of expressing the polypeptide.

The article of manufacture contains an amount of pharmaceutical agent sufficient for use in treating a condition indicated herein, either in unit or multiple dosages. The packaging material comprises a label which indicates the use of the pharmaceutical agent contained therein, e.g., for the treatment of a metabolic disorder, for cardioprotection, or for other indicated therapeutic or prophylactic uses.

The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

The articles "a" and "an" are used herein to refer to one or to more than one (i.e., to at least one) of the grammatical object of the article. By way of example, "an element" means one element or more than one element.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. Use of a follistatin-like protein 1 polypeptide or a protective portion thereof, in the preparation of a medicament for the treatment of ischemic injury.
2. The use of paragraph 1, wherein the ischemic injury comprises an ischemic limb disease.
3. The use of paragraph 1 or 2, the ischemic injury occurs in a mammal suffering from diabetes, or atherosclerosis.
4. The use of any one of the preceding paragraphs wherein the ischemic injury comprises myocardial ischemia or myocardial ischemia/reperfusion injury.
5. The use of any one of the preceding paragraphs wherein the medicament promotes endothelial cell growth, survival and/or differentiation.
6. Use of a follistatin-like protein 1 polypeptide or a protective portion thereof, for the treatment of ischemic injury.
7. The use of paragraph 6, wherein the ischemic injury comprises an ischemic limb disease.
8. The use of paragraph 6 or 7, the ischemic injury occurs in a mammal suffering from diabetes, or atherosclerosis.
9. The use of any one of the preceding paragraphs wherein the ischemic injury comprises myocardial ischemia or myocardial ischemia/reperfusion injury.
10. The use of any one of the preceding paragraphs wherein the use promotes endothelial cell growth, survival and/or differentiation.
11. Use of a follistatin-like protein 1 polypeptide or a protective portion thereof for preventing cardiac apoptosis.
12. The use of paragraph 11 wherein the apoptosis is induced by ischemia or ischemia/reperfusion.
13. The use of paragraph 11 or 12, wherein the follistatin-like protein 1 comprises a soluble follistatin-like protein 1 polypeptide or a protective portion thereof.
14. The use of any one of the preceding paragraphs wherein the follistatin-like protein 1 polypeptide is comprised by a vector encoding the follistatin-like protein 1 polypeptide.
15. The use of paragraph 14, wherein the vector is selected from the group consisting of an adenovirus vector, a poxvirus vector, and a lentiviral vector.
16. Use of a follistatin-like protein 1 polypeptide or a portion thereof to modify glucose metabolism in an individual.
17. The use of paragraph 16, wherein the individual is diabetic.
18. The use of paragraph 16 or 17, wherein modifying glucose metabolism comprises improved glucose tolerance.
19. The use of any one of the preceding paragraphs, wherein the follistatin-like protein 1 comprises a soluble follistatin-like protein 1 polypeptide or a protective portion thereof.
20. The use of any one of the preceding paragraphs wherein the follistatin-like protein 1 polypeptide is comprised by a vector encoding the follistatin-like protein 1 polypeptide.
21. The use of paragraph 20, wherein the vector is selected from the group consisting of an adenovirus vector, a poxvirus vector, and a lentiviral vector.
22. Use of a follistatin-like protein 1 polypeptide or a protective portion thereof for the treatment of diabetes.
23. The use of paragraph 22, wherein the follistatin-like protein 1 comprises a soluble follistatin-like protein 1 polypeptide or a protective portion thereof.
24. The use of paragraph 22 or 23, wherein the follistatin-like protein 1 polypeptide is comprised by a vector encoding the follistatin-like protein 1 polypeptide.
25. The use of paragraph 24, wherein the vector is selected from the group consisting of an adenovirus vector, a poxvirus vector, and a lentiviral vector.
26. Use of a follistatin-like protein 1 polypeptide or a protective portion thereof for promoting revascularization of ischemic tissue.
27. The use of paragraph 26, wherein the ischemic tissue is muscle.

28. The use of paragraph 26 or 27, wherein the ischemic tissue is cardiac or skeletal muscle.
29. The use of any one of the preceding paragraphs wherein the use promotes endothelial cell growth, survival and/or differentiation.
30. Use of a follistatin-like protein 1 polypeptide or a protective portion thereof for increasing angiogenesis in an ischemic tissue.
31. The use of paragraph 30, wherein the ischemic tissue is muscle.
32. The use of paragraph 30 or 31, wherein the ischemic tissue is cardiac or skeletal muscle.
33. The use of any one of the preceding paragraphs wherein the use promotes endothelial cell growth, survival and/or differentiation.
34. Use of a follistatin-like protein 1 polypeptide or a protective portion thereof for preventing or reducing endothelial cell apoptosis in an ischemic tissue.
35. The use of paragraph 34, wherein the tissue is muscle.
36. The use of paragraph 34 or 35, wherein the muscle is cardiac or skeletal muscle.
37. The use of any one of the preceding paragraphs wherein the use promotes endothelial cell growth, survival and/or differentiation.
38. A method of treating or preventing ischemic injury in a mammal, the method comprising administering a follistatin-like protein 1 polypeptide or a protective portion thereof to a mammal in need thereof, wherein the administering treats or prevents ischemic injury.
39. The method of paragraph 38 wherein the ischemic injury comprises ischemia/reperfusion injury.
40. The method of paragraph 38 or 39, wherein the ischemic injury is ischemic injury of cardiac muscle.
41. The method of any one of the preceding paragraphs, wherein the administering comprises administering a soluble follistatin-like protein 1 polypeptide or a protective portion thereof.
42. The method of any one of the preceding paragraphs, wherein the administering comprises administering a vector encoding the follistatin-like protein 1 polypeptide or protective portion thereof.
43. The method of paragraph 42, wherein the vector is a viral vector or a plasmid vector.
44. The method of paragraph 42 or 43, wherein the viral vector is selected from the group consisting of an adenovirus vector, a poxvirus vector, and a lentiviral vector.
45. A method of preventing apoptosis in cardiac tissue, the method comprising administering to a mammal in need thereof a follistatin-like protein 1 or a protective portion thereof, wherein the administering prevents apoptosis in cardiac tissue of the mammal.
46. The method of paragraph 45 wherein the apoptosis is induced by ischemia or ischemia/reperfusion.
47. The method of paragraph 45 or 46, wherein the administering comprises administering a soluble follistatin-like protein 1 polypeptide or a protective portion thereof.
48. The method of any one of the preceding paragraphs wherein administering comprises administering a vector encoding the follistatin-like protein 1 polypeptide or a protective portion thereof.
49. The method of paragraph 48 wherein the vector is a viral vector or a plasmid vector.
50. The method of paragraph 48 or 49 wherein the viral vector is selected from the group consisting of an adenovirus vector, a poxvirus vector, and a lentiviral vector.
51. A method of preventing or reducing apoptosis in cardiac tissue, the method comprising the steps of determining if an individual displays one or more symptoms or indicators for diabetes, and if so, administering an Fstl-1 polypeptide or a prophylactically or therapeutically effective portion thereof, in an amount effective to prevent or reduce apoptosis in cardiac tissue.
52. A method of modifying glucose metabolism in an individual in need thereof, the method comprising administering a follistatin-like protein 1 polypeptide or a portion thereof effective to modify glucose metabolism to a mammal in need thereof, wherein the administering modifies glucose metabolism in the individual.
53. The method of paragraph 52 wherein the individual is diabetic.
54. The method of paragraph 52 or 53 wherein the modification of the glucose metabolism comprises improved glucose tolerance.
55. The method of any one of the preceding paragraphs wherein the administering comprises administering a soluble follistatin-like protein 1 polypeptide or a protective portion thereof.
56. The method of any one of the preceding paragraphs wherein the administering comprises administering a vector encoding the follistatin-like protein 1 polypeptide or protective portion thereof.
57. The method of paragraph 56 wherein the vector is a viral vector or a plasmid vector.
58. The method of paragraph 56 or 57 wherein the viral vector is selected from the group consisting of an adenovirus vector, a poxvirus vector, and a lentiviral vector.
59. A method of treating diabetes in an individual in need thereof, the method comprising administering a follistatin-like protein 1 polypeptide, or a portion thereof effective to modify glucose metabolism, to a mammal in need thereof, wherein the administering improves glucose tolerance in the individual.
60. The method of paragraph 59 wherein the administering comprises administering a soluble follistatin-like protein 1 polypeptide or a protective portion thereof.
61. The method of paragraph 59 or 60 wherein the administering comprises administering a vector encoding the follistatin-like protein 1 polypeptide or protective portion thereof.
62. The method of paragraph 61 wherein the vector is a viral vector is a plasmid vector.
63. The method of paragraph 61 or 62 wherein the viral vector is selected from the group consisting of an adenovirus vector, a poxvirus vector, and a lentiviral vector.
64. A viral vector comprising nucleic acid sequence encoding a follistatin-like protein 1 polypeptide or a portion thereof effective for the treatment or prevention of ischemia/reperfusion injury.
65. The viral vector of paragraph 64 wherein the viral vector is a vector selected from the group consisting of an adenoviral vector, a poxvirus vector, and a lentiviral vector.
66. The viral vector of paragraph 64 or 65 wherein the nucleic acid sequence encoding a follistatin-like protein 1 polypeptide or a portion thereof is operatively linked to a tissue- or cell-type-specific promoter.
67. The viral vector of any one of the preceding paragraphs wherein the tissue- or cell-type specific promoter comprises a skeletal or cardiac muscle-specific promoter.
68. A pharmaceutical composition comprising a vector of paragraph 27 and a pharmaceutically acceptable carrier.
69. A method of promoting revascularization of ischemic tissue, the method comprising administering to a mammal in need thereof a follistatin-like protein 1 polypeptide or a portion thereof sufficient to activate Akt-1 signaling activity, wherein the administering promotes increased blood flow in the tissue.
70. The method of paragraph 69, wherein the tissue is muscle.
71. The method of paragraph 69 or 70, wherein the muscle is cardiac or skeletal muscle.
72. The method of any one of the preceding paragraphs wherein the administering promotes endothelial cell growth, survival and/or differentiation.
73. The method of any one of the preceding paragraphs, wherein the mammal suffers from an ischemic limb disease.
74. The method of any one of the preceding paragraphs, wherein the mammal suffers from diabetes, or atherosclerosis.
75. A method of increasing angiogenesis in an ischemic tissue, the method comprising administering to a mammal in need thereof a follistatin-like protein 1 polypeptide or a portion thereof sufficient to activate Akt-1 signaling activity, wherein the administering promotes angiogenesis in an ischemic tissue of the mammal.
76. The method of paragraph 75, wherein the tissue is muscle.
77. The method of paragraph 75 or 76, wherein the muscle is cardiac or skeletal muscle.
78. The method of any one of the preceding paragraphs wherein the administering promotes endothelial cell growth, survival and/or differentiation.
79. The method of any one of the preceding paragraphs, wherein the mammal suffers from an ischemic limb disease.
80. The method of any one of the preceding paragraphs, wherein the mammal suffers from diabetes, or atherosclerosis.
81. A method of preventing or reducing apoptosis of endothelial cells in an ischemic tissue, the method comprising administering to a mammal in need thereof a follistatin-like protein 1 polypeptide or a portion thereof sufficient to activate Akt-1 signaling activity, wherein the administering prevents or reduces apoptosis of endothelial cells of an ischemic tissue of the mammal.
82. The method of paragraph 81, wherein the tissue is muscle.
83. The method of paragraph 81 or 82, wherein the muscle is cardiac or skeletal muscle.
84. The method of any one of the preceding paragraphs wherein the administering promotes endothelial cell growth, survival and/or differentiation.
85. The method of any one of the preceding paragraphs, wherein the mammal suffers from an ischemic limb disease.
86. The method of any one of the preceding paragraphs, wherein the mammal suffers from diabetes, or atherosclerosis.

EXAMPLES

Example 1

FSTL-1 and Cardiac Ischemia/Reperfusion Injury

Using an inducible Akt1 transgenic mouse model, the inventors have found that Follistatin like-1 (Fstl-1) expression is significantly increased by Akt activation in skeletal muscle. Adenovirus-mediated overexpression of Fstl-1 (Ad-Fstl-1) activated AMPK signaling and induced PGC-1α and Glut4 expression in C2C12 skeletal muscle cell cultures and in mouse gastrocnemius muscle. To examine the effects of Fstl-1 on metabolism in vivo, Ad-Fstl-1 was delivered systemically to mice fed a high fat/high sucrose diet. Ad-Fstl-1 activated AMPK signaling in liver and reduced circulating levels of insulin. The delivery of Ad-Fstl-1 to obese ob/ob mice improved their response in a glucose tolerance test. These results indicate that Fstl-1 is a metabolic regulatory protein that is secreted from skeletal muscle. The Fstl-1 polypeptide and portions or derivatives thereof can have therapeutic utility for the treatment of diabetes and metabolic syndrome.

Fstl-1 transcripts were also upregulated in response to myocardial stresses including transverse aortic constriction, ischemia-reperfusion injury and myocardial infarction. Adenovirus-mediated overexpression of Fstl-1 protected cultured neonatal rat ventricular myocytes from hypoxia-/reoxygenation-induced apoptosis. The intravenous administration of an adenoviral vector encoding Fstl-1 to mice resulted in a reduction in myocardial infarct size following ischemia-reperfusion injury that was accompanied by a reduction in apoptosis in the heart. These results indicate that Fstl-1 functions as an anti-apoptotic protein and can play a role in myocardial maintenance in response to harmful stimuli.

Example 1a

Fstl-1 Upregulation by Akt Activation in the Heart

Microarray gene expression analysis was compared between control mouse hearts and in hearts of mice two weeks after myocardial induction of myristoylated Akt (Schiekofer S, et al (2006), supra). Transcripts upregulated by 2 wks Akt activation with full-length open reading frame cDNAs were selected. amino acid sequences were then examined for signal sequences using Signal IP software. Transcripts with signal sequence were further analyzed with SOSUI signal beta version software to predict transcripts encoding a protein with a transmembrane domain. Akt-regulated transcripts were identified that contained a predicted signal sequence but lacked a transmembrane domain. Of this subset of proteins, follistatin like-1 (Fstl-1) was selected for further analysis. To confirm the changes in Fstl-1 mRNA level, QRT-PCR was performed using specific primer sets for Fstl-1 and normalizing the signal to that of GAPDH (Table 2). Fstl-1 was significantly upregulated by Akt activation in the heart, but transcripts encoding other proteins containing the follistatin domain, including follistatin, follistatin like-3 and SPARC, were not regulated by Akt activation (Table 2).

To better understand the regulation of Fstl-1 in cardiac cells, transcript levels of this factor were measured by RT-PCR in hearts that were subjected to various injuries. Fstl-1 transcript was upregulated approximately 7-fold 7 days following transverse aortic constriction that induces pressure overload hypertrophy (FIG. 1a), approximately 2-fold in the myocardial area at risk 1 day following ischemia-reperfusion injury (FIG. 1b) and approximately 13-fold in hearts 3 days following permanent LAD ligation (FIG. 1c). Fstl-1 protein level increased after MI by Western blot analysis both in the heart and serum (FIG. 1d). Thus Fstl-1 expression is induced by a variety of stresses in the heart.

Figure 2:
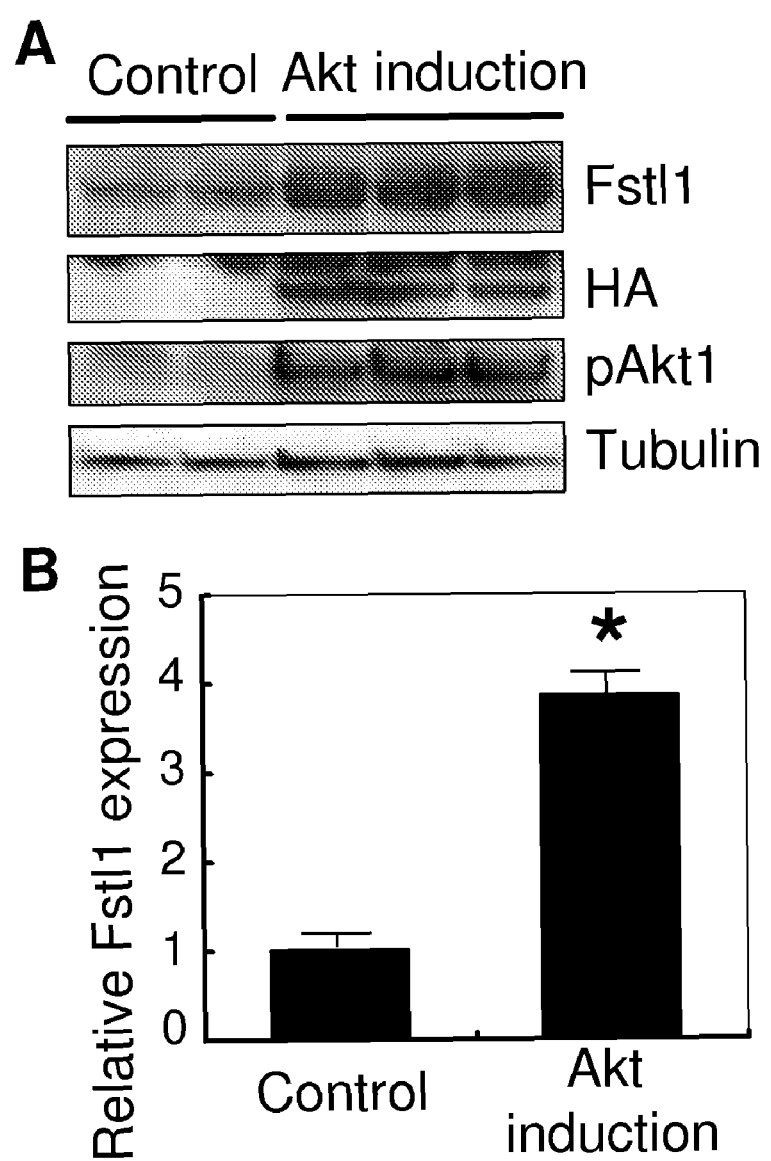
FIG. 2. Upregulation of Fstl1 in Akt-activated heart. A, Western blots from transgenic mouse heart lysate. Transgene (myr-Akt tagged with HA) induction was confirmed by probing with antibody against HA (middle panel). Two weeks after myr-Akt transgene induction (lane 3, 4 and 5), Fstl1 expression level was upregulated (upper panel) compared to control mice that undergo the same Dox administration/withdrawal protocol (lanes 1 and 2). Each lane represents a difference transgenic or control mouse. B, Quantification of the intensity of the bands for Fstl1 normalized with that for alpha-tubulin. n=3-4. *P<0.05.

To assess the Akt-mediated change in Fstl-1 protein expression in the heart, Western blot analysis was performed. FIG. 2 shows blots from two control hearts and three Akt transgenic hearts following two weeks of induction. The hemagglutinin (HA) transgene product was detected by anti-HA antibody and Akt activation was confirmed by phospho-specific anti-Akt antibody (FIG. 2a). After normalization to the alpha-tubulin signal, Fstl-1 protein expression was significantly induced by Akt activation in the heart (FIG. 2b).

Example 1b

Figure 3:
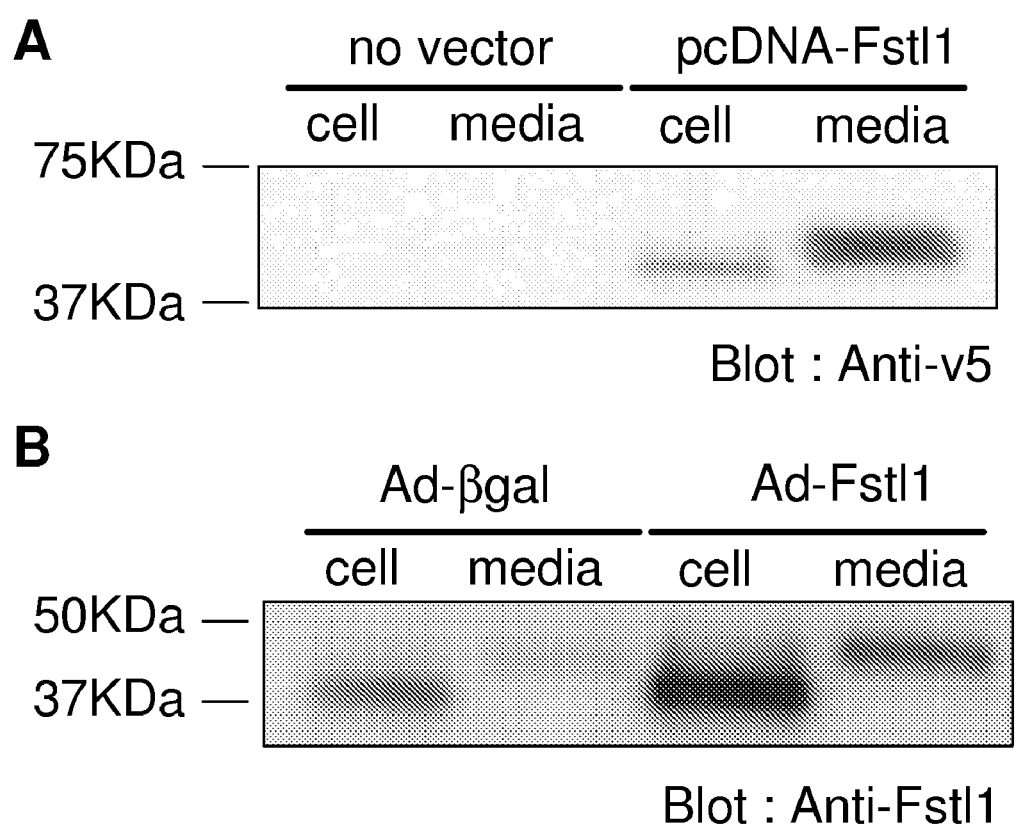
FIG. 3. Fstl1 is secreted from cells. A, HEK293 cells were transfected with a plasmid expressing V5 epitope-tagged Fstl1 protein. Western blot analysis using anti-V5 antibody indicates that Fstl1 is present in the cell pellet and the culture media. B, NRVMs were transfected with an adenovirus expressing Fstl1 or β-galactosidase. Western blot analysis using anti-Fstl1 antibody revealed Fstl1 protein expression in the cell pellet and the culture media, and the intensity of these bands increased in cells that were transduced with Ad-Fstl1.

Fstl-1 is a Secreted Protein that Activates Akt and Erk Signaling in Myocytes Plasmid and adenovirus expression vectors were constructed to assess the functional significance of increased Fstl-1 expression in the heart. Using cDNA from Akt transgenic heart, mouse Fstl-1 was subcloned into the pcDNA3.1/V5-His expression vector. The vector was transfected into HEK293 cells, and cells were incubated with serum free media for 24 hours. As shown in FIG. 3a, Fstl-1 was detected in the media indicating that it is a secreted protein.

To study Fstl-1 expression in cardiac myocytes, an adenoviral expression vector was constructed and tested. Neonatal rat ventricular cardiomyocytes (NRVCs) were transduced with Ad-Fstl-1 or Ad-βgal as a control. Recombinant Fstl-1 protein was detected in the cell pellet and the media as well as endogenous Fstl-1 as detected in cells transduced with Ad-βgal (FIG. 3b). As with the plasmid-encoded Fstl produced by HEK293 cells, the protein detected in the NRVC media exhibited a reduced electrophoretic mobility indicating that the secreted protein is post-translationally modified.

Example 1c

Fstl-1 Upregulation by Akt in Skeletal Muscle

Figure 4:
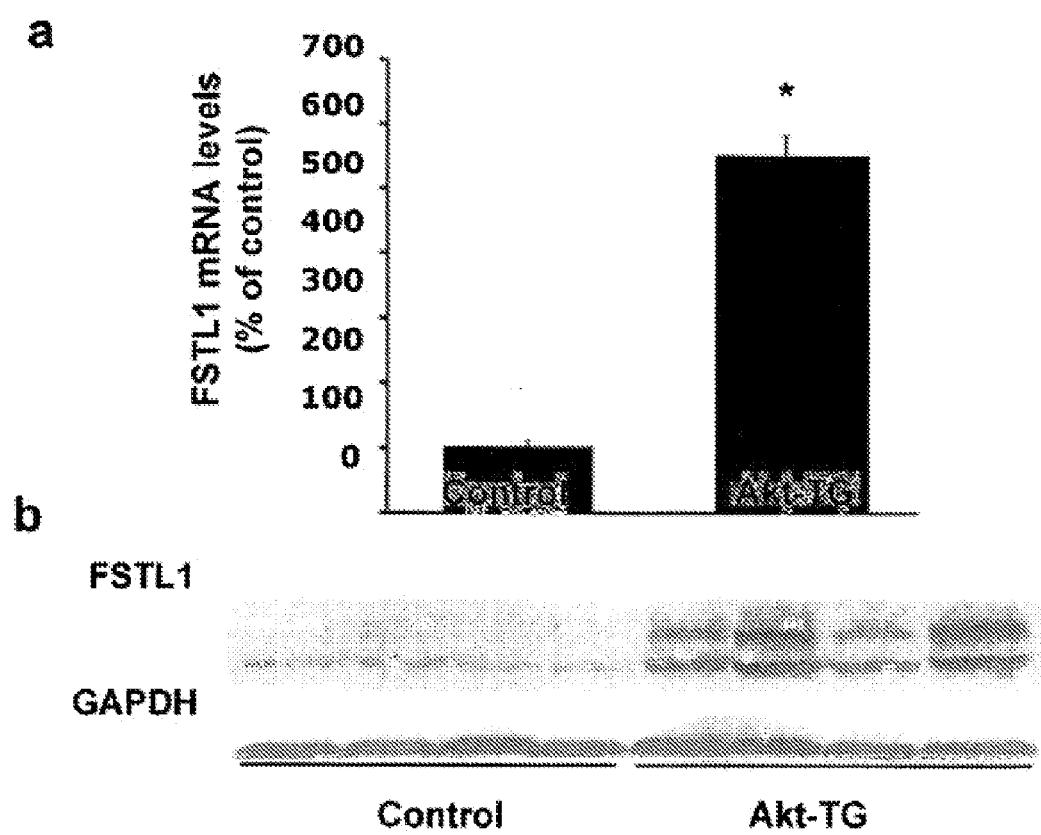
FIG. 4. Increased expression of Fstl-1 in Akt-activated skeletal muscle. a, Fstl-1 mRNA levels in skeletal muscles of wild-type (Control) and skeletal muscle-specific Akt-transgenic (Akt-TG) mice at 2 weeks after myr-Akt transgene induction (n=4-5). Fstl-1 mRNA levels were quantified by real time (RT)-PCR analysis. *P<0.01 vs. control. b, Fstl-1 protein levels in skeletal muscles of wild-type (Control) and Akt-TG mice at 2 weeks after Akt activation (n=4). Fstl-1 and GAPDH protein levels were determined by Western blot analysis.
Figure 5:
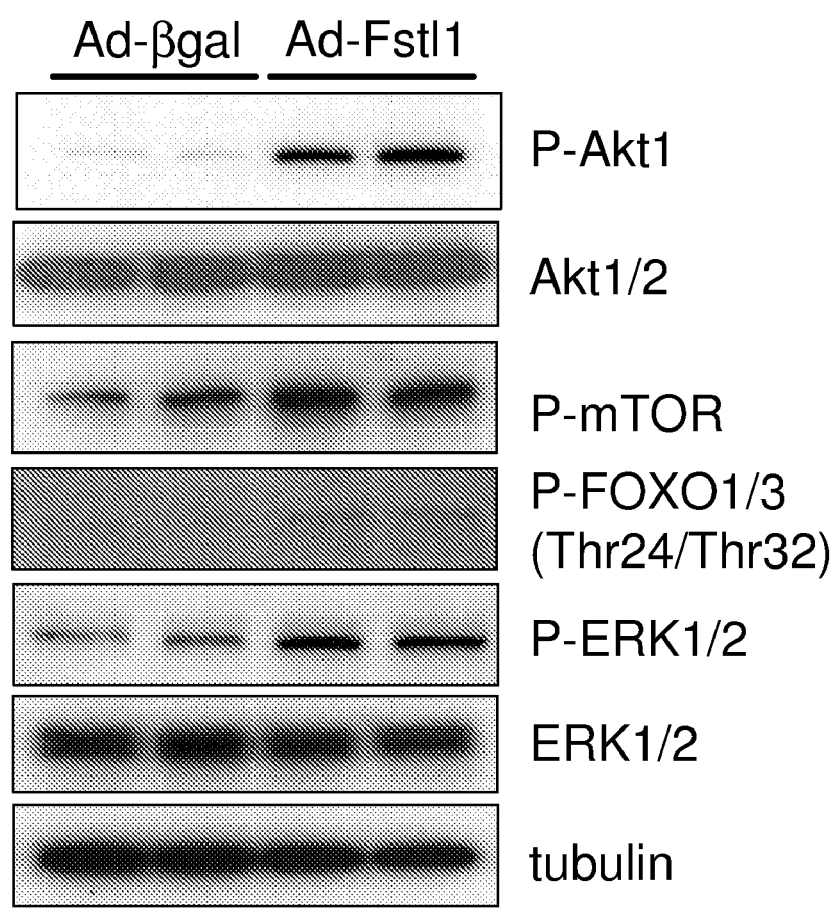
FIG. 5. Activation of intracellular signaling pathways by Fstl1. After transfection of Ad-Fstl1, NRVMs were cultured for 36 hours and cell lysates were prepared for Western blot analysis. Transduction of Ad-Fstl1 led to the activating phosphorylation of Akt1 and 2 and ERK1/2 in NRVMs. Phosphorylation of FOXO1 and 3 and mTOR, downstream targets of Akt signaling, also increased.

FSTL-1 expression was compared in skeletal muscle between control mouse and conditional muscle-specific myristoylated Akt transgenic (TG) mice. To examine the changes in Fstl-1 mRNA level, QRT-PCR was performed using specific primer sets for Fstl-1, normalizing the signal to that of 36B4. Fstl-1 mRNA was significantly upregulated by 2-week Akt activation in skeletal muscle (FIG. 4a). Fstl-1 protein levels in skeletal muscle were also increased after 2-week Akt activation by Western blotting (FIG. 4b).

Example 1d

Figure 6:
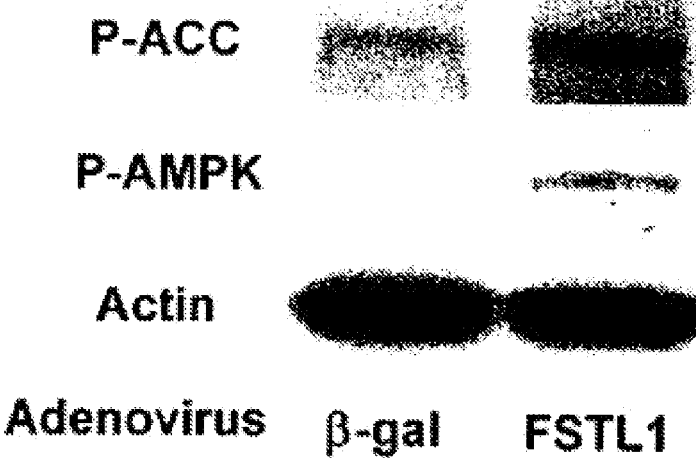
FIG. 6. Fstl-1 stimulates AMPK phosphorylation signaling in C2C12 myotubes. a, Changes in the phosphorylation of AMPK (P-AMPK) and ACC (P-ACC) following Ad-Fstl-1 treatment. Differentiated C2C12 myotubes were transduced with Ad-Fstl-1 or Ad-βgal for 3 days. Phosphorylation of AMPK and ACC was determined by Western blot analysis. b, Transduction with dominant-negative AMPK effectively blocks AICAR-induced phosphorylation of ACC (P-ACC). C2C12 myotubes were transduced with an adenoviral vector expressing dominant-negative AMPK tagged with c-Myc (dnAMPK) or Ad-βgal together with Ad-Fstl-1 and Ad-βgal at total MOI of 250 for 3 days.
Figure 6:
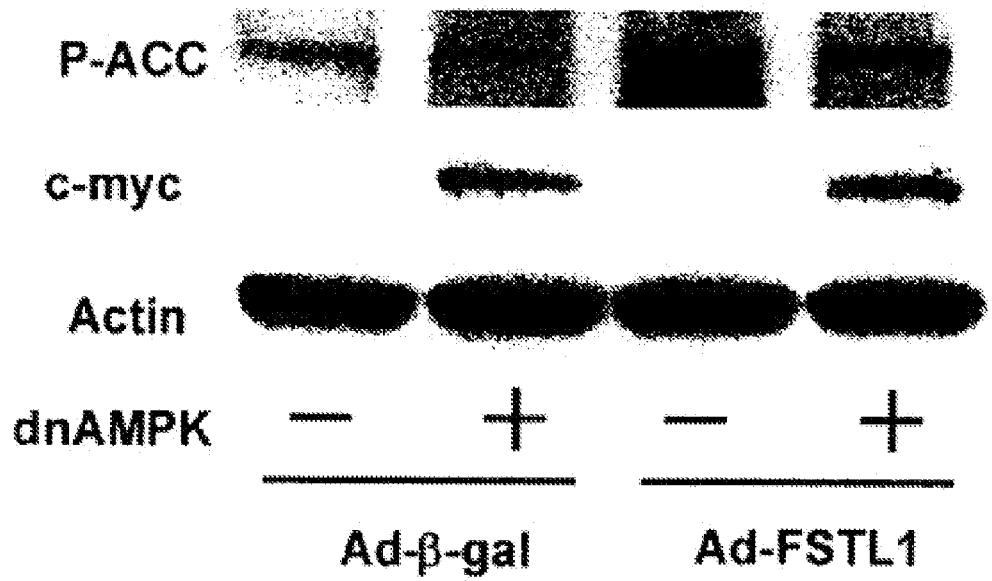

Fstl-1 Overexpression Modulates the Expression of Metabolic Regulatory Factors in Skeletal Muscle It was hypothesized that Fstl-1, which is induced by Akt in skeletal muscle, participates in glucose metabolism. To examine the role of Fstl-1 in metabolism in muscle, mouse skeletal muscle cell line C2C12 cells were transduced with an adenoviral vector expressing Fstl-1 (Ad-Fstl-1) or Ad-βgal as a control. Adenovirus-mediated overexpression of Fstl-1 resulted in an increase in the phosphorylation of AMP-activated protein kinase (AMPK) at Thr 172 (FIG. 6a). Consistent with an increase in AMPK signaling, increases in the phosphorylation of ACC, downstream target of AMPK, were observed. C2C12 cells were transduced with an adenoviral vector expressing a c-Myc-tagged dominant-negative mutant of AMPK (Ad-dnAMPK). Transduction with Ad-dnAMPK suppressed Fstl-1-mediated ACC phosphorylation (FIG. 6b). Collectively, these data suggest that Fstl-1 stimulates AMPK signaling pathway in C2C12 myotubes.

Figure 7:
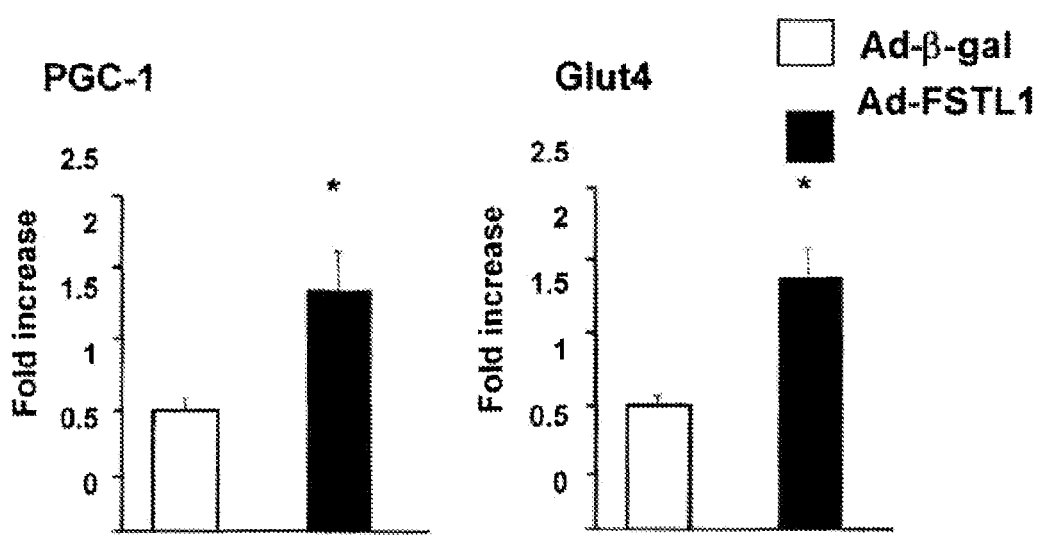
FIG. 7. Fstl-1 increases PGC-1 and Glut4 transcripts in C2C12 cells. C2C12 myotubes were transduced with Ad-Fstl-1 or Ad-βgal for 2 days. PGC-1 and Glut4 mRNA levels were measured by RT-PCR analysis. *$P<0.01$ vs. Ad-βgal.

Because AMPK activation is involved in induction of fatty acid oxidation and glucose uptake in skeletal muscle, the effect of Fstl-1 on transcriptional coactivator PGC-1-α and glucose transporter 4 (Glut4) expression was investigated by RT-PCR. Transduction with Ad-Fstl-1 significantly increased PGC-1-α mRNA levels in C2C12 cells (FIG. 7). Ad-Fstl-1 treatment also increased mRNA levels of Glut4 in C2C12 cells (FIG. 7).

Figure 8:
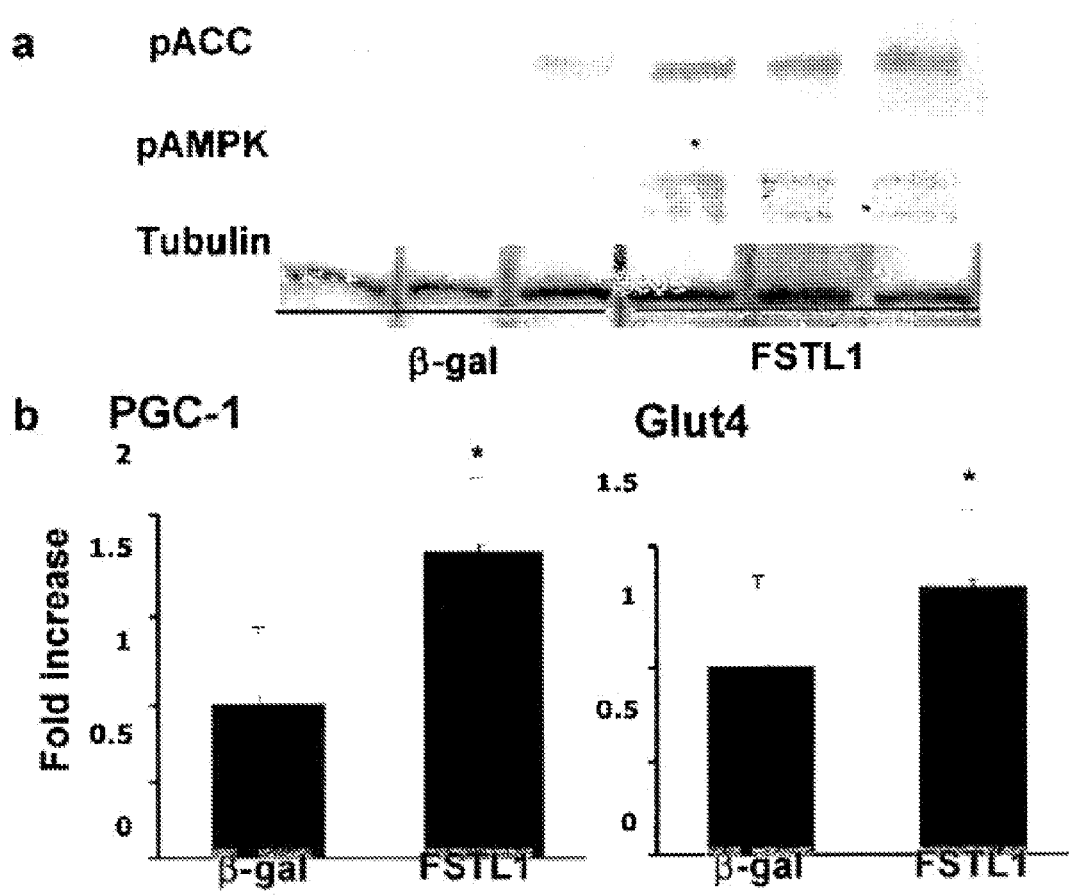
FIG. 8. Fstl-1 promotes AMPK signaling in skeletal muscle in vivo. a, Ad-Fstl-1 or Ad-βgal was injected into 5 sites in gastrocnemius muscles ($4\times10^8$ pfu each) of wild-type mice. At 7 days after injection, phosphorylation of AMPK and ACC was determined by Western blot analysis. b, PGC-1 and Glut4 transcripts in gastrocnemius muscles at 7 days after transduction with Ad-Fstl-1 or Ad-βgal. PGC-1 and Glut4 mRNA levels were measured by RT-PCR analysis. *$P<0.05$ vs. Ad-βgal.

To assess in vivo actions of Fstl-1 on AMPK signaling, Ad-Fstl-1 or Ad-βgal ($4.0 \times 10^8$ pfu/mouse) were intramuscularly injected into gastrocnemius muscles of wild-type mice. At 7 days after injection, AMPK signaling molecules were determined by Western blotting. Transduction with Ad-Fstl-1 stimulated phosphorylation of AMPK and ACC in skeletal muscle (FIG. 8a). Ad-Fstl-1 treatment also upregulated mRNA levels of PGC-1 and Glut4 in skeletal muscle (FIG. 8b).

Example 1e

Fstl-1 Regulates Metabolic Properties in Liver and Glucose Metabolism

Figure 9:
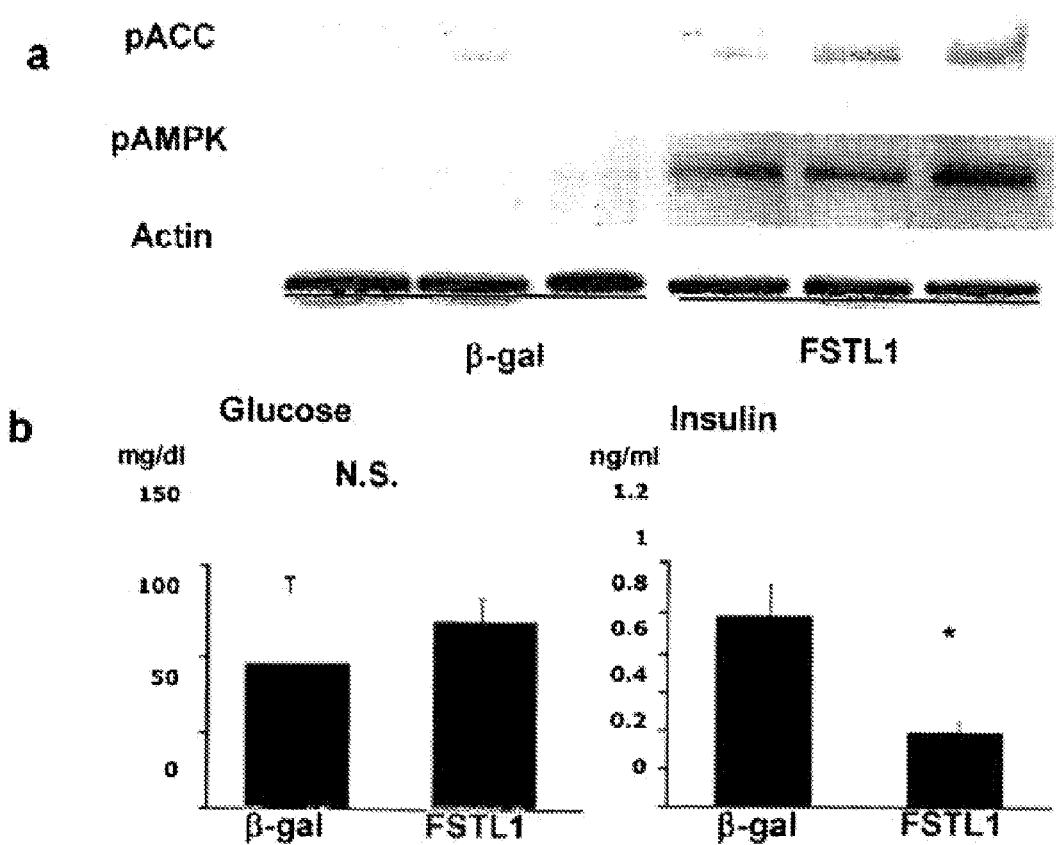
FIG. 9. Fstl-1 stimulates AMPK signaling in liver and reduces insulin levels in vivo. a, Ad-Fstl-1 or Ad-βgal ($8\times10^8$ pfu each) was intravenously injected into wild-type mice that had been fed high fat/high sucrose (HF/HS) diets for 10 days. At 7 days after injection, phosphorylation of AMPK and ACC was determined by Western blot analysis. b, Glucose and insulin levels in serum in HF/HS diet fed wild-type mice treated with Ad-Fstl-1 or Ad-βgal. *$P<0.05$ vs. Ad-βgal.
Figure 10:
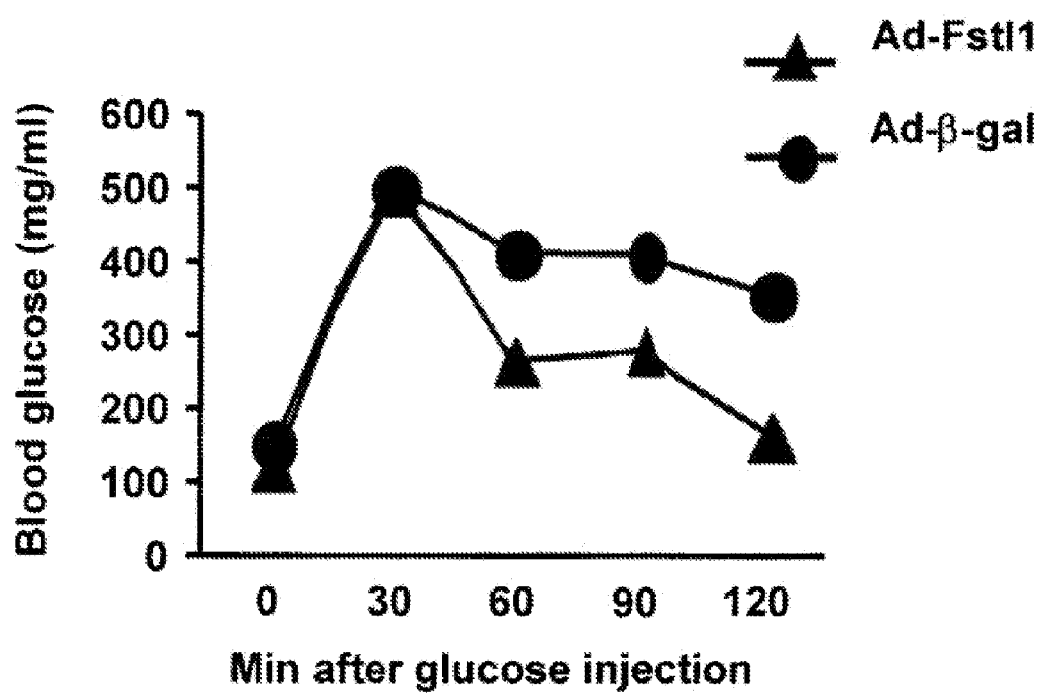
FIG. 10. Fstl-1 improves glucose intolerance in diabetic ob/ob mice. Ad-Fstl-1 or Ad-βgal ($8\times10^8$ pfu each) was intravenously injected into ob/ob mice. At 10 days after injection, glucose tolerance test was performed before and after intraperitoneal delivery of D-glucose (1 g/kg of body weight).

To further elucidate the effect of Fstl-1 on glucose metabolism in vivo, high fat/sucrose diet-induced obese mice were treated intravenously with Ad-Fstl-1 or Ad-βgal ($8.0 \times 10^8$ pfu/mouse). Systemic delivery of Ad-Fstl-1 promoted phosphorylation of AMPK and ACC in liver at 7 days after injection (FIG. 9a). Ad-Fstl-1 reduced serum insulin levels without affecting glucose levels (FIG. 9b). Finally the action of Ad-Fstl-1 on glucose tolerance was investigated in diabetic obese female ob/ob mice. ob/ob mice were treated intravenously with Ad-Fstl-1 or Ad-βgal ($8.0 \times 10^8$ pfu/mouse). At 10 days after injection, a glucose tolerance test was performed. Ad-Fstl-1 improved impaired glucose tolerance after glucose injection in ob/ob mice (FIG. 10). Collectively, these data indicate that Fstl-1 is a modulator of glucose metabolism.

Example 1f

Fstl-1 Prevents NRVCs from Hypoxia/Reoxygenation Induced Apoptosis

Figure 11:
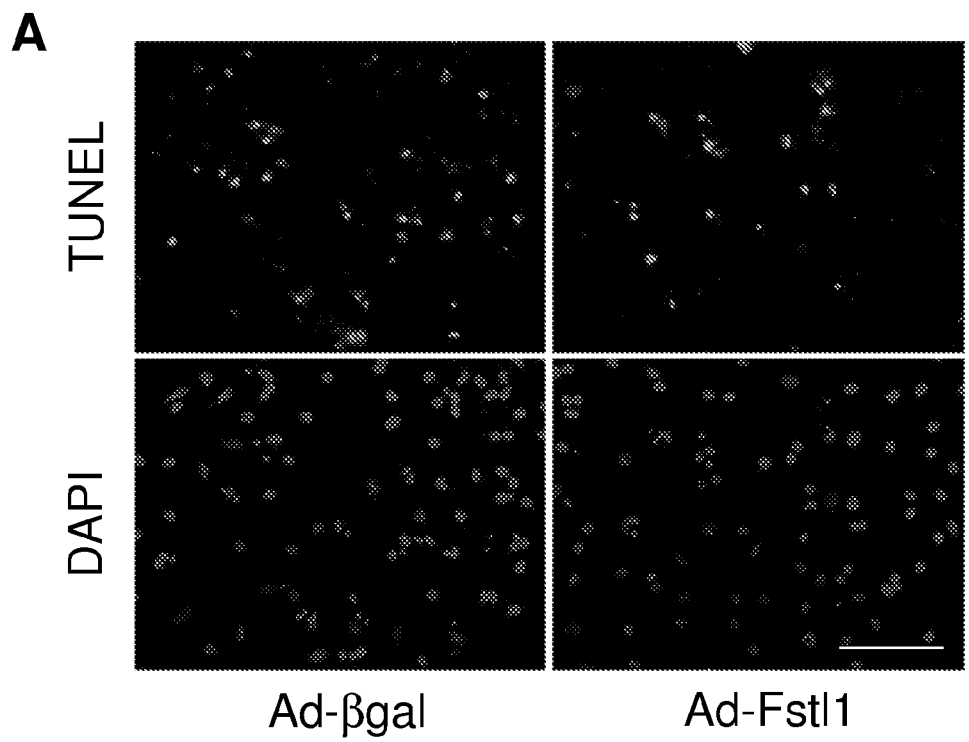
FIG. 11. Fstl1 inhibits H/R-induced apoptosis. A, Serum-deprived NRVMs underwent 12 hours of hypoxia followed by 24 hours of reoxygenation. Representative photographs of cultured stained with TUNEL (green; upper panels) to identify apoptotic nuclei and DAPI (blue; lower panels) to identify total nuclei. Cultures were transfected with Ad-Fstl1 or Ad-βgal prior to H/R. Scale bar: 100 μm. B, Quantification of TUNEL-positive cell number. *$P<0.01$ compared to Ad-βgal transfected NRVMs after H/R. C, Nucleosome fragmentation ELISA shows that transduction with Ad-Fstl1 reduced apoptosis after H/R. *$P<0.01$ compared to Ad-βgal transfected NRVMs after H/R.
Figure 11:
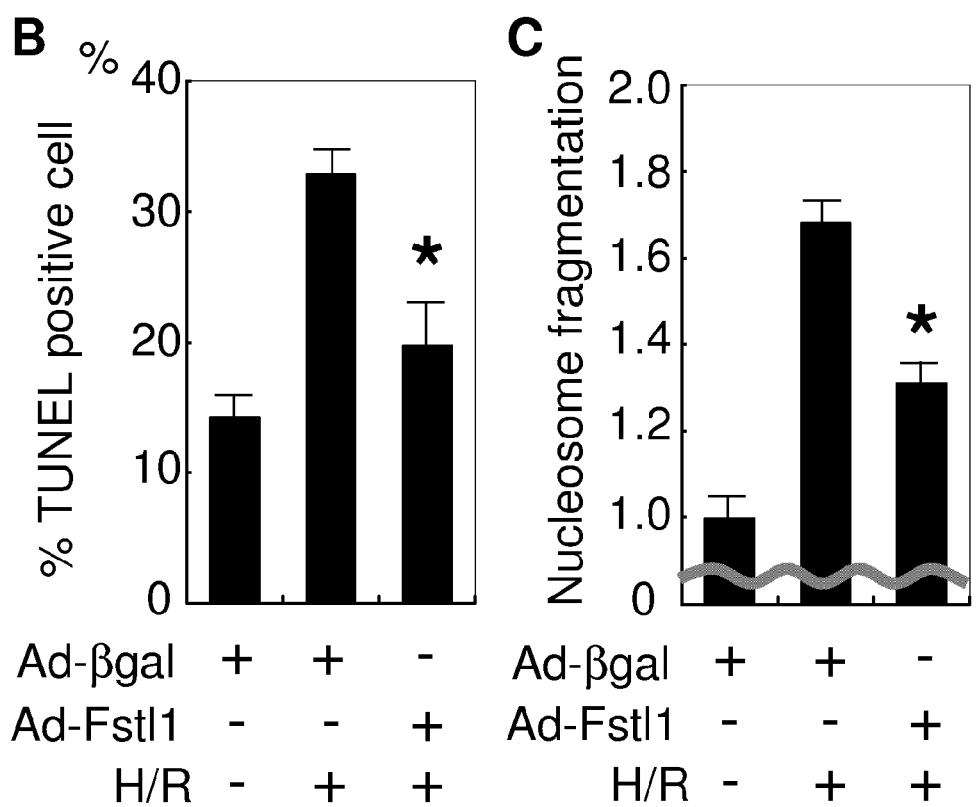

Both Akt and ERK signaling promote cardiomyocyte survival (Fujio Y, et al (2000), supra; Yue T L, et al. (2000) *Circ Res.* 86:692-699). Thus, the effect of Fstl-1 expression on apoptosis after hypoxia/reoxygenation (H/R) was examined in NRVCs. After an 18 to 24 hour incubation in media without serum following adenoviral transduction, cells were exposed to 12 hours of hypoxia followed by 24 hours of reoxygenation. TUNEL staining was performed to evaluate the effect of Fstl-1 on cardiac myocyte apoptosis. As shown in FIG. 11a, treatment with Ad-Fstl-1 reduced the frequency of TUNEL-positive cells under these conditions. As shown in FIG. 11b, quantification of TUNEL positive myocyte number revealed that Ad-Fstl-1 significantly reduced TUNEL positive cell number after H/R compared to Ad-βgal transfected cells (P=0.008). To quantify the effects of Fstl-1 on apoptosis by another method, nucleosome fragmentation was assessed by ELISA. As shown in the FIG. 11c, H/R induced nucleosome fragmentation was significantly suppressed by Ad-Fstl-1 (P=0.004).

Figure 12:
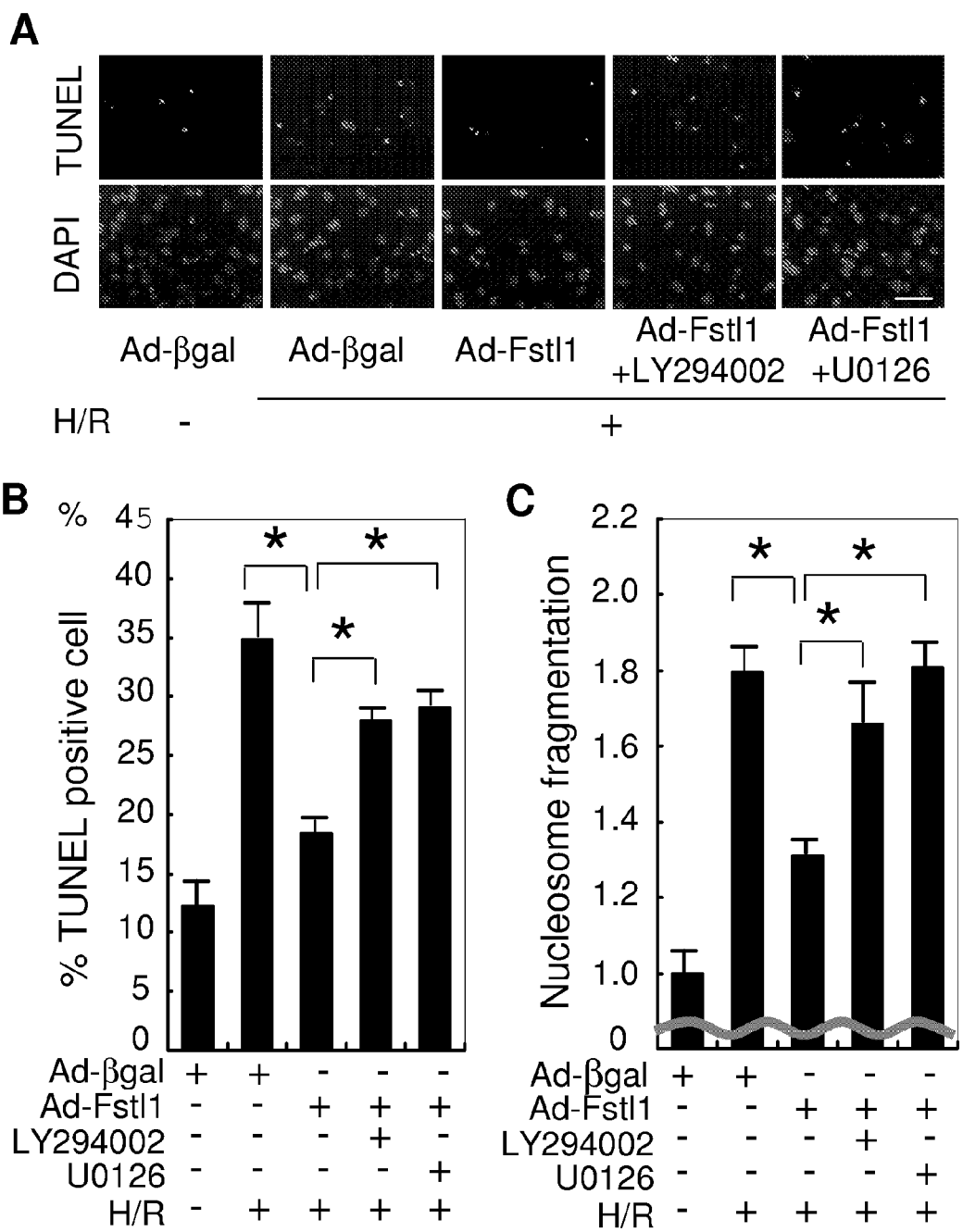
FIG. 12. Fstl1-mediated cytoprotection is mitigated by PI3K or MEK1 inhibition. A, Representative photographs of adenovirus-transduced NRVMs stained with TUNEL (green; upper panels) and DAPI (blue; lower panels). Three hours prior to the induction of hypoxia, NRVMs were pretreated with a PI3K inhibitor (LY294002; LY, 10 μmol/L), a MEK1 inhibitor (U0126; U, 10 μmol/L) or vehicle. Apoptotic nuclei were identified by TUNEL staining. Scale bar: 50 μm. B, Quantification of TUNEL-positive cells under different culture conditions. *$P<0.05$. C, Nucleosome fragmentation ELISA showed that Fstl1-mediated protection of myocytes from apoptosis was reversed by treatment with the PI3K inhibitor or the MEK1 inhibitor. *$P<0.05$.
Figure 13:
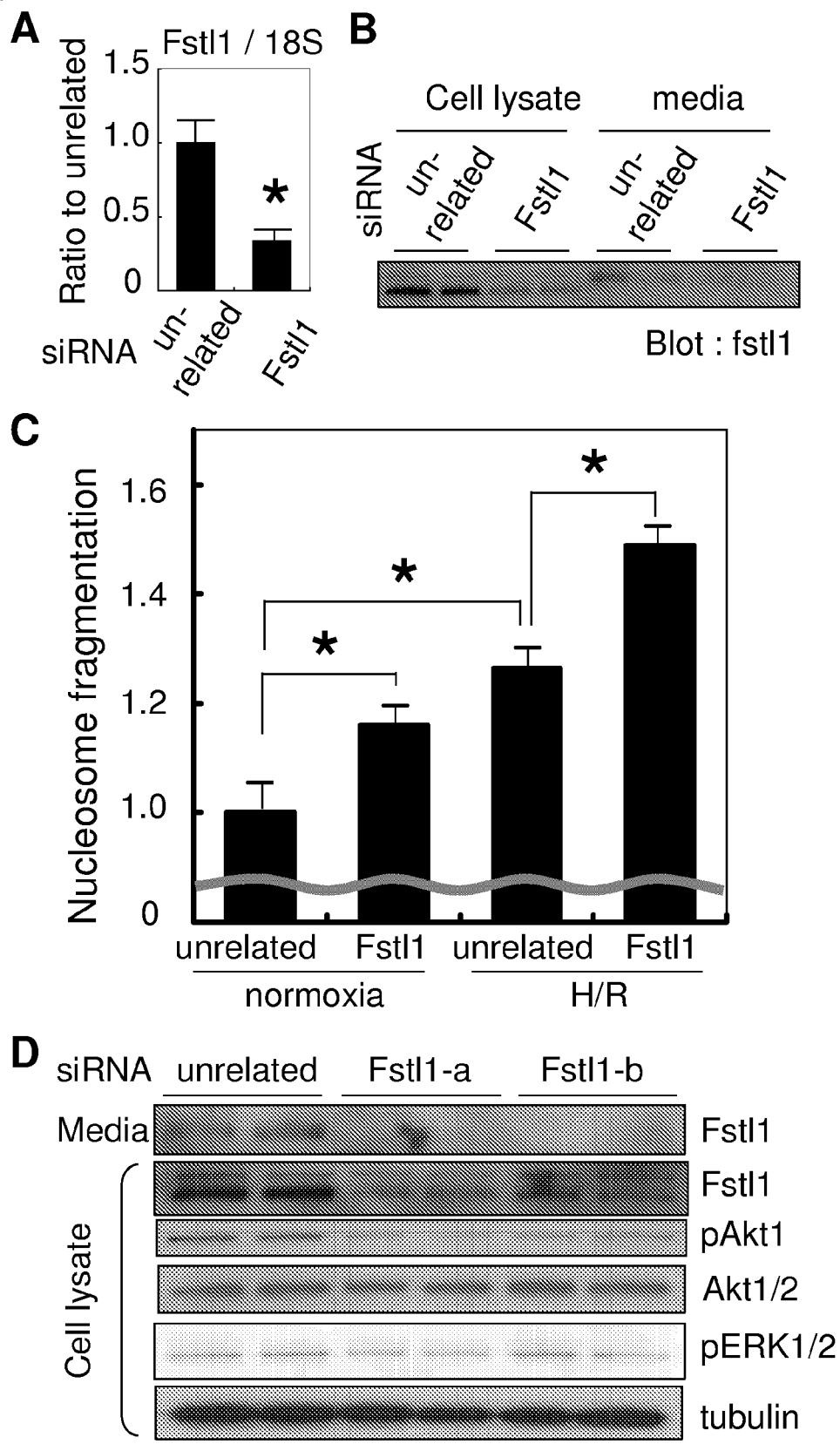
FIG. 13. Knock-down of endogenous Fstl1 increases apoptosis in response to H/R. A, QRT-PCR analysis indicates that transduction of siRNA decreased Fstl1 mRNA by approximately 70% (*$P<0.05$) in cultured cardiac myocytes. B, Representative immunoblot analysis of Fstl1 protein expression in cell lysates and culture media of cardiac myocyte cultures treated with siRNA directed to Fstl1 or an unrelated sequence. C, Nucleosome fragmentation assay shows that knock-down of endogenous Fstl1 expression in serum-deprived cardiac myocyte cultures increases apoptosis in cells under normoxic conditions and in cells treated with H/R ($P<0.05$). D, Immunoblot analysis reveals that Fstl1 ablation results in decreased Akt phosphorylation, but not that of ERK, in cultured cardiac myocytes. Two commercial sources of siRNA targeting Fstl1 were employed in these assays.

To examine the functional significance of Akt and ERK in Fstl-1-mediated cytoprotection, NRCVs were pre-treated with specific inhibitors and subjected to H/R. Cells were exposed to LY294002 (10 µmol/L), a PI3K inhibitor, or with U0126 (10 µmol/L), a MEK 1/2 inhibitor, 3 hours prior to H/R stress. FIG. 12a shows representative fluorescent photographs of TUNEL staining for each group. Transduction with Ad-Fstl-1 reduced TUNEL positive cells after exposure to H/R compared with cells treated with Ad-b-gal, however the protective action of Ad-Fstl-1 was attenuated by pre-incubation with LY29402 or U0126 (FIG. 12b). In agreement with these findings, the inhibitory effect of Fstl-1 on nucleosome fragmentation was significantly attenuated by treatment with each of inhibitor (FIG. 12c).

Example 1g

Figure 14:
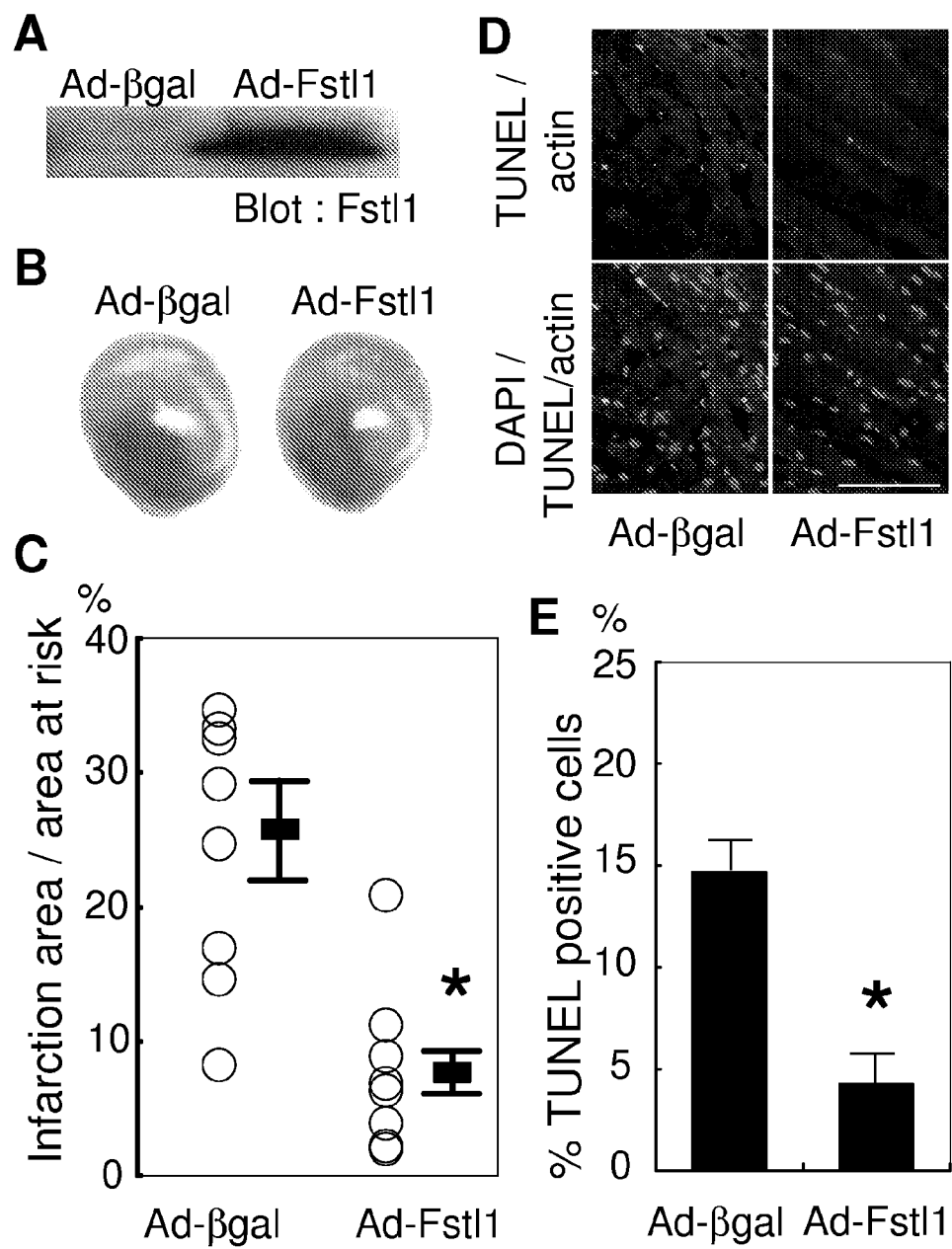
FIG. 14. Fstl1 protects against myocardial I/R injury in vivo. A, Western blot analysis of serum proteins from mice following the intravenous delivery of the indicated adenoviral vector. Sera was collected and analyzed 5 days after adenovirus delivery. Serum Fstl1 level was markedly increased by administration of Ad-Fstl1. B, Representative photographs of heart sections stained with Evans blue and TTC to detect the infarction zone resulting from 30 minutes ischemia and 24 hour reperfusion. I/R injury was performed 5 days after adenoviral injection. C, Quantification of infarction size of each experimental group (n=10 for Ad-βgal group, n=7 for Ad-Fstl1 group). *$P<0.05$ compared to Ad-βgal injected group. D, Representative fluorescent images of heart sections stained with TUNEL (green), sarcomeric actin (red) and DAPI (blue). Scale bar: 100 E, Quantification of TUNEL positive myocyte number showed that administration of Ad-Fstl1 decreased apoptosis (n=3 for each group). *$P<0.01$ compared to Ad-βgal injected group.

Systemic Administration of Fstl-1 Protects the Myocardium from Ischemia/Reperfusion Injury To assess in vivo actions of Fstl-1 on the heart, mice were injected intravenously with Ad-Fstl-1 or Ad-βgal ($1.0 \times 10^9$ p.f.u./mouse) five days prior to myocardial ischemia-reperfusion injury. Five days after the delivery of Ad-Fstl-1, the serum Fstl-1 levels were markedly elevated (FIG. 14a). At this time point mice were exposed to 30 minutes of myocardial ischemia followed by 24 hours of reperfusion. FIG. 14b shows representative heart sections following staining for TTC. Prior treatment with Ad-Fstl-1 resulted in a 66.0% decrease in myocardial infarct size compared with mice treated with Ad-βgal (FIG. 14c). To investigate the extent of apoptosis in the area at risk, TUNEL staining on the different experimental groups were performed. Representative fluorescent photographs of each group are shown in FIG. 14d. Quantitative analysis indicated significantly fewer TUNEL-positive myocytes in the myocardium of mice that were treated with Ad-Fstl-1 (FIG. 14e, $p<0.001$).

Example 2

Follistatin-Like 1 in Regulation of Endothelial Cell Function and Blood Vessel Growth Myogenic Akt signaling coordinates blood vessel recruitment with normal tissue growth. The role of Follistatin-like 1 (Fstl1) in regulation of endothelial cell function and blood vessel growth in muscle was investigated. Transgenic Akt1 overexpression in skeletal muscle led to myofiber growth that was coupled to an increase in muscle capillary density. Myogenic Akt signaling or ischemic hindlimb surgery led to the induction of Fstl1 in muscle and increased circulating levels of Fstl1. Intramuscular administration of an adenoviral vector expressing Fstl1 (Ad-Fstl1) accelerated flow recovery and increased capillary density in the ischemic hindlimbs of wild-type mice, and this was associated with an increase in endothelial nitric oxide synthase (eNOS) phosphorylation at residue Ser1179. In cultured endothelial cells, Ad-Fstl1 stimulated migration and differentiation into network structures, and inhibited apoptosis under conditions of serum deprivation. These cell responses were associated with the activating phosphorylation of Akt and eNOS. Conversely, transduction with dominant-negative Akt or LY294002 blocked Fstl1-stimulated eNOS phosphorylation and inhibited Fstl1-stimulated cellular responses. Treatment with the eNOS inhibitor L-NAME also reduced endothelial cell migration and differentiation induced by Ad-Fstl1. The stimulatory effect of Ad-Fstl1 on ischemic limb reperfusion was abolished in mice lacking eNOS. These data indicate that Fstl1 is a secreted muscle protein or myokine that can function to promote endothelial cell function and stimulates revascularization in response to ischemic insult through its ability to activate Akt-eNOS signaling.
Background
Skeletal muscle hypertrophy is associated with blood vessel recruitment, such that capillary density is either maintained or increased during muscle growth (Degens, H., et al. (1993) Int. J. Biochem. 25, 1141-1148; Degens, H., et al. (1992) J. Anat. 180, 455-463; Ingjer, F. (1979) Eur. J. Appl. Physiol. Occup. Physiol. 40, 197-209; Kano, Y., et al (1997) Eur. J. Appl. Physiol. Occup. Physiol. 75, 97-101). A number of studies have shown that the serine-threonine protein kinase Akt1 plays a key role in regulation of cellular hypertrophy and organ size (Shiojima, I., and Walsh, K. (2006) Genes Dev 20, 3347-3365). The expression of constitutively-active Akt1 in skeletal muscle stimulates muscle hypertrophy both in vitro and in vivo (Takahashi, A., et al. (2002) Mol. Cell. Biol. 22, 4803-4814; Lai, K. M., et al. (2004) Mol. Cell. Biol. 24, 9295-9304; Bodine, S. C., et al. (2001) Nat. Cell Biol. 3, 1014-1019; Izumiya, Y., et al (2008) Cell Metab 7, 159-172). Adenovirus-mediated transduction of constitutively-active Akt1 also promotes the induction of the vascular endothelial growth factor (VEGF), and this is accompanied by an increase in limb perfusion and capillary density in muscles where Akt1 is overexpressed (Takahashi, A., et al. (2002), supra). Constitutive activation of Akt1 in the heart also promotes myocardial angiogenesis, which is partly mediated by the induction of VEGF (Shiojima, I., et al. (2005) J. Clin. Invest. 115, 2108-2118; Izumiya, Y., et al. (2006) Hypertension 47, 887-893). Collectively, these data suggest that the Akt-VEGF signaling axis is a critical regulator of blood vessel recruitment during tissue growth. However, the process of angiogenesis is regulated by complex molecular mechanisms involving the participation of multiple factors (Carmeliet, P. (2005) Nature 438, 932-936). Thus, it was sought to identify novel factors secreted from skeletal muscle that coordinate blood vessel recruitment with myofiber growth.

Follistatin-like 1 (Fstl1), also referred to as TSC36, is an extracellular glycoprotein that, despite limited homology, has been grouped into the follistatin family of proteins (Shibanuma, M., et al (1993) Eur J Biochem 217, 13-19). Fstl1 is poorly understood with regard to its functional significance. Transduction of cancer cell lines with Fstl1 has been shown to result in suppression of growth and invasion (Sumitomo, K., et al. (2000) Cancer Lett 155, 37-46; Johnston, I. M., et al. (2000) Oncogene 19, 5348-5358). Recently, it was demonstrated that Fstl1 is upregulated in myocardium in cardiac-specific Akt1 transgenic (TG) mice and that Fstl1 functions as a cardioprotective molecule with anti-apoptotic actions in cardiac myocytes (Oshima, Y., Ouchi, N., Sato, K., Izumiya, Y., Pimentel, D., and Walsh, K. (2008) Circulation, In press.). To date, however, the secretion of Fstl1 by skeletal muscle has not been investigated and no functional analysis of Fstl1 has been performed in the setting of vascular disease. In the present study, it was tested whether Fstl1 is secreted from skeletal muscle and whether it participates in blood vessel recruitment that is associated with muscle ischemia or myogenic Akt1 signaling. It was also investigated whether Fstl1 affects cellular behavior and modulates intracellular signaling in cultured endothelial cells. These observations indicate that Fstl1 is a secreted factor in myogenic cells that favors ischemia-induced revascularization through activation of Akt-eNOS-dependent signaling within endothelial cells.

Example 2a

Experimental Procedures

Materials—Phospho-Akt (Ser473), phospho-eNOS (Ser1177), phospho-p42/44 extracellular signal-regulated kinase (ERK) (Thr202/Tyr204), phospho-GSK-3β (Ser9), Akt and ERK antibodies were purchased from Cell Signaling Technology. eNOS and GSK-3 antibodies was from Santa Cruz Biotechnology, tubulin antibody was from Oncogene and Fstl1 antibody was obtained from R&D Systems. Antihuman Fstl1 antibody was obtained from Abcam. LY294002 was obtained from Calbiochem, and NG-nitro-L-arginine methyl ester (L-NAME) was obtained from Sigma.

Muscle-specific Akt1 Transgenic Mice—The generation of skeletal muscle-specific inducible myrAkt1 transgenic (TG) mice was described previously (Izumiya, Y., et al. (2008), supra). Briefly, tetracycline-responsive element constitutively-active myrAkt1 (TRE-myrAkt1) TG mouse line was crossed with 1256 [3Emut] MCK-rtTA lines that express reverse tetracycline transactivator (rtTA) from 1256 [3Emut] MCK promoter to generate double-transgenic mice (DTG). To activate Akt1 transgene, DTG were administered doxycycline (DOX, 0.5 mg/ml) in their drinking water. Single 1256 [3Emut] MCK-rtTA TG littermates were used as controls and treated with DOX in the same way as DTG mice.

Microarray Analysis—Total RNA from gastrocnemius muscles of DTG mice (2 weeks after Akt1 induction) and control rtTA TG littermates was analyzed by Affymetrix GeneChip Mouse Expression Set 430 microarrays. Among transcripts that are upregulated by Akt1 activation, transcripts were selected that have full-length open reading frame cDNAs available in the National Center for Biotechnology Information Web site. Amino acid sequences were examined for signal sequences by Signal IP software. Amino acid sequences were also analyzed with SOSUI signal beta version software to predict proteins lacking transmembrane domain.

Mouse Model of Revascularization—Male wild-type and eNOS-deficient (eNOS-KO) mice (Jackson Laboratory) in a C57/BL6 background were used for this study. Study protocols were approved by the Institutional Animal Care and Use Committee in Boston University. Mice, at the ages of 10 weeks, were subjected to unilateral hindlimb surgery under anesthesia with sodium pentobarbital (50 mg/kg intraperitoneally). In this model, the entire left femoral artery and vein were excised surgically (Ouchi, N., et al. (2005) Circ. Res. 96, 838-846; Shibata, R., et al. (2004) J. Biol. Chem. 279, 28670-28674). In some experiments, the $2 \times 10^8$ plaque-forming units (pfu) of adenoviral constructs encoding Fstl1 (Ad-Fstl1) or expressing β-galactosidase (Ad-βgal), as a control, were injected into five different sites of adductor muscle in the ischemic limb 3 days prior to the ischemic hindlimb as previously described (Ouchi, N., et al. (2005), supra; Shibata, R., et al. (2004), supra). Hindlimb blood flow was measured using a laser Doppler blood flow (LDBF) analyzer (Moor LDI; Moor Instruments) immediately before surgery and on postoperative days 3, 7, and 14. Hindlimb blood flow was expressed as the ratio of left (ischemic) to right (nonischemic) LDBF. In some experiments, Ad-Fstl1 or Ad-β-gal was injected into gastrocnemius muscle of wild-type mice ($2 \times 10^8$ pfu each). Following sacrifice, capillary density within gastrocnemius or thigh adductor muscle was quantified by histological analysis (Ouchi, N., et al. (2005), supra; Shibata, R., et al. (2004), supra). Muscle samples were imbedded in OCT compound (Miles, Elkhart, Ind., USA) and snap-frozen in liquid nitrogen. Tissue slices (5 μm in thickness) were stained with anti-CD31 (PECAM-1: Becton Dickinson) antibodies. Fifteen randomly chosen microscopic fields from three different sections in each tissue block were examined for the presence of CD31-positive capillary endothelial cells. Capillary density was expressed as the number of CD31-positive cells per muscle fiber or per high power field.

Cell Culture, Adenoviral Infection and Western Blot Analysis—Human umbilical vein endothelium cells (HUVECs) were cultured in endothelial cell growth medium-2 (EGM-2, Lonza) (Ouchi, N., et al. (2004) J. Biol. Chem. 279, 1304-1309). HUVECs were infected with adenoviral constructs encoding mouse Fstl1 (Ad-Fstl1) (Oshima, Y., Ouchi, N., Sato, K., Izumiya, Y., Pimentel, D., and Walsh, K. (2008) Circulation, In press.), or Ad-β-gal at a multiplicity of infection (MOI) of 10 for 8 h and placed in endothelial cell basal medium-2 (EBM-2, Lonza) without serum for indicated lengths of time. In some experiments, HUVECs were treated with LY294002 (10 μM), L-NAME (1 mg/ml) or vehicle along with transduction with Ad-Fstl1 or Ad-βgal. In some experiments, HUVECs were infected with adenoviral constructs encoding dominant-negative Akt1 (Ad-dnAkt) with a hemagglutinin (HA) tag. (Ouchi, N., et al. (2004), supra; Fujio, Y., and Walsh, K. (1999) J. Biol. Chem. 274, 16349-16354) or Ad-βgal at a MOI of 10 together with Ad-Fstl1 or Ad-β-gal. C2C12 mouse myoblasts (American Type Culture Collection) were maintained in growth medium (DMEM supplemented with 20% FBS) and shifted to differentiation medium (DMEM supplemented with 2% heat-inactivated horse serum) for 4 days to induce differentiation (Ouchi, N., et al (2005), supra). C2C12 myocytes were infected with Ad-Fstl1, or Ad-β-gal at a MOI of 250 for 16 h followed by incubation with serum free DMEM for 24 h. Cell and tissue lysates or culture media were resolved by SDS-PAGE. The membranes were immunoblotted with the indicated antibodies at a 1:1000 dilution followed by the secondary antibody conjugated with horseradish peroxidase (HRP) at a 1:5000 dilution. ECL Western Blotting Detection kit (Amersham) was used for detection. Relative phosphorylation or protein levels were quantified by Image J program. Immunoblots were normalized to total loaded protein.

Determination of Fstl1 mRNA—Total RNA was prepared by Qiagen using the manufacturer's suggested protocol, and cDNA was produced using ThermoScript RT-PCR Systems (Invitrogen). Quantitative Real-time PCR (QRT-PCR) was performed on iCycler iQ Real-Time PCR Detection System (BIO-RAD) using SYBR Green I as a double stranded DNA specific dye as described previously (Ouchi, N., et al (2005), supra). Primers were: 5'-AACAGCCATCAACATCAC-CACTTAT-3' and 5'-TTTCCAGTCAGCGTTCTCATCA-3' for mouse Fstl1, 5'-TCACCACCATGGAGAAGGC-3' and 5'-GCTAAGCAGTTGGTGGTGCA-3' for mouse GAPDH.

Migration Assay—Migratory activity was measured using a modified Boyden chamber assay (Ouchi, N., et al. (2004), supra). Serum-deprived cells were trypsinized and resuspended in EBM-2 in the absence of serum. Cell suspensions (250 μl, $2.0 \times 10^4$ cells/well) were added to the transwell insert (8.0 μm pore size, Becton Dickinson). After 18 h, migrated cells on the lower surface of the membrane were fixed, stained with Giemsa stain solution and eight random microscopic fields per well were quantified.

Differentiation Assay—The formation of network structures by HUVECs on growth factor-reduced Matrigel (Becton Dickinson) was performed as previously described (Ouchi, N., et al. (2004), supra). Twenty-four-well culture plates were coated with Matrigel according to the manufacturer's instructions. HUVECs were seeded on coated plates at $5 \times 10^4$ cells/well in serum-free EBM-2 and incubated at 37° C. for 18 h. Network formation was observed using an inverted phase contrast microscope (Nikon). Images were captured with a video graphic system (DEI-750 CE Digital Output Camera, Optronics). The degree of differentiation into vascular-like structures was quantified by measuring the network areas in three randomly chosen fields from each well using Image J program.

Analysis of Apoptotic Activity—Cells were transduced with adenoviral constructs for 8 h followed by incubation with serum-free EBM-2 for 48 h. Nucleosome fragmentation was assessed by ELISA using Cell Death Detection kit (Roche). Cell viability was also measured by MTS reagent using the CellTiter 96 AQueous kit (Promega) (Kobayashi, H., et al. (2004) *Circ. Res.* 94, e27-e31). TUNEL staining was performed using the In Situ Cell Death detection kit (Roche) (Shibata, R., et al. (2005) *Nat. Med.* 11, 1096-1103). TUNEL positive cells were counted in five randomly selected microscopic fields. Each experiment was repeated four times.

Statistical Analysis—All data are expressed as means±SD or SEM as indicated in the figure legends. Differences were analyzed by Student's unpaired t test or ANOVA for multiple comparisons. A level of P<0.05 was accepted as statistically significant.

Example 2b

Figure 15:
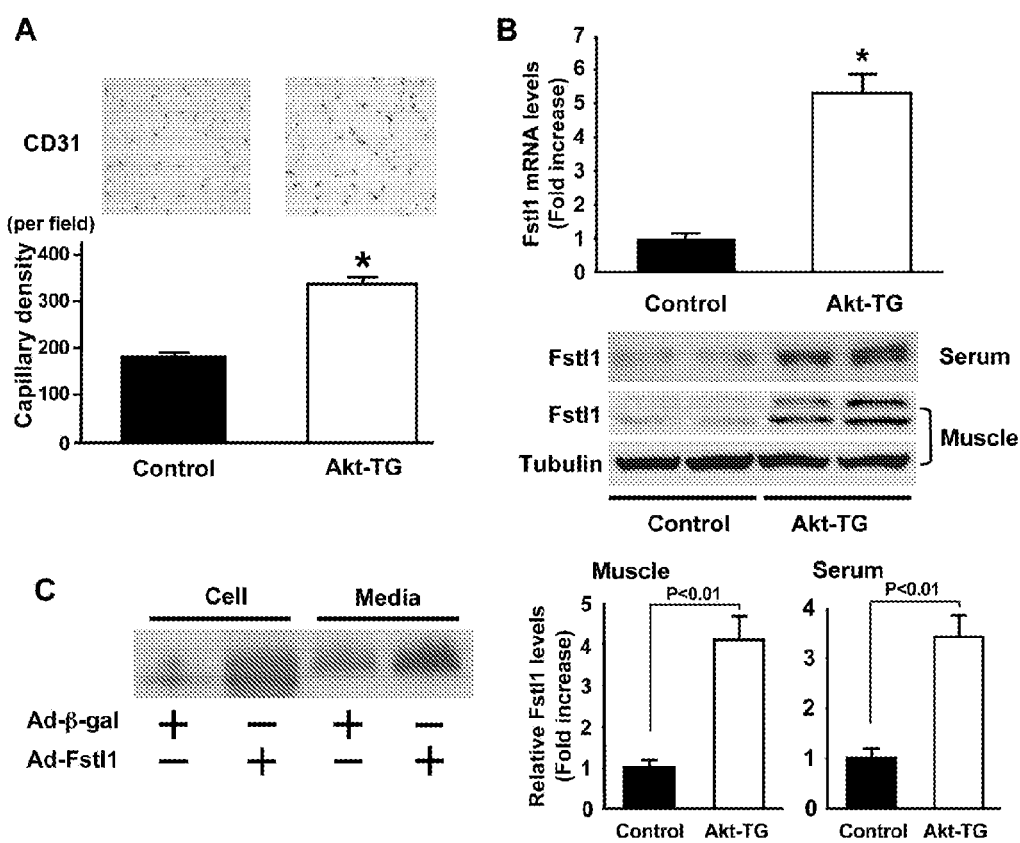
FIG. 15. Transgenic Akt activation increases capillary density and Fstl1 expression in gastrocnemius muscle. A, Increased capillary vessels in gastrocnemius muscles in muscle-specific Akt-TG mice following 2 weeks of Akt1 activation. Immunostaining of gastrocnemius tissues of control (n=5) and Akt-TG (n=5) mice was performed with anti-CD31 monoclonal antibody. Capillary density was expressed as the number of capillaries per high power field. Results are shown as the mean±SEM. *$p<0.01$ vs. Control mice. B, Upregulation of Fstl1 expression in gastrocnemius muscle and serum in muscle-specific Akt-TG mice after Akt1 activation for 2 weeks. Fstl1 expression was determined by QRT-PCR and Western blot analyses (n=5). Fstl1 mRNA levels were expressed relative to levels of GAPDH mRNA. Results are expressed relative to control. Relative protein levels of Fstl1 were quantified (n=4-5) by Image J program. Results are shown as the mean±SEM. *$p<0.01$ vs. Control. C, Fstl1 is secreted from C2C12 myotube cultures. C2C12 cells were transduced with adenoviral vectors expressing Fstl1 (Ad-Fstl1), or β-galactosidase (Ad-β-gal) for 16 h followed by 24 h of incubation in serum-free media. Fstl1 protein levels were determined in media and cell lysates by Western blot analysis. Representative blots are shown from 3 independent experiments.

Akt1 Overexpression in Skeletal Muscle Increases Capillary Vessel Formation and Upregulates Fstl1 Expression Initially the consequences of Akt1 transgene expression on blood vessel formation in skeletal muscle was examined by employing skeletal muscle-specific Akt1 TG mice (9). Mice were treated with DOX for 2 weeks to activate Akt1 transgene, resulting in an approximately 40% increase in gastrocnemius muscle mass weight (Izumiya, Y., et al (2008), supra). At this time point, capillary density in gastrocnemius muscle was assessed by staining with an endothelial marker CD31. FIG. 15 shows representative photographs of tissues stained with CD31. Quantitative analysis revealed that the capillary density per high power field was significantly increased in mice following 2 weeks of Akt1 activation compared with control mice (FIG. 15A). Similarly, the number of CD31-positive cells per muscle fiber was significantly higher in Akt1-TG mice than in control mice (0.84±0.07 in control mice and 2.45±0.19 in Akt1-TG mice).

Microarray analysis of expressed transcripts was performed, and transcripts upregulated by myogenic Akt signaling were evaluated for the presence of a signal peptide and the absence of a transmembrane domain in their open reading frames using Signal IP and SOSUI software, respectively. The Fstl1 transcript was of interest because it was upregulated by a factor of 1.9 after Akt1 transgene activation by microarray analysis, and it is predicted to encode a secreted protein. Next, the effect of transgenic Akt1 activation on Fstl1 expression in skeletal muscle was confirmed. Fstl1 mRNA levels were upregulated in gastrocnemius muscle by a factor of 5.3 following 2 weeks of Akt1 activation, as determined by QRT-PCR analysis (FIG. 15B). Fstl1 protein levels were also increased in gastrocnemius muscle by Akt1 transgene induction as assessed by Western blot analysis (FIG. 15B). Two immunoreactive bands of Fstl1 (37 kDa and 46 kDa proteins) were detected in mouse skeletal muscle. Quantitative analysis of 37 kDa band indicated the 4.1±0.5-fold increase in Fstl1 protein. Fstl1 protein was also detected in mouse serum, and serum Fstl1 levels were markedly increased by a factor of 3.4±0.4 at 2 weeks after Akt transgene activation in skeletal muscle (FIG. 15B).

To examine whether Fstl1 is secreted from cultured muscle cells, differentiated C2C12 cells were treated with adenoviral vectors expressing Fstl1 (Ad-Fstl1) or β-galactosidase (Ad-β-gal). Fstl1 protein was detected in both the cell pellet lysate and media of control cells treated with Ad-β-gal (FIG. 15C). Ad-Fstl1 treatment increased Fstl1 protein levels in both the cell lysate (2.7±0.1-fold increase) and media (2.0±0.3-fold increase)(FIG. 15C). Collectively, these data suggest that Fstl1 is upregulated by Akt signaling and secreted from skeletal muscle.

Example 2c

Muscle Ischemia Upregulates Fstl1 Expression

Figure 16:
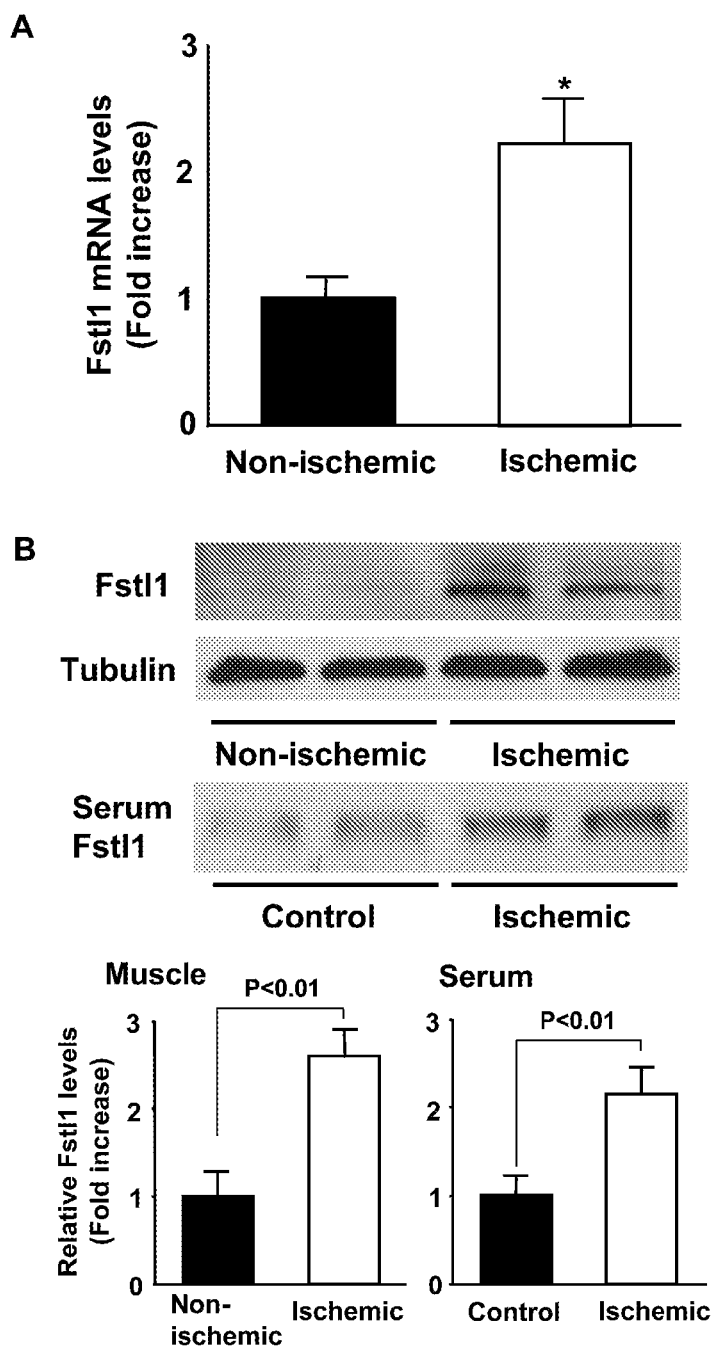
FIG. 16. Elevated Fstl1 levels in ischemic muscle and serum after hindlimb ischemic surgery. A, Fstl1 expression in non-ischemic or ischemic adductor muscles was measured by QRT-PCR (n=5) at day 7 after femoral artery resection. Fstl1 transcript levels were expressed relative to levels of GAPDH mRNA. Results are expressed relative to control. B, Fstl1 expression in non-ischemic (n=4) and ischemic skeletal muscle (n=4) was measured by Western blot analyses on the postoperative day 14. Serum was collected from control (n=4) or mice subjected to hindlimb ischemic surgery (n=4), and Fstl1 levels were determined by Western blot analyses. Relative protein levels of Fstl1 were quantified (n=4) by Image J program. Results are shown as the mean±SEM. *$p<0.05$ vs. Non-ischemic.

To further characterize the regulation of Fstl1, expression was determined in ischemic adductor muscle following femoral artery excision. Fstl1 mRNA levels were 2.3-fold higher in ischemic muscles than in non-ischemic muscles at 7 days after ischemic surgery as measured by QRT-PCR analysis (FIG. 16A). Fstl1 protein levels in ischemic muscles were also increased by a factor of 2.6±0.3 as assessed by Western blot analysis (FIG. 16B). Furthermore, hindlimb ischemia increased Fstl1 levels in serum by a factor of 2.1±0.3 at 2 weeks following ischemic surgery (FIG. 16B).

Example 2d

Fstl1 Promotes Revascularization in Response to Ischemia In Vivo

Figure 17:
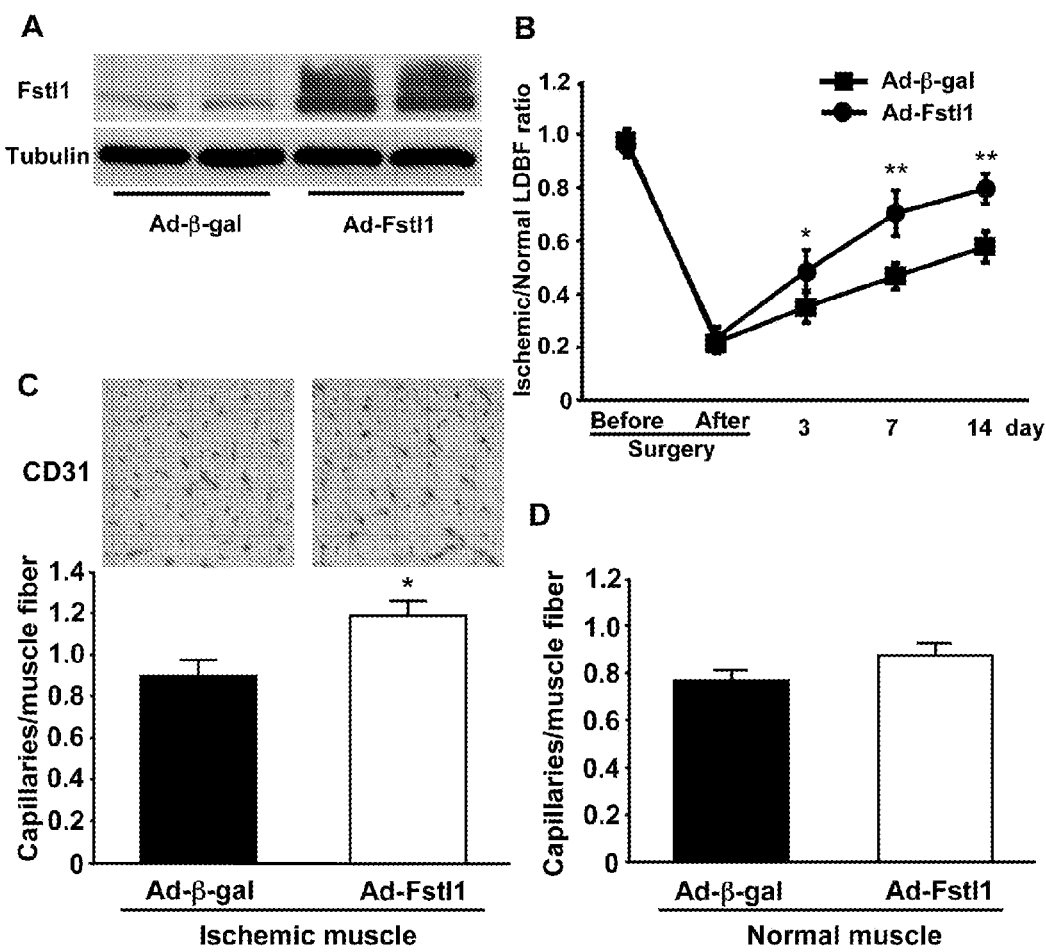
FIG. 17. Fstl1 promotes perfusion recovery and capillary vessel formation of ischemic limbs in mice in vivo. Adenoviral vectors expressing Fstl1 (Ad-Fstl1), or β-galactosidase (Ad-β-gal, Control) were injected into 5 sites in adductor muscle of wild-type mice ($2 \times 10^8$ pfu each) at 3 days prior to ischemic surgery. A, Fstl1 expression in ischemic muscle at 6 days after injection of Ad-Fstl1 or Ad-β-gal. Fstl1 protein expression was determined by Western blot analysis. Representative blots are shown from 5 independent experiments. B, Quantitative analysis of the ischemic/nonischemic LDBF ratio in wild-type mice treated with Ad-Fstl1 (n=8) and Ad-β-gal (n=8). Results are shown as the mean±SD. *$p<0.05$ vs. Control mice. **$p<0.01$ vs. Control mice. C, Quantitative analysis of capillary density in ischemic muscles of wild-type mice treated with Ad-Fstl1 (n=5) and Ad-β-gal (n=5) on postoperative day 14. Immunostaining of ischemic tissues was performed with anti-CD31 monoclonal antibody. Capillary density was expressed as the number of capillaries per muscle fiber. Results are shown as the mean±SEM. *$p<0.01$ vs. Control mice. D, Quantitative analysis of capillary density in non-ischemic gastrocnemius muscles of wild-type mice treated with Ad-Fstl1 (n=4) and Ad-β-gal (n=4) at day 7 after injection ($2 \times 10^8$ pfu each). Immunostaining of gastrocnemius muscle tissues was performed with anti-CD31 monoclonal antibody. Capillary density was expressed as the number of capillaries per muscle fiber. Results are shown as the mean±SEM.

To test whether Fstl1 can modulate revascularization under conditions of ischemia in vivo, C57BL/6 wild-type mice were employed that underwent unilateral femoral artery resection. This model of vascular insufficiency has been used to evaluate the in vivo angiogenic actions of growth factors including VEGF (Couffinhal, T., et al. (1999) *Circulation* 99, 3188-3198; Rivard, A., et al. (1999) *Am. J. Pathol.* 154, 355-363). Adenoviral vectors expressing Fstl1 (Ad-Fstl1) or Ad-β-gal (control) were injected intramuscularly into the adductor muscle 3 days before surgery. Fstl1 protein levels in ischemic muscle were significantly elevated by a factor of 6.9±0.5 at 6 days after injection of Ad-Fstl1 (FIG. 17A). Ad-Fstl1-treated mice showed a significant increase in flow recovery at 3, 7 and 14 days after ischemic surgery as determined by laser Doppler blood flow analysis (FIG. 17B). To investigate the extent of revascularization at the microcirculatory level, capillary density was measured in histological sections harvested from the ischemic muscles. Quantitative analysis revealed that the capillary density was significantly increased in Ad-Fstl1-treated mice compared with control mice on postoperative day 14 (FIG. 17C).

To investigate whether Fstl1 can stimulate blood vessel growth in non-ischemic muscle, the gastrocnemius muscle of wild-type mice was injected with Ad-Fstl1 or Ad-β-gal. No significant differences in the capillary density of non-ischemic muscles were observed between Ad-Fstl1-treated and control mice (FIG. 17D). Collectively, these data indicate that Fstl1 will enhance revascularization in ischemic tissue, but it is not sufficient to activate an angiogenic response in normal tissue.

Example 2e

Fstl1 Promotes Endothelial Cell Function and Survival In Vitro

Figure 18:
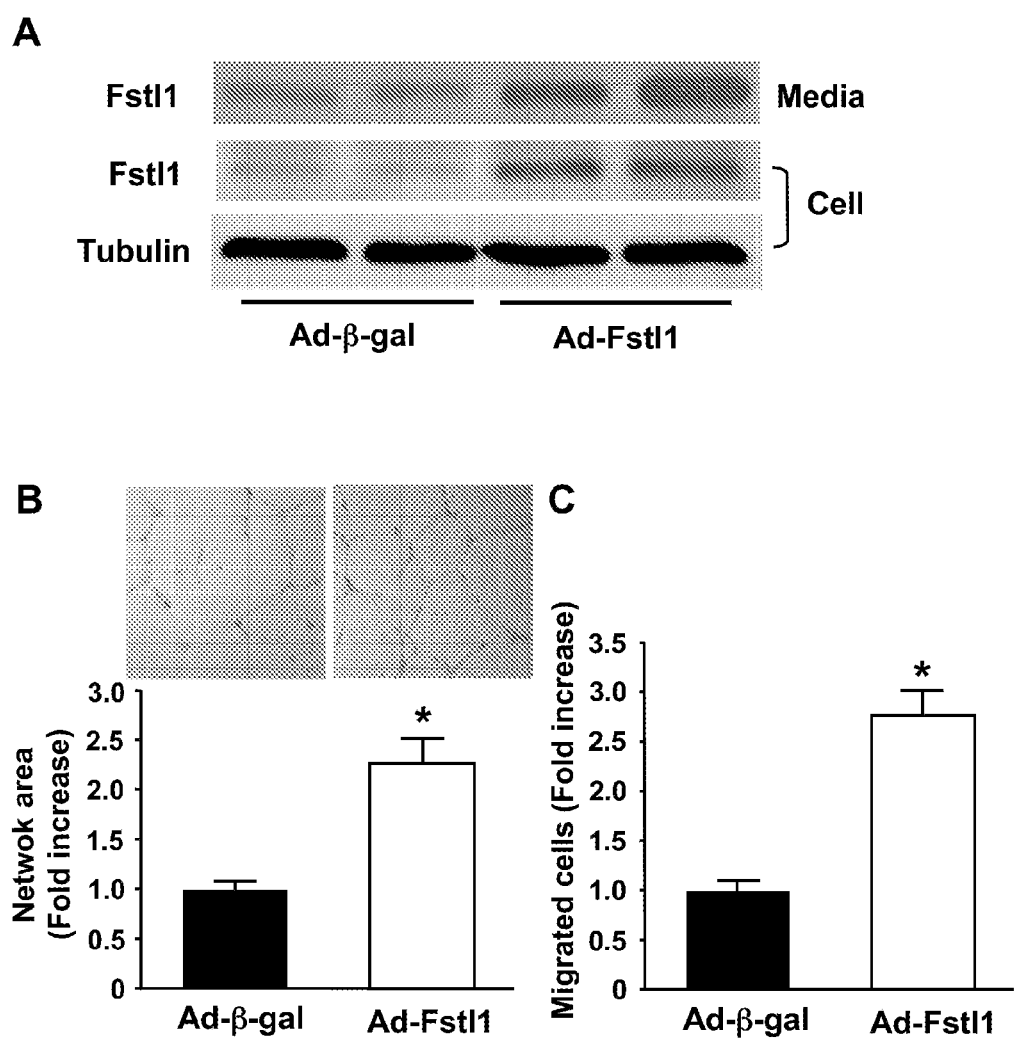
FIG. 18. Fstl1 promotes endothelial cell migration and differentiation into vascular-like structures. A, Expression of Fstl1 protein in media and cell lysates from HUVECs. HUVECs were transduced with Ad-Fstl1 and Ad-β-gal for 8 h followed by 24 h of incubation in serum-free media. Fstl1 protein levels were determined in media and cell lysates from HUVECs by Western blot analysis. Representative blots are shown from 4 independent experiments. B, Endothelial cell network formation in response to Fstl1. After 24 h of serum-deprivation and transduction with Ad-Fstl1 and Ad-β-gal, HUVECs were seeded on Matrigel-coated culture dishes. Representative cultures are shown (upper panel). Quantitative analyses of network formation are shown (bottom panel). C, Migratory activities of HUVECs following treatment with Fstl1. A modified Boyden chamber assay was performed using HUVECs transduced with Ad-Fstl1 and Ad-β-gal. Results are shown as the mean±SEM (n=7-8). Results are expressed relative to the values compared to control. *$p<0.01$ vs. Ad-β-gal.

To examine whether Fstl1 can directly act on endothelial cells, HUVECs were transduced with Ad-Fstl1 or Ad-β-gal and plated on a Matrigel matrix. Fstl1 protein expression was readily detected in both cell lysate (4.6±0.3-fold increase) and media (3.5±0.4-fold increase) from HUVECs treated with Ad-Fstl1, whereas endogenous levels of Fstl1 expression were low (FIG. 18A). Quantitative analyses of endothelial cell network area revealed that treatment with Ad-Fstl1 significantly promoted the formation of network structures relative to control cultures treated with Ad-β-gal (FIG. 18B). To test whether Ad-Fstl1 influences endothelial cell migration, a modified Boyden chamber assay was performed. Ad-Fstl1 treatment significantly stimulated HUVEC migration in this assay (FIG. 18B).

Figure 19:
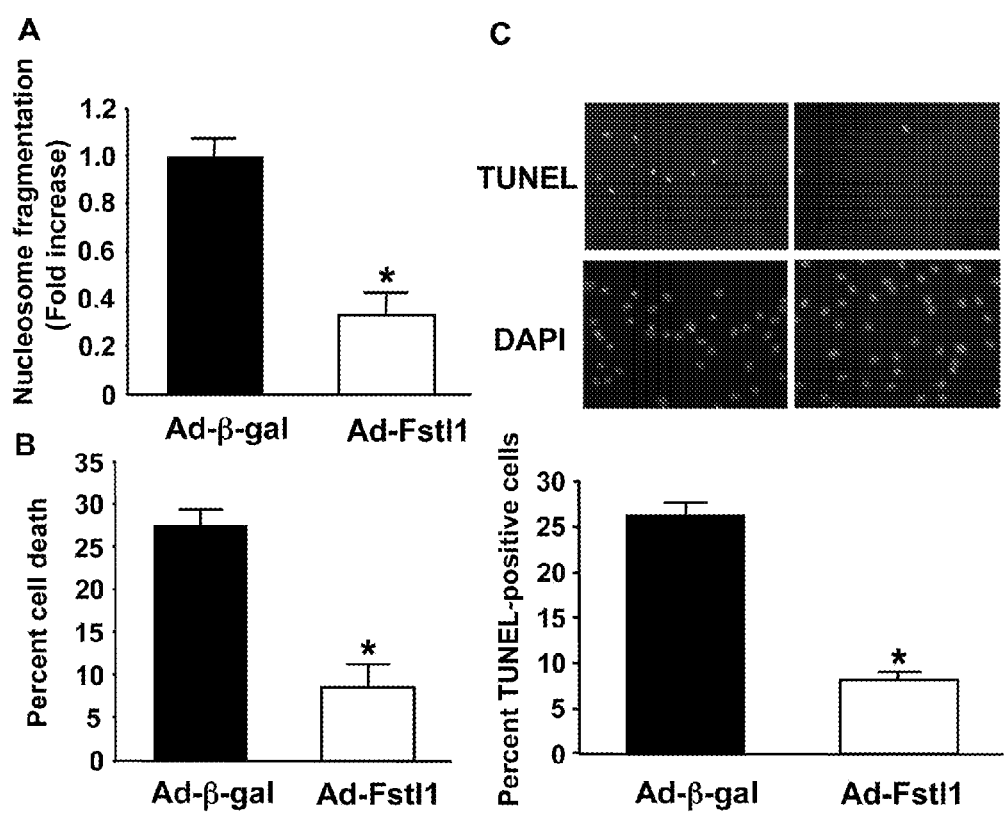
FIG. 19. Fstl1 protects endothelial cells from apoptosis. HUVECs were transduced with Ad-Fstl1 and Ad-β-gal for 8 h followed by incubation with serum-free media for 48 h. A, Inhibitory effect of Fstl1 on Nucleosome fragmentation of HUVECs. Nucleosome fragmentation was assessed by ELISA. Results are expressed relative to the values compared to control. B, Inhibition of HUVEC death by Fstl1 assessed by a quantitative MTS-based assay. C, The frequency of TUNEL-positive HUVECs is reduced after treatment with Fstl1. Representative photomicrographs of TUNEL-positive HUVECs are shown (upper panels). Quantitative analyses of the frequency of TUNEL-positive HUVECs are shown (bottom panel). Apoptotic nuclei were identified by TUNEL staining (green), and total nuclei were identified by DAPI counterstaining (blue). Results are shown as the mean±SEM (n=8-10). *$p<0.01$ vs. Ad-β-gal.

To evaluate the role of Fstl1 in endothelial apoptosis, HUVECs were treated with Ad-Fstl1 or Ad-β-gal followed by 48 hours of incubation in serum-free media. Fstl1 markedly suppressed the extent of nucleosome fragmentation as determined by ELISA (FIG. 19A). Ad-Fstl1 also reduced HUVEC death caused by serum-deprivation as assessed by an MTS-based assay (FIG. 19B). To corroborate these findings, TUNEL-positive cells were analyzed in the HUVEC cultures. As shown in FIG. 19C, treatment with Ad-Fstl1 diminished the frequency of TUNEL-positive cells under serum-deprived conditions.

Example 2f

Fstl1 Stimulates the Phosphorylation of Akt and eNOS

Figure 20:
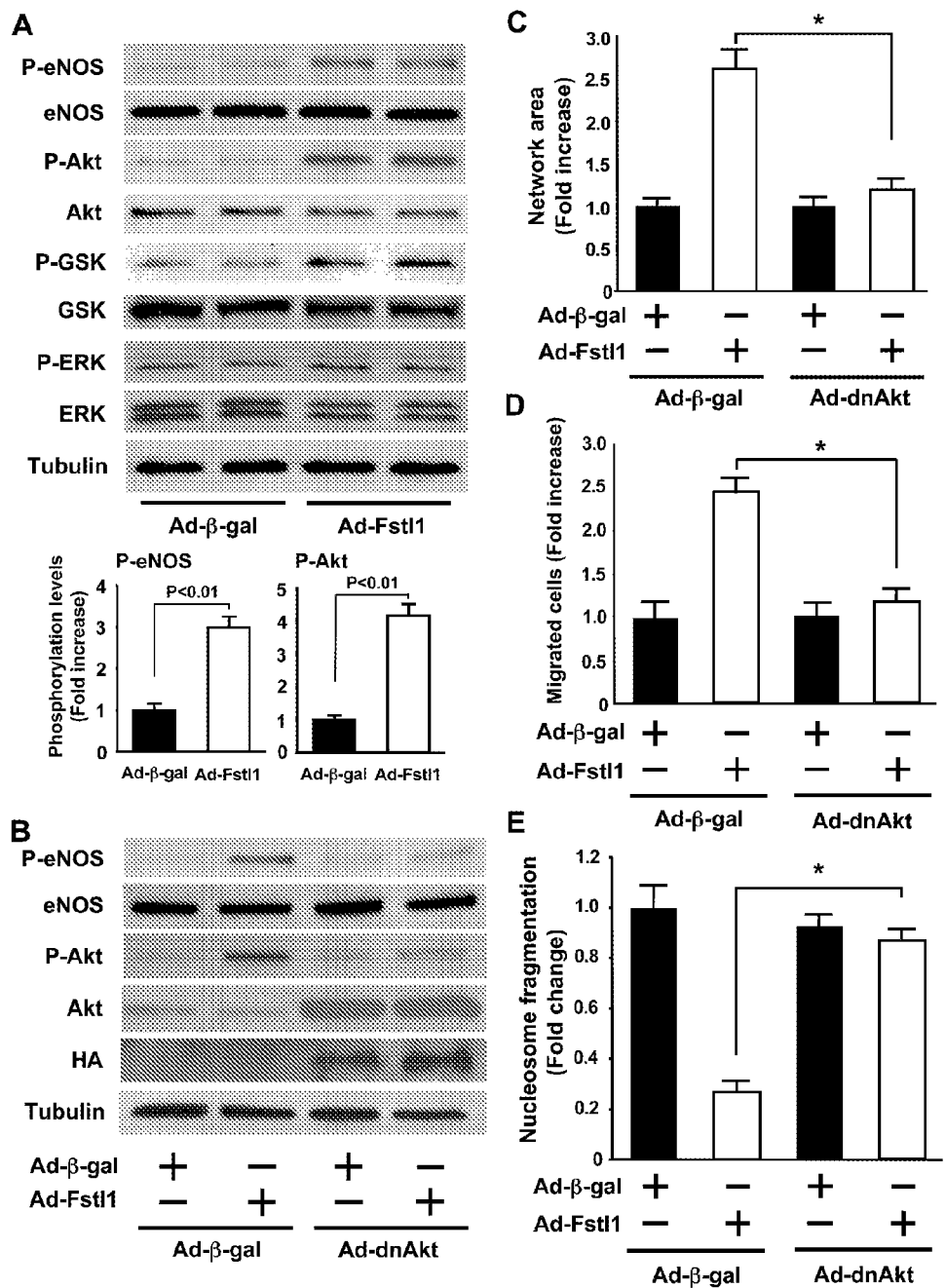
FIG. 20. Fstl1-stimulated endothelial cell responses are dependent on Akt signaling. A, Fstl1-stimulated signaling in endothelial cells. HUVECs were transduced with Ad-Fstl1 and Ad-□-gal for 8 h followed by 24 h of incubation with serum-free media. Changes in the phosphorylation of eNOS (P-eNOS), Akt (P-Akt), GSK (P-GSK) and ERK (P-ERK) following Ad-Fstl1 treatment were determined by Western blot analysis. Representative blots are shown. Representative blots are shown. Relative phosphorylation levels of eNOS and Akt were quantified (n=6) by Image J program. Immunoblots were normalized to total loaded protein. B, Role of Akt in regulation of Fstl1-induced signaling. HUVECs were infected with adenoviral constructs encoding dominant-negative Akt1 (Ad-dnAkt) or Ad-β-gal at a MOI of 10 along with Ad-Fstl1 or Ad-β-gal at a MOI of 10 for 8 h, followed by serum-deprivation for 24 h. Phosphorylation of eNOS (P-eNOS) and Akt (P-Akt) were determined by Western blot analysis. Representative blots are shown from 4 independent experiments. HA: hemagglutinin. C and D, Contribution of Akt to Fstl1-mediated cellular responses. HUVECs were transduced with Ad-dnAkt or Ad-β-gal along with Ad-Fstl1 or Ad-β-gal for 8 h. After 24 h of serum-deprivation, Matrigel (C) or modified Boyden chamber assays (D) were performed. E, Involvement of Akt in Fstl1-induced endothelial cell survival. After transduction with Ad-dnAkt or Ad-βgal along with Ad-Fstl1 or Ad-β-gal for 8 h, cells were incubated in serum-free media. Nucleosome fragmentation was assessed by ELISA. Results are shown as the mean±SEM (n=6-8). Results are expressed relative to the values compared to control. *, $p<0.01$.

Akt has been shown to be a key mediator of growth factor-dependent angiogenic and survival signals in endothelial cells (Fujio, Y., and Walsh, K. (1999), supra; Shiojima, I., and Walsh, K. (2002) *Circ. Res.* 90, 1243-1250). Therefore, to test whether Fstl1 influences Akt signaling in endothelial cells, the activating phosphorylation of Akt at Ser473 was assessed by Western blot analysis. Treatment of HUVECs with Ad-Fstl1 enhanced the phosphorylation of Akt by a factor of 4.2±0.3 (FIG. 20A). Since Akt can phosphorylate eNOS at Ser1179 (Fulton, D., et al. (1999) *Nature* 399, 597-601; Dimmeler, S., et al. (1999) Nature 399, 601-605), eNOS phosphorylation was also examined in these cultures. Ad-Fstl1 stimulation resulted in a 3.0±0.3-fold increase in eNOS phosphorylation at Ser1179 (FIG. 20A). Consistent with an increase in Akt signaling, a 2.0±0.1-fold increase in GSK-3β phosphorylation at Ser9, a downstream target of Akt signaling in endothelial cells (28), was seen under these conditions (FIG. 20A). In contrast, Ad-Fstl1 had no effect on the phosphorylation of ERK at Thr202/Tyr204 (1.3±0.1-fold)(FIG. 20A). To examine the role of Akt in the regulation of eNOS phosphorylation by Fstl1, HUVECs were infected with a HA-tagged dominant-negative Akt (Ad-dnAkt) or Ad-β-gal. Transduction with Ad-dnAkt reduced Fstl1-induced Akt and eNOS phosphorylation (1.0±0.2 in Ad-β-gal, 3.5±0.3 in Ad-Fstl1, 0.9±0.1 in Ad-β-gal+Ad-dnAkt, 1.2±0.2 in Ad-Fstl1+Ad-dnAkt)(FIG. 20B). These data indicate that Akt mediates eNOS phosphorylation downstream from Fstl1.

Example 2g

Role of eNOS Signaling in Fstl1-Stimulated Revascularization

To test whether the activation of Akt signaling is required for Fstl1-stimulated differentiation, migration and survival, HUVECs were infected with Ad-dnAkt or Ad-β-gal, and endothelial cell function and survival was assessed. Transduction with Ad-dnAkt blocked Ad-Fstl1-induced network formation by HUVECs plated on Matrigel (FIG. 20C). Ad-Fstl1-stimulated endothelial cell migration was also diminished by transduction with Ad-dnAkt, whereas Ad-dnAkt had no effect on basal migration (FIG. 20D). Furthermore, transduction with Ad-dnAkt reversed the inhibitory effects of Ad-Fstl1 on the degree of nucleosome fragmentation (FIG. 20E). These results indicate that Akt signaling is required for Fstl1-induced endothelial cell differentiation, migration and survival.

Figure 21:
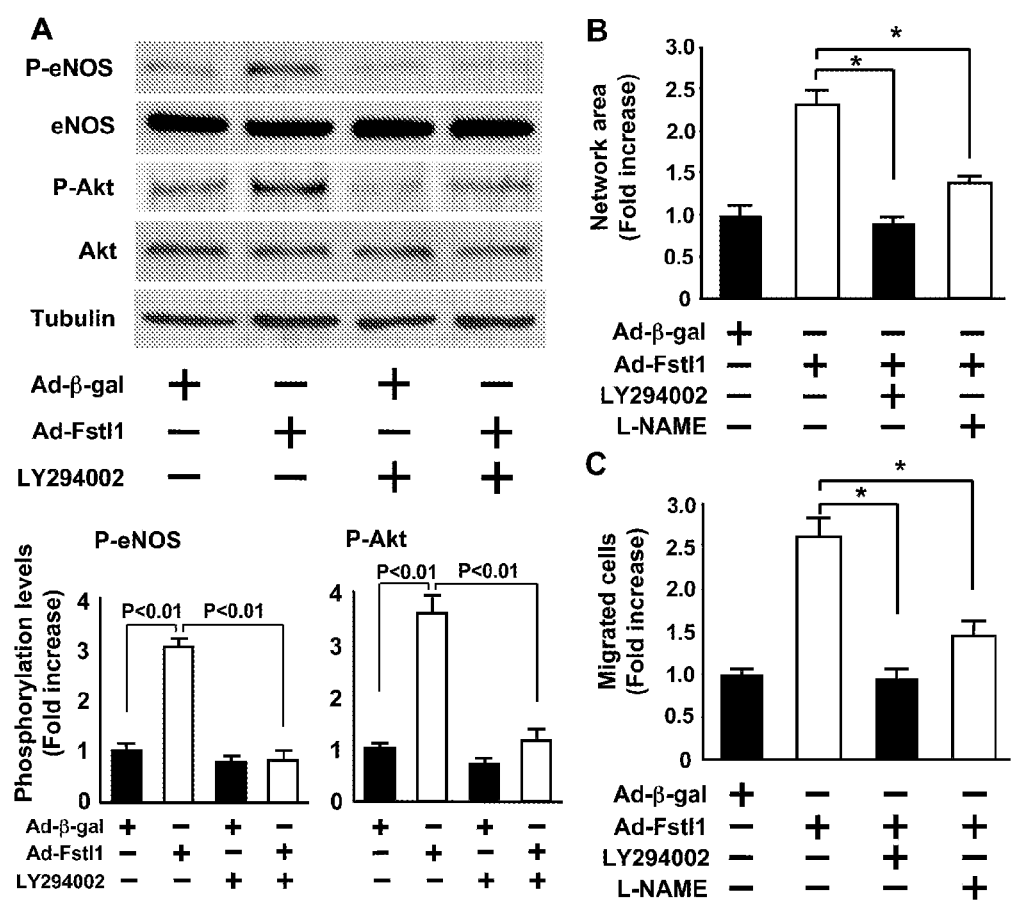
FIG. 21. PI3-kinase and eNOS signaling is involved in Fstl1-induced endothelial cell responses. A, Effect of LY294002 on Fstl1-induced phosphorylation of eNOS and Akt. HUVECs were treated with LY294002 (10 μM) or vehicle following transduction with Ad-Fstl1 or Ad-β-gal. After 24 h serum-deprivation, phosphorylation of eNOS (P-eNOS) and Akt (P-Akt) were determined by Western blot analysis. Representative blots are shown. Relative phosphorylation levels of eNOS and Akt were quantified (n=4) by Image J program. Immunoblots were normalized to total loaded protein. B and C, Contribution of PI3-kinase to Fstl1-mediated endothelial differentiation and migration. HUVECs were treated with LY294002 (10 μM), L-NAME (1 mg/ml) or vehicle along with Ad-Fstl1 or Ad-β-gal for 8 h. After 24-h serum-starvation, Matrigel (B) or modified Boyden chamber assays (C) were performed. Results are shown as the mean±SEM (n=5-8). Results are expressed relative to the values compared to control. *, $p<0.01$.

Akt is activated by many growth factors through the phosphatidylinositol-3 kinase (PI3-kinase)-dependent pathway (Shiojima, I., and Walsh, K. (2002), supra). To investigate whether PI3-kinase participates in Fstl1-induced signaling, HUVECs were treated with PI3-kinase inhibitor LY294002. Treatment with LY294002 abolished Ad-Fstl1-stimulated phosphorylation of Akt and eNOS in HUVECs (FIG. 21A). Ad-Fstl1-stimulated network formation and migration of HUVECs were also blocked by treatment with LY294002 (FIGS. 21B and C). These data indicate that PI3-kinase is essential for endothelial cell responses to Fstl1 and that PI3-kinase functions upstream from the Akt-eNOS regulatory axis in Fstl1-stimulated cells.

To test the role of eNOS in the cellular responses to Fstl1, HUVECs were treated with the NOS inhibitor L-NAME. L-NAME treatment significantly reduced Ad-Fstl1-induced endothelial cell differentiation into network structures and migration (FIGS. 21B and C), indicating that Fstl1 promotes endothelial cell function in an eNOS-dependent manner.

Figure 22:
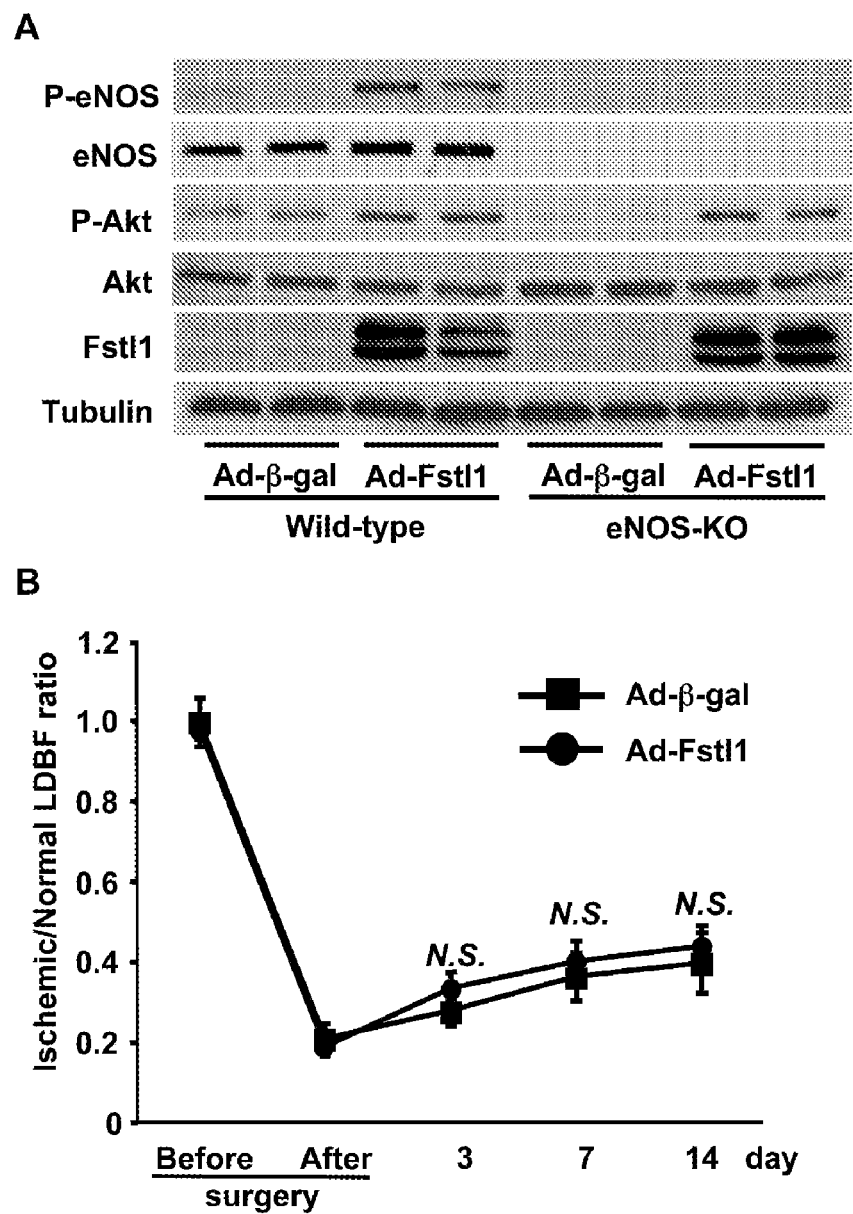
FIG. 22. Fstl1 stimulates ischemia-induced revascularization through an eNOS-dependent mechanism. A, Phosphorylation of eNOS and Akt in ischemic muscle tissues of wild-type and eNOS-KO mice at 6 days after transduction with Ad-Fstl1 or Ad-β-gal. Ad-Fstl1 or Ad-β-gal (Control) was injected into 5 sites in adductor muscle of wild-type and eNOS-KO mice ($2 \times 10^8$ pfu each), 3 days before ischemic surgery. Phosphorylation of eNOS (P-eNOS) and Akt (P-Akt), total eNOS, total Akt and Fstl1 levels were analyzed by Western blotting. Representative blots are shown from 4 independent experiments. B, Quantitative analysis of the ischemic/nonischemic LDBF ratio in eNOS-KO mice treated with Ad-Fstl1 (n=7) and Ad-β-gal (n=7). Results are shown as the mean±SD. N.S, not significant.

To analyze the potential role of eNOS activation in Fstl1-mediated regulation of revascularization in vivo, the phosphorylation status of eNOS and Akt in ischemic muscles of C57/BL6 mice was assessed by Western blot analysis at day 6 after intramuscular injection of Ad-Fstl1 and Ad-β-gal. Ad-Fstl1 treatment stimulated eNOS phosphorylation at serine residue 1177 in ischemic adductor muscle by a factor of 3.3±0.3 without affecting total eNOS protein levels (FIG. 22A). Akt phosphorylation at Ser473 in ischemic muscles was also stimulated 1.9±0.1-fold by Ad-Fstl1 treatment (FIG. 22A).

To assess the contribution of eNOS signaling to the stimulatory actions of Fstl1 on ischemia-driven revascularization in vivo, Ad-Fstl1 or Ad-β-gal was intramuscularly-injected into eNOS-knockout (eNOS-KO) mice 3 days before induction of ischemia. At 6 days after Ad-Fstl1 infection, Fstl1 protein levels in ischemic muscles of eNOS-KO mice increased by a factor of 7.3±0.6 that was similar to a 7.1±0.4-fold increase in wild-type C57/BL6 mice (FIG. 22A). Fstl1 protein levels did not differ between Ad-β-gal-treated wild-type and eNOS-KO mice (1.0±0.1-fold vs. 0.8±0.1-fold). Akt phosphorylation in ischemic muscles of eNOS-KO mice was stimulated by Ad-Fstl1 treatment to a similar extent (1.8±0.1-fold) compared to that of wild-type mice (1.9±0.1-fold)(FIG. 22A). However, in contrast to wild-type mice (FIG. 17B), treatment with Ad-Fstl1 did not promote flow recovery in ischemic hindlimbs in eNOS-KO mice (FIG. 22B). Thus the stimulatory action of Fstl1 on revascularization in vivo is dependent on eNOS.

The present study shows for the first time that Fstl1 plays a role in promoting endothelial cell function and revascularization under conditions of ischemic stress. Fstl1 expression in muscle was upregulated by Akt1 transgene activation during muscle hypertrophy and by ischemic injury. Fstl1 overexpression was shown to enhance endothelial cell differentiation and migration, and diminish endothelial cell apoptosis. Administration of Fstl1 improved revascularization in ischemic limbs of wild-type mice.

It is well documented that Akt-eNOS signaling participates in regulation of endothelial cell function and blood vessel growth under conditions of ischemic stress (Fujio, Y., and Walsh, K. (1999), supra; Shiojima, I., and Walsh, K. (2002), supra; Kureishi, Y., et al. (2000) *Nat. Med.* 6, 1004-1010). The inventors provide evidence that the stimulation of revascularization of ischemic tissue by Fstl1 is dependent on its ability to activate Akt-eNOS signaling in endothelial cells. Fstl1 stimulated the activating phosphorylation of Akt and eNOS, whereas transduction with dominant-negative Akt reduced Fstl1-stimulated endothelial cell differentiation, migration, survival and eNOS phosphorylation. Inhibitors of PI3-kinase or eNOS also blocked the increase in endothelial differentiation and migration caused by Fstl1. The consequences of Fstl1 overexpression on revascularization in ischemic muscle was associated with increased eNOS phosphorylation at Ser1177, and the vascular actions of Fstl1 were abolished in eNOS-KO mice. Collectively, these observations suggest that the Fstl1-Akt-eNOS regulatory signaling axis functions to stimulate vascular cell function under ischemic conditions, thereby promoting revascularization.

It has been proposed that skeletal muscle secretes factors, referred to as "myokines", that influence the behavior of neighboring or remote cells (Pedersen, B. K., et al. (2007) *J. Appl. Physiol.* 103, 1093-1098). Several lines of evidence suggest that Fstl1 can be designated as a myokine that acts on vascular endothelial cells. Both Akt transgene-induced myofiber hypertrophy and ischemic hindlimb surgery led to an increase in tissue-resident and serum levels of Fstl1. Furthermore, Fstl1 is secreted into the media by cultured skeletal muscle cells, and it can directly act on endothelial cell signaling pathways that promote function and survival.

Tissue ischemia leads to the upregulation of multiple growth factors that function to coordinate the repair of the vascular network (Carmeliet, P. (2005), supra). It is also recognized that skeletal muscle hypertrophy is coupled to angiogenesis, through molecular mechanisms that are independent tissue hypoxia (Takahashi, A., et al. (2002), supra). VEGF, a strong stimulator of angiogenesis, is upregulated during myofiber hypertrophy by myogenic Akt signaling. The overexpression of VEGF stimulates angiogenesis in muscle under normoxic conditions leading to the development of a disorganized vascular complex (Lee, R. J., et al. (2000) *Circulation* 102, 898-901). In contrast to VEGF, Fstl1 overexpression accelerates revascularization in ischemic muscle, but does not stimulate vessel growth in normoxic muscle. Thus, it appears that Fstl1 does not function as an "angiogenic factor" per se, but it has salutary effects on the endothelium under conditions of stress and thereby promotes the revascularization process in response to chronic tissue ischemia. Thus, it is hypothesized that the upregulation and secretion of Fstl1 by skeletal muscle, under conditions of hypertrophic growth or ischemic stress, will contribute to revascularization through its ability to promote endothelial cell function.

In agreement with the current study, it was recently reported that Fstl1 is upregulated during cardiac hypertrophy (Oshima, Y., Ouchi, N., Sato, K., Izumiya, Y., Pimentel, D., and Walsh, K. (2008) Circulation, In press.; see also Example 1 herein). In this study, Fstl1 was shown to activate Akt signaling in cardiac myocytes and inhibit apoptosis. Thus, Fstl1 can function as a survival factor for both cardiac myocytes and endothelial cells via the activation of Akt signaling. Fstl1 overexpression has also been shown to protect the heart from ischemia-reperfusion injury in mice. Treatments aimed at increasing angiogenesis represent a promising strategy for treatment of ischemic limb and heart diseases (Vale, P. R., et al. (2001) *J. Interv. Cardiol.* 14, 511-528). Thus, Fstl1 could be considered a potential therapeutic agent for ischemic diseases based upon its ability to directly stimulate blood vessel formation and inhibit the death of cardiovascular cells.

Other members of the follistatin family function to regulate TGF-β superfamily proteins through their ability to function as binding partners (Balemans, W., and Van Hul, W. (2002) *Dev Biol* 250, 231-250). Activin A has been shown to suppress endothelial cell growth and attenuate angiogenesis by a chorioallantoic membrane assay (Breit, S., et al. (2000) *Cancer Res* 60, 4596-4601), and follistatin is reported to promote angiogenesis through its ability to bind to Activin (Kozian, D. H., et al. (1997) *Lab Invest* 76, 267-276). However, it remains to be determined whether Fstl1 binds to members of TGF-β superfamily in a manner that is similar to follistatin (Mashimo, J., et al. (1997) *Cancer Lett* 113, 213-219). In this regard Fstl1 exhibits little amino acid sequence homology with follistatin (7%), and in vitro data show that overexpression of Fstl1 results in enhanced Akt signaling in cultured endothelial cells under conditions of serum deprivation. Thus, it is unlikely that the actions of Fstl1 on endothelial cell signaling and phenotype are mediated by its ability to modulate the function of a second secreted protein. The Fstl1 receptor in endothelial cells remains to be identified.

In conclusion, these data demonstrate that Fstl1 is a myokine that activates Akt-eNOS signaling in endothelial cells. Overexpression of Fstl1 stimulates ischemia-induced revascularization in mice through activation of eNOS. Because the dysregulated eNOS signaling is linked to endothelial dysfunction, impaired neovascularization and atherogenesis (Kawashima, S., and Yokoyama, M. (2004) *Arterioscler Thromb Vasc Biol* 24, 998-1005; Forstermann, U., and Munzel, T. (2006) *Circulation* 113, 1708-1714; Murohara, T., et al. (1998) *J. Clin. Invest.* 101, 2567-2578), strategies to increase Fstl1-eNOS signaling are contemplated as a treatment for vascular complications.

All references cited herein are hereby incorporated herein in their entirety by reference.

TABLE 1

| Genes | Direction | Sequence |
|---|---|---|
| GAPDH | Forward | 5'-TCACCACCATGGAGAAGGC-3' |
|  | Reverse | 5'-GCTAAGCAGTTGGTGGTGCA-3' |
| Fstl1 | Forward | 5'-AACAGCCATCAACATCACCACTTAT-3' |
|  | Reverse | 5'-TTTCCAGTCAGCGTTCTCATCA-3' |
| Follisatin | Forward | 5'-CGAGGAGGATGTGAACGACAA-3' |
|  | Reverse | 5'-GGTCCGCAGTCCACGTTCT-3' |
| Fstl3 | Forward | 5'-CAACCCCGGCCAAGAACT-3' |
|  | Reverse | 5'-CTTCCTCCTCTGCTGGTACTTTG-3' |
| SPARC | Forward | 5'-ATTGGCGAGTTTGAGAAGGT-3 |
|  | Reverse | 5'-TTTGCATGGTCCGATGTAGT-3' |

TABLE 2

Upregulation of Fstl-1 in mRNA level. The left column indicates the microarray analysis and the right column is about quantitative real-time PCR (QRT-PCR) data. By QRT-PCR, significant upregulation of Fstl-1 in mRNA was confirmed.

| Gene name | Array data Fold increase (v.s. Control) | Real-time PCR Fold increase (v.s. Control) |
|---|---|---|
| Follistatin like-1 | 2.73* | 2.04* |
| Follistatin | 0.64 | 0.36 |
| Follistatin like-3 | 1.07 | 0.68 |
| SPARC | 1.83 | 0.73 |
| Akt1 | 5.25* | 7.19* |

Each value is expressed as mean ± SE. n = 3 for each group.
SPARC indicates secreted acidic cysteine rich glycoprotein.
*P < 0.05 compared to control.

TABLE 3

Amino acid and Polynucleotide Sequences of Human FSTL-1

Follistatin-like 1 [*Homo sapiens*] amino acid sequence:
GenBank ACCESSION No. AAH00055, 308 AA

```
  1 mwkrwlalal alvavawvra eeelrskski canvfcgagr ecavtekgep tclcieqckp
 61 hkrpvcgsng ktylnhcelh rdacltgski qvdydghcke kksvspsasp vvcyqsnrde
121 lrrriiqwle aeiipdgwfs kgsnyseild kyfknfdngd srldsseflk fvegnetain
181 ittypdqenn kllrglcvda lielsdenad wklsfqeflk clnpsfnppe kkcaledety
241 adgaetevdc nrcvcacgnw vctamtcdgk nqkgaqtqte eemtryvqel qkhqetaekt
301 krvstkei
```

Polynucleotide sequence:
*Homo sapiens* follistatin-like 1 (FSTL-1)
GenBank Accession No. NM 007085, 3705 bp

```
   1 gatcggcgga gctcccacct ccgcttacag ctcgctgccg ccgtcctgcc ccgcgccccc
  61 aggagacctg gaccagacca cgatgtggaa acgctggctc gcgctcgcgc tcgcgctggt
 121 ggcggtcgcc tgggtccgcg ccgaggaaga gctaaggagc aaatccaaga tctgtgccaa
 181 tgtgttttgt ggagccggcc gggaatgtgc agtcacagaa aaggggaac ccacctgtct
 241 ctgcattgag caatgcaaac ctcacaagag gcctgtgtgt ggcagtaatg caagaccta
 301 cctcaaccac tgtgaactgc atcgagatgc ctgcctcact ggatccaaaa tccaggttga
 361 ttacgatgga cactgcaaag agaagaaatc cgtaagtcca tctgccagcc cagttgtttg
 421 ctatcagtcc aaccgtgatg agctccgacg tcgcatcatc cagtggctgg aagctgagat
 481 cattccagat ggctggttct ctaaaggcag caactacagt gaaatcctag acaagtattt
 541 taagaacttt gataatggtg attctcgcct ggactccagt gaattcctga gtttgtgga
 601 acagaatgaa actgccatca atattacaac gtatccagac caggagaaca caagttgct
 661 taggggactc tgtgttgatg ctctcattga actgtctgat gaaaatgctg attggaaact
 721 cagcttccaa gagtttctca gtgcctcaa cccatctttc aaccctcctg agaagaagtg
 781 tgccctggag gatgaaacgt atgcagatgg agctgagacc gaggtggact gtaaccgctg
 841 tgtctgtgcc tgtggaaatt gggtctgtac agccatgacc tgtgacggaa agaatcagaa
 901 gggggcccag acccagacag aggagggagat gaccagatat gtccaggagc tccaaaagca
 961 tcaggaaaca gctgaaaaga ccaagagagt gagcaccaaa gagatctaat gaggaggcac
1021 agaccagtgt ctggatccca gcatcttctc cacttcagcg ctgagttcag tatacacaag
1081 tgtctgctac agtcgccaaa tcaccagtat ttgcttatat agcaatgagt tttatttttgt
1141 ttatttgttt tgcaataaag gatatgaagg tggctggcta ggaagggaag gccacagcc
1201 ttcatttcta ggagtgcttt aagagaaact gtaaatggtg ctctggggct ggaggctagt
1261 aaggaaactg catcacgatt gaaagaggaa cagacccaaa tctgaacctc ttttgagttt
1321 actgcatctg tcagcaggct gcaggagtg cacacgatgc cagagagaac ttagcagggt
1381 gtccccggag gagaggtttg ggaagctcca cggagaggaa cgctctctgc ttccagcctc
1441 tttccattgc cgtcagcatg acagacctcc agcatccacg catctcttgg tcccaataac
1501 tgcctctaga tacatagcca tactgctagt taacccagtg tccctcagac ttggatggag
1561 tttctgggag ggtacaccca aatgatgcag atacttgtat actttgagcc ccttagcgac
1621 ctaaccaaat tttaaaaata cttttttacca aaggtgctat ttctctgtaa aacactttt
1681 ttttggcaag ttgactttat tcttcaatta ttatcattat attattgttt tttaatattt
1741 tattttcttg actaggtatt aagcttttgt aattattttt cagtagtccc accacttcat
```

TABLE 3-continued

Amino acid and Polynucleotide Sequences of Human FSTL-1

```
1801 aggtggaagg agtttggggt tcttcctggt gcaggggctg aaataaccca gatgccccca 1861 ccctgccaca tactagatgc agcccatagt tggcccccct agcttccagc agtccactat 1921 ctgccagagg agcaagggtg ccttagaccg aagccagggg aagaagcatc ttcataaaaa 1981 actttcaaga tccaaacatt aatttgtttt tatttattct gagaagttga ggcaaatcag 2041 tattcccaag gatggcgaca agggcagcca agcagggctt aggatatccc agcctaccaa 2101 tatgctcatt cgactaacta ggagggtgag ttggccctgt ctcttctttt ttctggacct 2161 cagtttcctc agtgagctgg taagaatgca ctaacctttt gatttgataa gttataaatt 2221 ctgtggttct gatcattggt ccagagggga gataggttcc tgtgattttt ccttcttctc 2281 tatagaataa atgaaatctt gttactagaa caagaaatgt cagatggcca aaaacaagat 2341 gaccagattt gatctcagcc tgatgaccct acaggtcgtg ctatgatatg gagtcctcat 2401 gggtaaagca ggaagagagt gggaaagaga accaccccac tctgtcttca tatttgcatt 2461 tcatgtttaa cctccggctg gaaatagaaa gcattccctt agagatgagg ataaaagaaa 2521 gtttcagatt caacaggggg aagaaaatgg agatttaatc ctaaaactgt gacttgggga 2581 ggtcagtcat ttacagttag tcctgtgtct ttcgacttct gtgattatta accccactca 2641 ctaccctgtt tcagatgcat ttggaatacc aaagattaaa tccttgacat aagatctcat 2701 ttgcagaaag cagattaaag accatcagaa ggaaattatt taggttgtaa tgcacaggca 2761 actgtgagaa actgttgtgc caaaaataga attccttcta gttttcttg ttctcatttg 2821 aaaggagaaa attccacttt gtttagcatt tcaagctttt atgtatccat cccatctaaa 2881 aactcttcaa actccacttg ttcagtctga atgcagctc cctgtccaag tgccttggag 2941 aactcacagc agcacgcctt aatcaaaggt tttaccagcc cttggacact atgggaggag 3001 ggcaagagta caccaatttg ttaaaagcaa gaaaccacag tgtctcttca ctagtcattt 3061 agaacatggt tatcatccaa gactactcta ccctgcaaca ttgaactccc aagagcaaat 3121 ccacattcct cttgagttct gcagcttctg tgtaaatagg gcagctgtcg tctatgccgt 3181 agaatcacat gatctgagga ccattcatgg aagctgctaa atagcctagt ctggggagtc 3241 ttccataaag ttttgcatgg agcaaacaaa caggattaaa ctaggtttgg ttccttcagc 3301 cctctaaaag catagggctt agcctgcagg cttccttggg ctttctctgt gtgtgtagtt 3361 ttgtaaacac tatagcatct gttaagatcc agtgtccatg gaaacattcc cacatgccgt 3421 gactctggac tatatcagtt tttggaaagc agggttcctc tgcctgctaa caagcccacg 3481 tggaccagtc tgaatgtctt tcctttacac ctatgttttt aagtagtcaa acttcaagaa 3541 acaatctaaa caagtttctg ttgcatatgt gtttgtgaac ttgtatttgt atttagtagg 3601 cttctatatt gcatttaact tgttttttgta actcctgatt cttccttttc ggatactatt 3661 gatgaataaa gaaattaaag tgaaaaaaaa aaaaaaaaa aaaaa
```

What is claimed is:

1. A method of treating ischemic injury in a mammal, the method comprising administering a follistatin-like protein 1 polypeptide, or a portion thereof sufficient to activate Akt-1 signaling activity, to a mammal in need thereof, wherein said administering treats an ischemic injury, and wherein said polypeptide can activate Akt-1 signaling and comprises an amino acid sequence at least 95% identical to SEQ ID NO: 1.

2. The method of claim 1 wherein said ischemic injury comprises ischemia/reperfusion injury.

3. The method of claim 1, wherein said ischemic injury is ischemic injury of cardiac muscle.

4. The method of claim 1, wherein said administering comprises administering a soluble follistatin-like protein 1 polypeptide or a portion thereof.

5. A method of promoting revascularization of ischemic tissue, the method comprising administering to a mammal in need thereof a follistatin-like protein 1 polypeptide or a portion thereof sufficient to activate Akt-1 signaling activity, wherein said administering promotes increased blood flow in said tissue, and wherein said administering occurs during or following an ischemic event, and wherein said polypeptide can activate Akt-1 signaling and comprises an amino acid sequence at least 95% identical to SEQ ID NO: 1.

6. The method of claim 5, wherein said tissue is muscle.

7. The method of claim 6, wherein said muscle is cardiac or skeletal muscle.

8. The method of claim 5, wherein said administering promotes an activity selected from the group consisting of:
endothelial cell growth, survival, and differentiation.

9. The method of claim 5, wherein said mammal suffers from an ischemic limb disease.

10. The method of claim 5, wherein said mammal suffers from diabetes, or atherosclerosis.

* * * * *

SEQUENCE LISTING

<160> NUMBER OF SEQ ID NOS: 12

<210> SEQ ID NO 1
<211> LENGTH: 308
<212> TYPE: PRT

-continued

<213> ORGANISM: Homo sapiens

<400> SEQUENCE: 1

Met Trp Lys Arg Trp Leu Ala Leu Ala Leu Ala Val Ala Val Ala
1               5                   10                  15

Trp Val Arg Ala Glu Glu Glu Leu Arg Ser Lys Ser Lys Ile Cys Ala
            20                  25                  30

Asn Val Phe Cys Gly Ala Gly Arg Glu Cys Ala Val Thr Glu Lys Gly
        35                  40                  45

Glu Pro Thr Cys Leu Cys Ile Glu Gln Cys Lys Pro His Lys Arg Pro
    50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Arg Ile Ile Gln Trp
        115                 120                 125

Leu Glu Ala Glu Ile Ile Pro Asp Gly Trp Phe Ser Lys Gly Ser Asn
    130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
    210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Glu Met Thr Arg Tyr Val Gln
        275                 280                 285

Glu Leu Gln Lys His Gln Glu Thr Ala Glu Lys Thr Lys Arg Val Ser
    290                 295                 300

Thr Lys Glu Ile
305

<210> SEQ ID NO 2
<211> LENGTH: 3705
<212> TYPE: DNA
<213> ORGANISM: Homo sapiens

<400> SEQUENCE: 2
gatcggcgga gctcccacct ccgcttacag ctcgctgccg ccgtcctgcc ccgcgccccc      60
aggagacctg gaccagacca cgatgtggaa acgctggctc gcgctcgcgc tcgcgctggt     120
ggcggtcgcc tggtccgcg ccgaggaaga gctaaggagc aaatccaaga tctgtgccaa     180
tgtgttttgt ggagccggcc gggaatgtgc agtcacagag aaaggggaac ccacctgtct     240

```
ctgcattgag caatgcaaac ctcacaagag gcctgtgtgt ggcagtaatg caagaccta    300 cctcaaccac tgtgaactgc atcgagatgc ctgcctcact ggatccaaaa tccaggttga   360
ttacgatgga cactgcaaag agaagaaatc cgtaagtcca tctgccagcc cagttgtttg   420
ctatcagtcc aaccgtgatg agctccgacg tcgcatcatc cagtggctgg aagctgagat   480
cattccagat ggctggttct ctaaaggcag caactacagt gaaatcctag acaagtattt   540
taagaacttt gataatggtg attctcgcct ggactccagt gaattcctga gtttgtgga    600 acagaatgaa actgccatca atattacaac gtatccagac caggagaaca caagttgct   660 taggggactc tgtgttgatg ctctcattga actgtctgat gaaatgctg attggaaact    720 cagcttccaa gagtttctca agtgcctcaa cccatctttc aaccctcctg agaagaagtg   780
tgccctggag gatgaaacgt atgcagatgg agctgagacc gaggtggact gtaaccgctg   840
tgtctgtgcc tgtggaaatt gggtctgtac agccatgacc tgtgacggaa agaatcagaa   900
gggggcccag acccagacag aggaggagat gaccagatat gtccaggagc tccaaaagca   960
tcaggaaaca gctgaaaaga ccaagagagt gagcaccaaa gagatctaat gaggaggcac  1020
agaccagtgt ctggatccca gcatcttctc cacttcagcg ctgagttcag tatacacaag  1080
tgtctgctac agtcgccaaa tcaccagtat ttgcttatat agcaatgagt tttatttttgt 1140 ttatttgttt tgcaataaag gatatgaagg tggctggcta ggaagggaag gccacagcc   1200 ttcatttcta ggagtgcttt aagagaaact gtaaatggtg ctctggggct ggaggctagt  1260
aaggaaactg catcacgatt gaaagaggaa cagacccaaa tctgaacctc ttttgagttt   1320
actgcatctg tcagcaggct gcaggagtg cacacgatgc cagagagaac ttagcagggt   1380
gtccccggag gagaggtttg ggaagctcca cggagaggaa cgctctctgc ttccagcctc  1440
tttccattgc cgtcagcatg acagacctcc agcatccacg catctcttgg tcccaataac  1500
tgcctctaga tacatagcca tactgctagt taacccagtg tccctcagac ttggatggag  1560
tttctgggag ggtacaccca atgatgcag atacttgtat acttcgagcc ccttagcgac   1620
ctaaccaaat tttaaaaata cttttttacca aaggtgctat ttctctgtaa aacacttttt   1680
ttttggcaag ttgactttat tcttcaatta ttatcattat attattgttt tttaatattt   1740
tattttcttg actaggtatt aagcttttgt aattatttttt cagtagtccc accacttcat  1800
aggtggaagg agtttggggt tcttcctggt gcaggggctg aaataaccca gatgccccca   1860
ccctgccaca tactagatgc agcccatagt tggccccccct agcttccagc agtccactat   1920
ctgccagagg agcaagggtg ccttagaccg aagccagggg aagaagcatc ttcataaaaa   1980 acttcaaga tccaaacatt aatttgtttt tatttattct gagaagttga ggcaaatcag    2040
tattcccaag gatggcgaca agggcagcca agcagggctt aggatatccc agcctaccaa   2100
tatgctcatt cgactaacta ggagggtgag ttggccctgt ctcttctttt ttctggacct   2160
cagtttcctc agtgagctgg taagaatgca ctaaccttttt gatttgataa gttataaatt   2220
ctgtggttct gatcattggt ccagagggga gataggttcc tgtgatttttt ccttcttctc   2280 tatagaataa atgaaatctt gttactagaa caagaaatgt cagatggcca aaaacaagat   2340
gaccagattt gatctcagcc tgatgaccct acaggtcgtg ctatgatatg gagtcctcat   2400
gggtaaagca ggaagagagt gggaaagaga accaccccac tctgtcttca tatttgcatt   2460
tcatgtttaa cctccggctg gaaatagaaa gcattccctt agagatgagg ataaaagaaa   2520
gtttcagatt caacaggggg aagaaaatgg agatttaatc ctaaaactgt gacttgggga   2580
ggtcagtcat ttacagttag tcctgtgtct ttcgacttct gtgattatta accccactca   2640
```

-continued

```
ctaccctgtt tcagatgcat ttggaatacc aaagattaaa tccttgacat aagatctcat    2700
ttgcagaaag cagattaaag accatcagaa ggaaattatt taggttgtaa tgcacaggca    2760
actgtgagaa actgttgtgc caaaaataga attccttcta gttttcttg ttctcatttg     2820 aaaggagaaa attccacttt gtttagcatt tcaagctttt atgtatccat cccatctaaa    2880
aactcttcaa actccacttg ttcagtctga aatgcagctc cctgtccaag tgccttggag    2940
aactcacagc agcacgcctt aatcaaaggt tttaccagcc cttggacact atgggaggag    3000
ggcaagagta caccaatttg ttaaaagcaa gaaaccacag tgtctcttca ctagtcattt    3060
agaacatggt tatcatccaa gactactcta ccctgcaaca ttgaactccc aagagcaaat    3120
ccacattcct cttgagttct gcagcttctg tgtaaatagg gcagctgtcg tctatgccgt    3180
agaatcacat gatctgagga ccattcatgg aagctgctaa atagcctagt ctggggagtc    3240
ttccataaag ttttgcatgg agcaaacaaa caggattaaa ctaggtttgg ttccttcagc    3300
cctctaaaag catagggctt agcctgcagg cttccttggg cttttctctgt gtgtgtagtt    3360 ttgtaaacac tatagcatct gttaagatcc agtgtccatg gaaacattcc cacatgccgt    3420
gactctggac tatatcagtt tttggaaagc agggttcctc tgcctgctaa caagcccacg    3480
tggaccagtc tgaatgtctt tcctttacac ctatgttttt aagtagtcaa acttcaagaa    3540
acaatctaaa caagtttctg ttgcatatgt gtttgtgaac ttgtatttgt atttagtagg    3600
cttctatatt gcatttaact tgtttttgta actcctgatt cttccttttc ggatactatt    3660
gatgaataaa gaaattaaag tgaaaaaaaa aaaaaaaaa aaaaa                     3705
```

<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 3
tcaccaccat ggagaaggc                                                  19

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4
gctaagcagt tggtggtgca                                                 20

<210> SEQ ID NO 5
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
aacagccatc aacatcacca cttat                                           25

<210> SEQ ID NO 6

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tttccagtca gcgttctcat ca                                              22

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cgaggaggat gtgaacgaca a                                               21

<210> SEQ ID NO 8
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
ggtccgcagt ccacgttct                                                  19

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
caaccccggc caagaact                                                   18

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
cttcctcctc tgctggtact ttg                                             23

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
```

```
attggcgagt ttgagaaggt                                              20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
tttgcatggt ccgatgtagt                                              20
```